(12) United States Patent
Allen et al.

(10) Patent No.: US 7,112,207 B2
(45) Date of Patent: Sep. 26, 2006

(54) MINIMALLY INVASIVE MITRAL VALVE REPAIR METHOD AND APPARATUS

(75) Inventors: William J. Allen, Stratford, CT (US); Alan B. Bachman, New Haven, CT (US); Scott Reed, Monroe, CT (US); Leland R. Adams, Ansonia, CT (US); Robert R. Steckel, Norwalk, CT (US)

(73) Assignee: Edwards Lifesciences Corporation, Irvine, CA (US)

( * ) Notice: Subject to any disclaimer, the term of this patent is extended or adjusted under 35 U.S.C. 154(b) by 566 days.

(21) Appl. No.: 10/423,046

(22) Filed: Apr. 24, 2003

(65) Prior Publication Data

US 2004/0093023 A1 May 13, 2004

Related U.S. Application Data

(63) Continuation of application No. 09/562,406, filed on May 1, 2000, now Pat. No. 6,626,930.

(60) Provisional application No. 60/161,296, filed on Oct. 21, 1999.

(51) Int. Cl.
*A61B 17/10* (2006.01)
*A61B 19/00* (2006.01)
*A61B 17/08* (2006.01)

(52) U.S. Cl. .................. 606/139; 128/898; 606/144

(58) Field of Classification Search .......... 606/150, 606/153, 216, 221, 213, 214, 215, 219, 139, 606/144, 148, 220, 232, 123; 128/898; 604/171–176
See application file for complete search history.

(56) References Cited

U.S. PATENT DOCUMENTS

| | | | |
|---|---|---|---|
| 3,805,793 A | 4/1974 | Wright | |
| 4,350,160 A | 9/1982 | Kolesov et al. | |
| 5,080,663 A | 1/1992 | Mills et al. | |
| 5,242,456 A | 9/1993 | Nash et al. | |
| 5,267,958 A | 12/1993 | Buchbinder et al. | |
| 5,330,442 A | 7/1994 | Green et al. | |
| 5,374,275 A | 12/1994 | Bradley et al. | |
| 5,403,326 A | 4/1995 | Harrison et al. | |
| 5,443,446 A | 8/1995 | Shturman | |

(Continued)

FOREIGN PATENT DOCUMENTS

DE 19725739 4/1999

(Continued)

*Primary Examiner*—Julian W. Woo
(74) *Attorney, Agent, or Firm*—David L. Hauser; Rajiv Yadav

(57) ABSTRACT

The present invention is directed to an apparatus and method for the stabilization and fastening of two pieces of tissue. A single device may be used to both stabilize and fasten the two pieces of tissue, or a separate stabilizing device may be used in conjunction with a fastening device. The stabilizing device may comprise a probe with vacuum ports and/or mechanical clamps disposed at the distal end to approximate the two pieces of tissue. After the pieces of tissue are stabilized, they are fastened together using sutures or clips. One exemplary embodiment of a suture-based fastener comprises a toggle and suture arrangement deployed by a needle, wherein the needle enters the front side of the tissue and exits the blind side. In a second exemplary embodiment, the suture-based fastener comprises a needle connected to a suture. The needle enters the blind side of the tissue and exits the front side. The suture is then tied in a knot to secure the pieces of tissue. One example of a clip-based fastener comprises a spring-loaded clip having two arms with tapered distal ends and barbs. The probe includes a deployment mechanism which causes the clip to pierce and lockingly secure the two pieces of tissue.

20 Claims, 45 Drawing Sheets

U.S. PATENT DOCUMENTS

| | | |
|---|---|---|
| 5,458,131 A | 10/1995 | Wilk |
| 5,474,573 A | 12/1995 | Hatcher |
| 5,540,704 A | 7/1996 | Gordon et al. |
| 5,569,274 A | 10/1996 | Rapacki et al. |
| 5,573,540 A | 11/1996 | Yoon |
| 5,575,800 A | 11/1996 | Gordon |
| 5,578,044 A | 11/1996 | Gordon et al. |
| 5,601,574 A | 2/1997 | Stefanchik et al. |
| 5,609,598 A | 3/1997 | Laufer et al. |
| 5,662,664 A | 9/1997 | Gordon et al. |
| 5,685,867 A | 11/1997 | Twardowski et al. |
| 5,695,457 A | 12/1997 | St. Goar et al. |
| 5,695,504 A | 12/1997 | Gifford et al. |
| 5,700,272 A | 12/1997 | Gordon et al. |
| 5,713,910 A | 2/1998 | Gordon et al. |
| 5,713,911 A | 2/1998 | Racenet et al. |
| 5,716,367 A | 2/1998 | Koike et al. |
| 5,741,277 A | 4/1998 | Gordon et al. |
| 5,741,279 A | 4/1998 | Gordon et al. |
| 5,766,183 A | 6/1998 | Sauer |
| 5,792,094 A | 8/1998 | Stevens et al. |
| 5,792,153 A | 8/1998 | Swain et al. |
| 5,810,847 A | 9/1998 | Laufer et al. |
| 5,814,097 A | 9/1998 | Sterman et al. |
| 5,836,956 A | 11/1998 | Buelna et al. |
| 5,839,639 A | 11/1998 | Sauer et al. |
| 5,849,019 A | 12/1998 | Yoon |
| 5,860,992 A | 1/1999 | Daniel et al. |
| 5,885,238 A | 3/1999 | Stevens et al. |
| 5,891,159 A | 4/1999 | Sherman et al. |
| 5,891,160 A | 4/1999 | Williamson et al. |
| 5,924,424 A | 7/1999 | Stevens et al. |
| 5,928,224 A | 7/1999 | Laufer |
| 5,928,250 A | 7/1999 | Koike et al. |
| 5,968,059 A | 10/1999 | Ellis et al. |
| 5,972,020 A | 10/1999 | Carpentier et al. |
| 5,976,159 A | 11/1999 | Bolduc et al. |
| 6,010,531 A | 1/2000 | Donlon et al. |
| 6,015,417 A | 1/2000 | Reynolds, Jr. |
| 6,015,427 A | 1/2000 | Mueller et al. |
| 6,029,671 A | 2/2000 | Stevens et al. |
| 6,047,700 A | 4/2000 | Eggers et al. |
| 6,056,760 A | 5/2000 | Koike et al. |
| 6,080,182 A | 6/2000 | Shaw et al. |
| 6,083,219 A | 7/2000 | Laufer |
| 6,088,889 A | 7/2000 | Luther et al. |
| 6,117,159 A | 9/2000 | Huebsch et al. |
| 6,149,660 A | 11/2000 | Laufer et al. |
| 6,157,852 A | 12/2000 | Selmon et al. |
| 6,162,233 A | 12/2000 | Williamson et al. |
| 6,165,183 A * | 12/2000 | Kuehn et al. ............... 606/139 |
| 6,165,204 A | 12/2000 | Levinson et al. |
| 6,190,357 B1 | 2/2001 | Ferrari et al. |
| 6,210,419 B1 | 4/2001 | Mayenberger et al. |
| 6,234,995 B1 | 5/2001 | Peacock |
| 6,269,819 B1 | 8/2001 | Oz et al. |
| 6,312,447 B1 * | 11/2001 | Grimes ....................... 606/219 |
| 6,443,922 B1 | 9/2002 | Roberts et al. |
| 6,461,366 B1 | 10/2002 | Seguin |
| 6,508,777 B1 | 1/2003 | Macoviak et al. |
| 6,582,388 B1 | 6/2003 | Coleman et al. |
| 6,626,930 B1 | 9/2003 | Allen et al. |
| 6,629,534 B1 | 10/2003 | St. Goar et al. |
| 6,752,813 B1 | 6/2004 | Goldfarb et al. |
| 6,770,083 B1 | 8/2004 | Seguin |
| 6,875,224 B1 | 4/2005 | Grimes |
| 2002/0049402 A1 | 4/2002 | Peacock |
| 2002/0107531 A1 | 8/2002 | Schreck et al. |
| 2003/0130571 A1 | 7/2003 | Lattouf |

FOREIGN PATENT DOCUMENTS

| | | |
|---|---|---|
| DE | 19725739 C | 4/1999 |
| EP | 0570915 A2 | 11/1993 |
| EP | 0769272 A1 | 4/1997 |
| EP | 0861632 A1 | 9/1998 |
| WO | 9515715 | 6/1995 |
| WO | WO 95/15715 | 6/1995 |
| WO | WO 95/25468 | 9/1995 |
| WO | 9727893 | 8/1997 |
| WO | WO 97/27807 | 8/1997 |
| WO | WO 97/27893 | 8/1997 |
| WO | 9857585 | 12/1998 |
| WO | WO 98/57585 | 12/1998 |
| WO | 9900059 | 1/1999 |
| WO | WO 99/00059 | 1/1999 |
| WO | WO99/13777 | 3/1999 |
| WO | WO 99/13777 | 3/1999 |
| WO | WO 99/15223 | 4/1999 |
| WO | 0003759 | 1/2000 |
| WO | WO 00/03759 | 2/2000 |
| WO | 0059382 | 10/2000 |
| WO | 0060995 | 10/2000 |
| WO | WO 00/59382 | 10/2000 |
| WO | WO 00/60995 | 10/2000 |
| WO | WO 01/26557 | 4/2001 |
| WO | WO 01/28432 | 4/2001 |
| WO | WO 01/66018 | 9/2001 |
| WO | WO 01/95809 | 12/2001 |
| WO | WO 02/24078 | 3/2002 |
| WO | WO 02/34167 | 5/2002 |

* cited by examiner

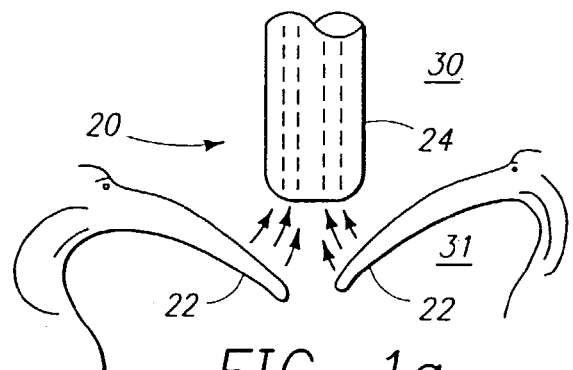
FIG. 1a
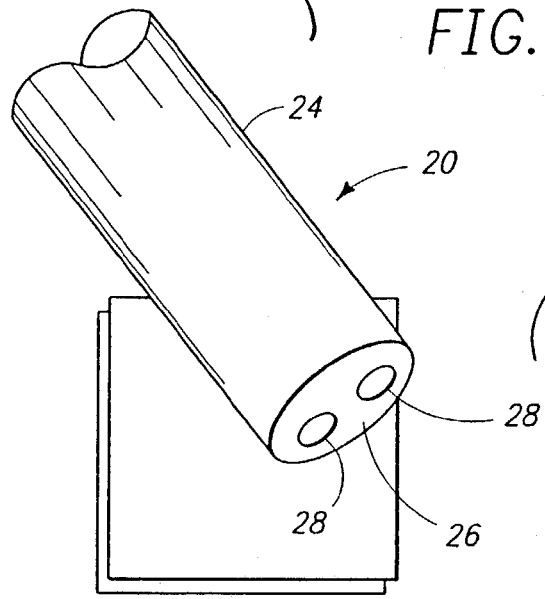
FIG. 1b
FIG. 1
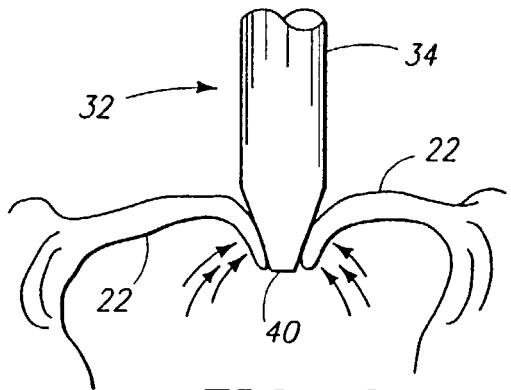
FIG. 2a
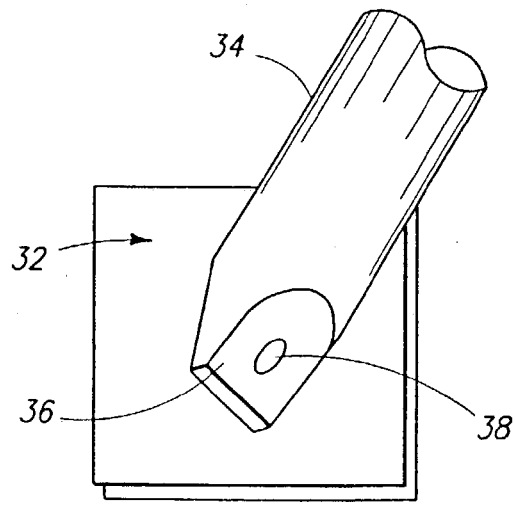
FIG. 2

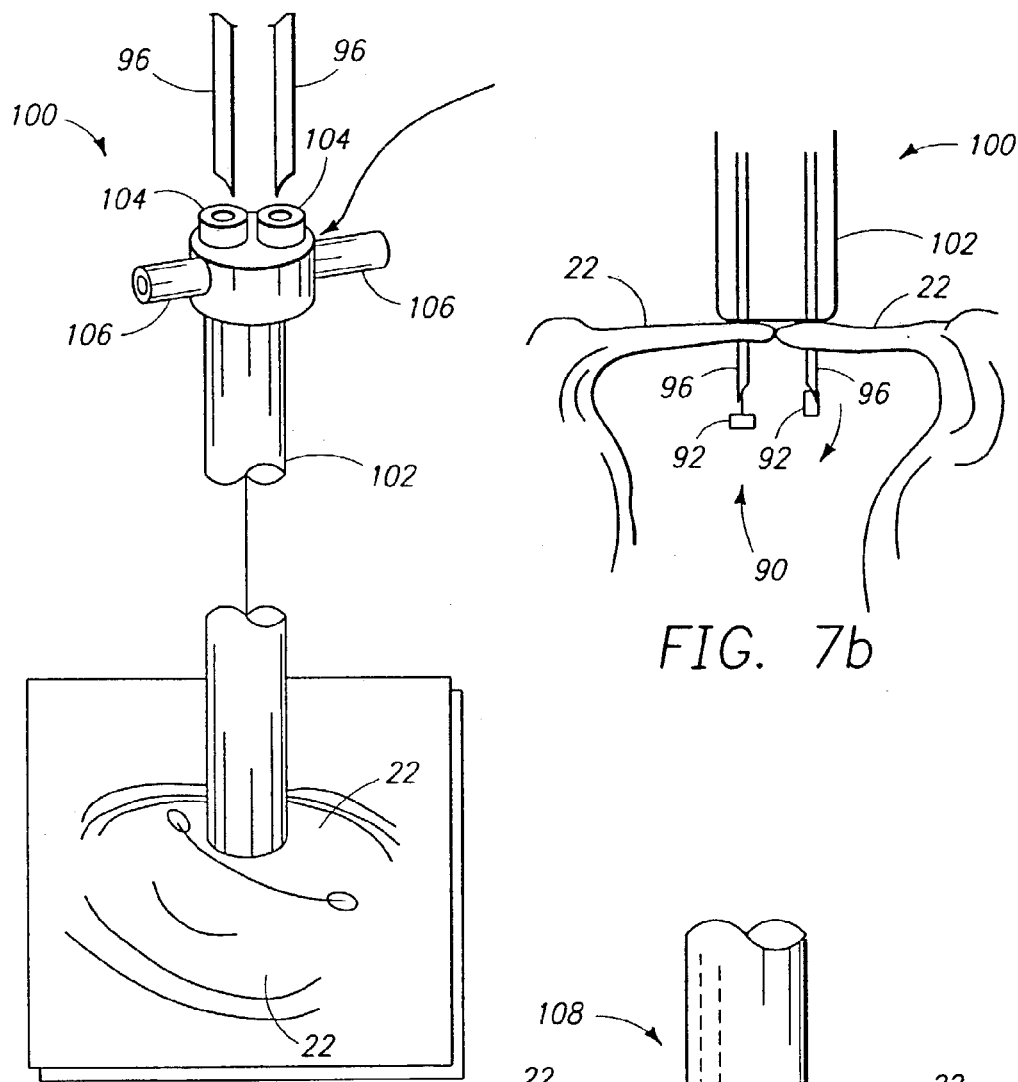
FIG. 7a
FIG. 7b
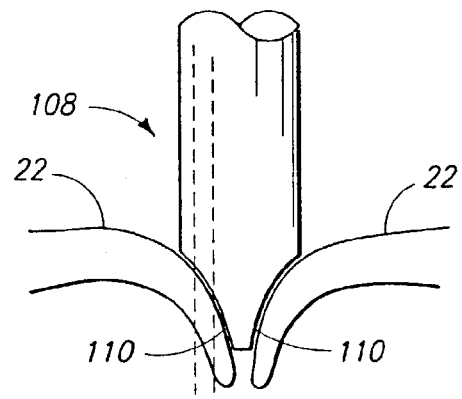
FIG. 8

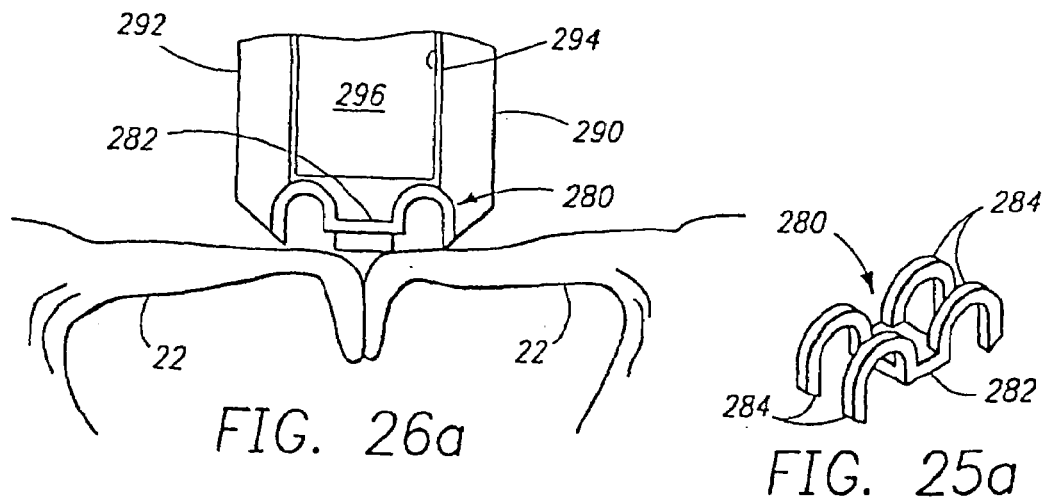
FIG. 26a
FIG. 25a
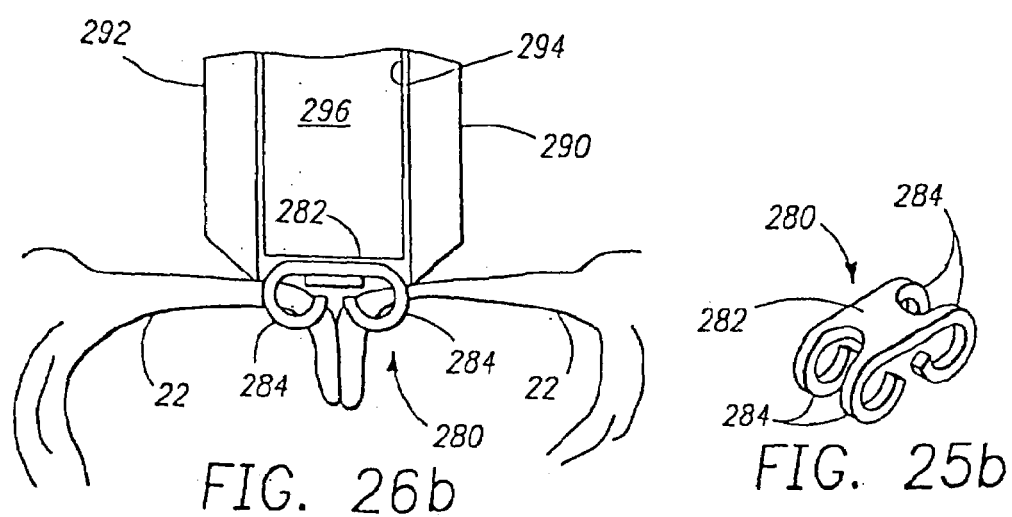
FIG. 26b
FIG. 25b
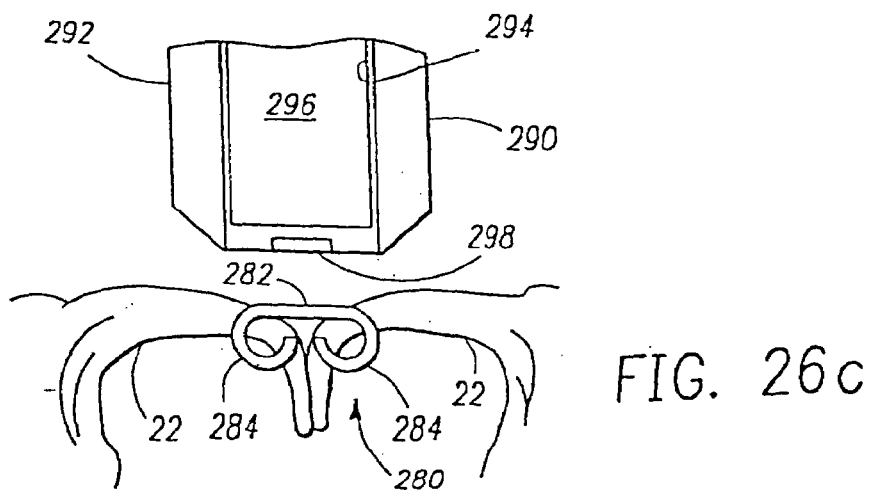
FIG. 26c

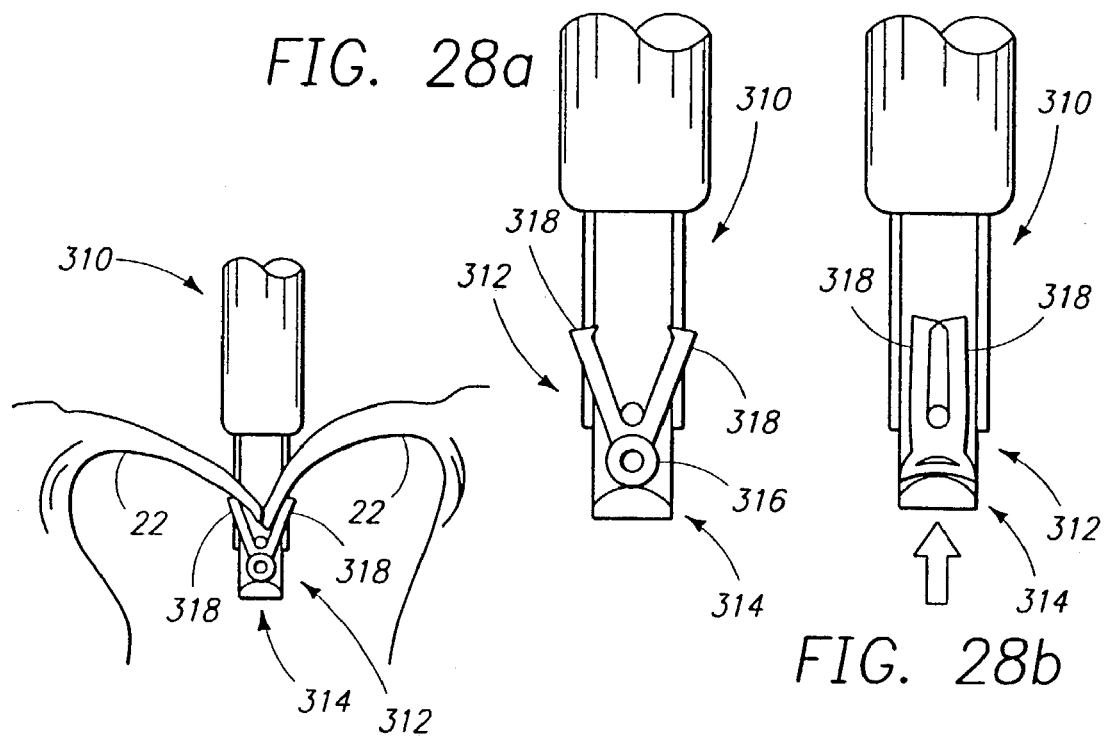
FIG. 28a
FIG. 28b
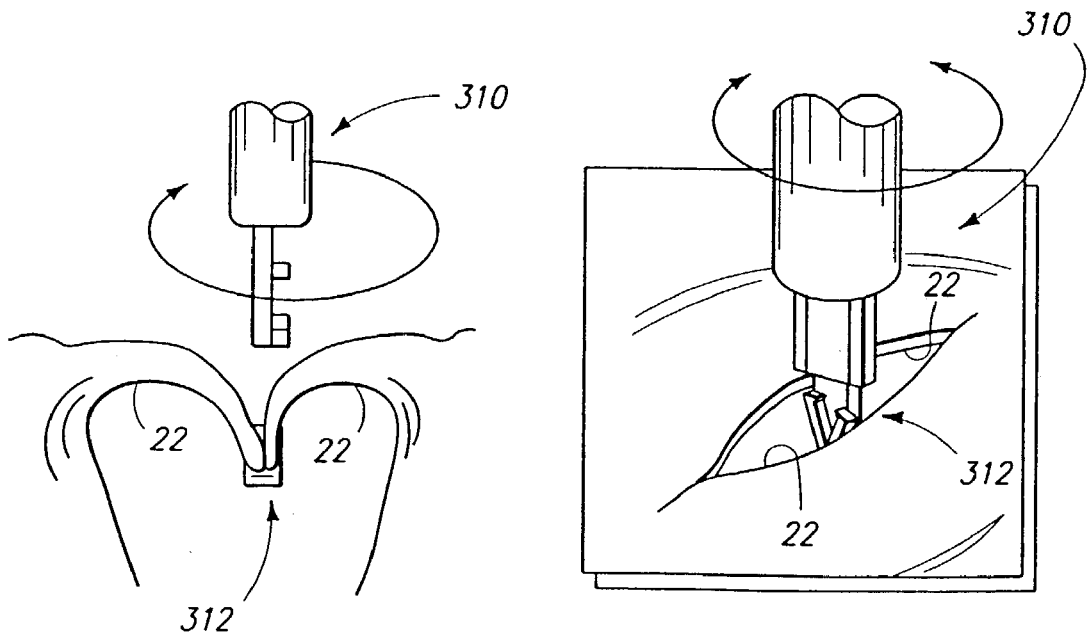
FIG. 29b
FIG. 29c
FIG. 29a

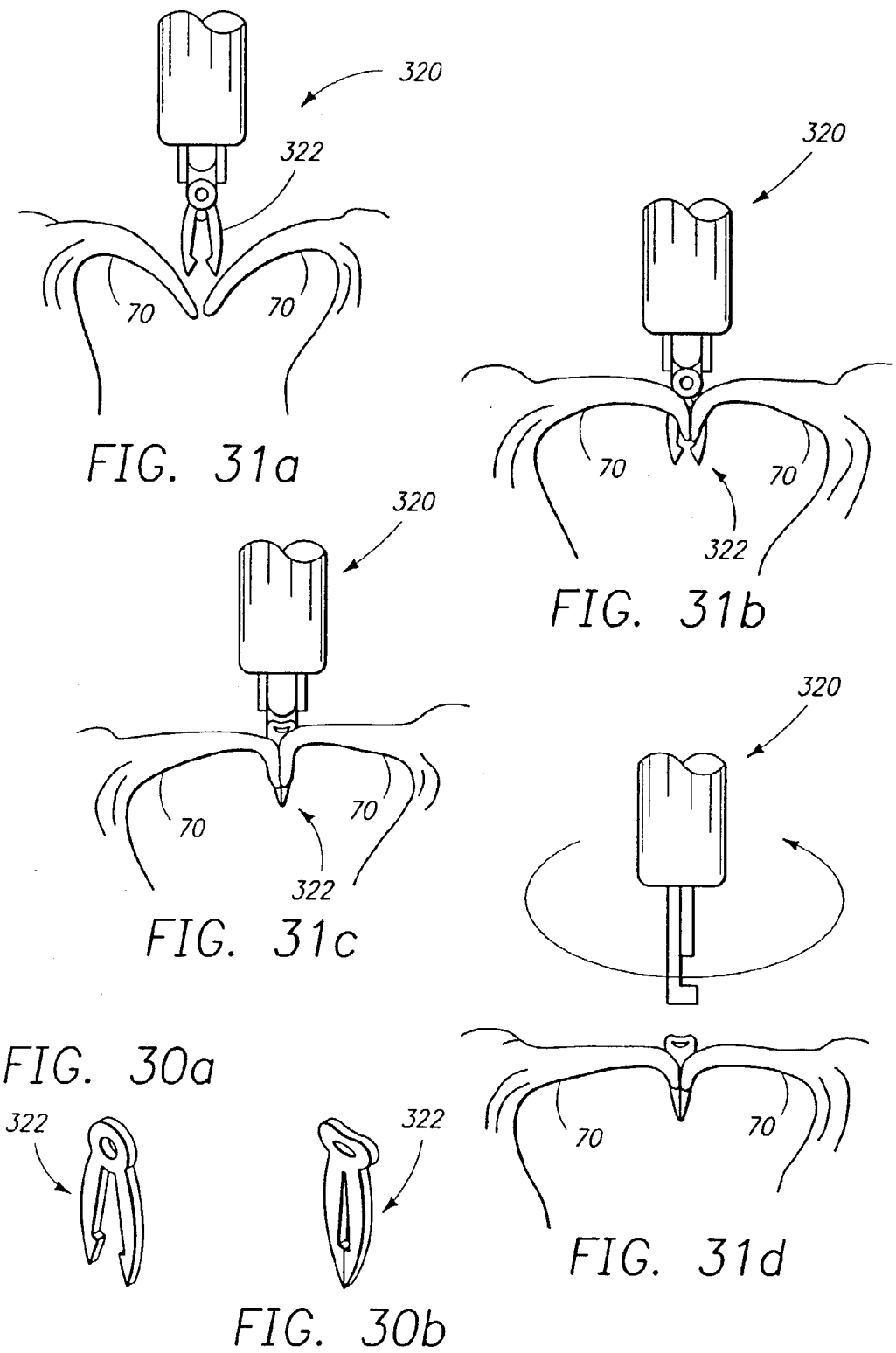

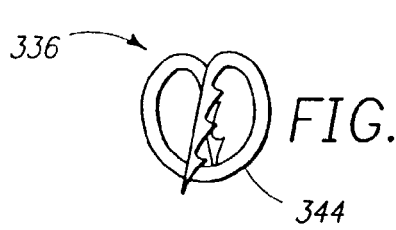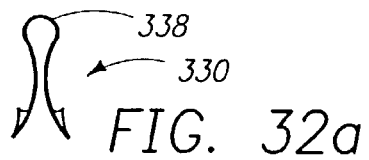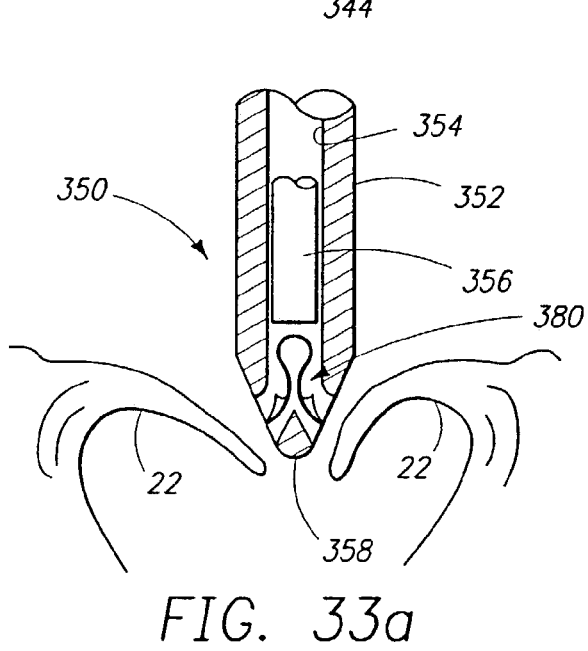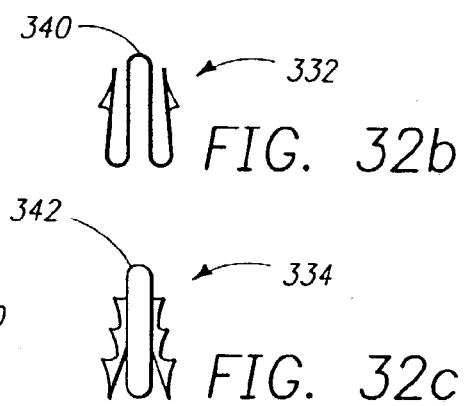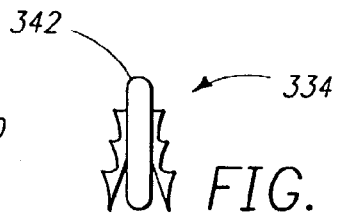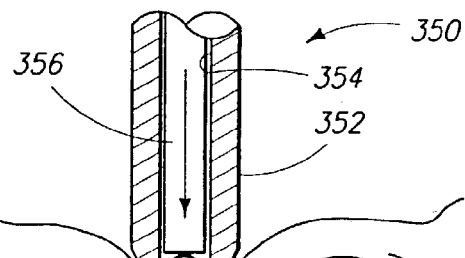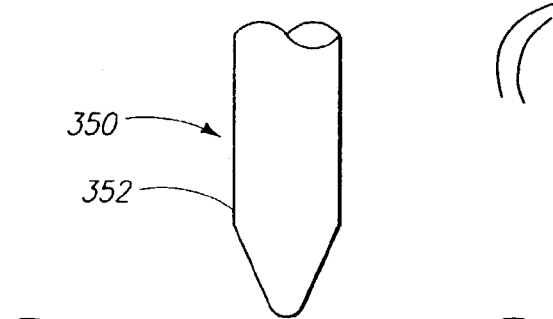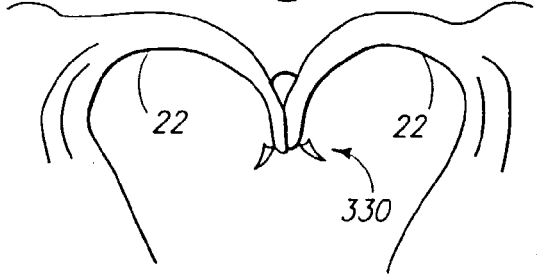

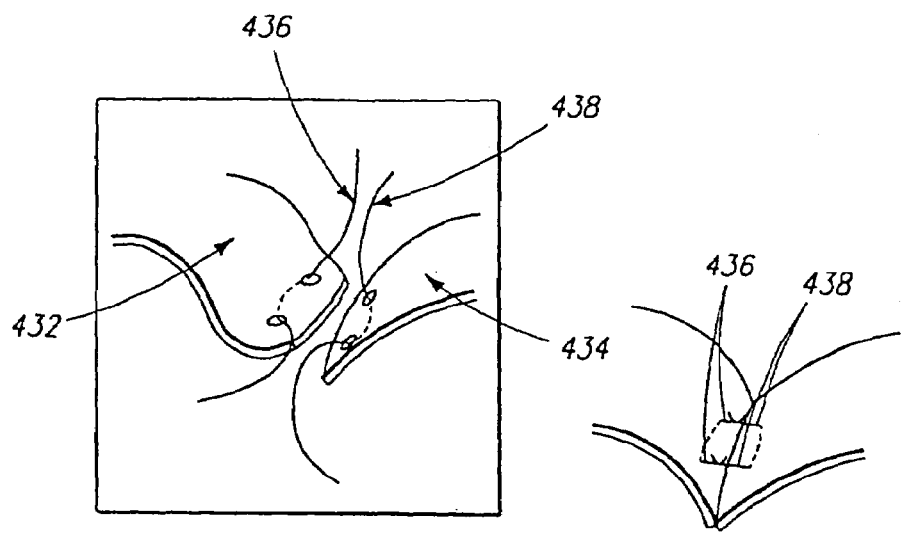
FIG. 45a
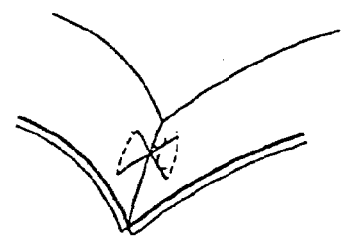
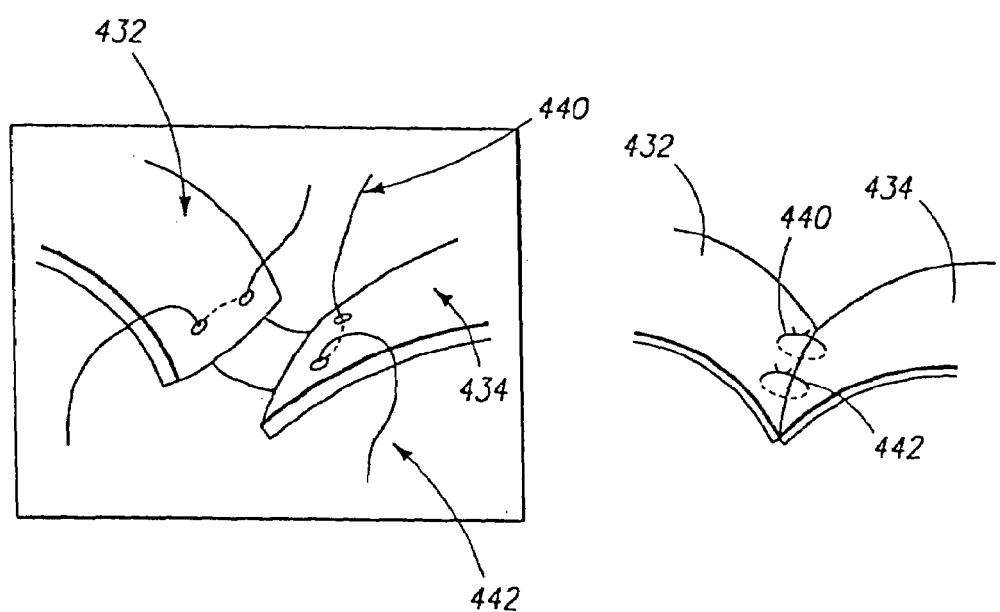
FIG. 45b

MINIMALLY INVASIVE MITRAL VALVE REPAIR METHOD AND APPARATUS

CROSS REFERENCE TO A RELATED PATENT APPLICATION

The present application is a continuation of U.S. application Ser. No. 09/562,406, filed May 1, 2000 now U.S. Pat. No. 6,626,930, entitled Minimally Invasive Mitral Valve Repair Method and Apparatus, which claimed priority under 35 U.S.C. §119(e) from U.S. Provisional Patent Application No. 60/161,296, filed Oct. 21, 1999, entitled "Minimally Invasive Mitral Valve Repair Method And Apparatus". The disclosure of both the Parent and Provisional patent application are incorporated by reference herein in its entirety.

FIELD OF THE INVENTION

The present invention relates to the repair of heart valves, and, more particularly, to methods and apparatuses for the repair of heart valves by fastening the valve leaflets together at their coapting edges.

BACKGROUND OF THE INVENTION

In vertebrate animals, the heart is a hollow muscular organ having four pumping chambers: the left and right atria and the left and right ventricles, each provided with its own one-way outflow valve. The natural heart valves are identified as the aortic, mitral (or bicuspid), tricuspid and pulmonary valves. The valves separate the chambers of the heart, and are each mounted in an annulus therebetween. The annuluses comprise dense fibrous rings attached either directly or indirectly to the atrial and ventricular muscle fibers. The leaflets are flexible collagenous structures that are attached to and extend inward from the annuluses to meet at coapting edges. The aortic and tricuspid valves have three leaflets, while the mitral and pulmonary valves have two.

Various problems can develop with heart valves, for a number of clinical reasons. Stenosis in heart valves is a condition in which the valves do not open properly. Insufficiency is a condition which a valve does not close properly. Repair or replacement of the aortic or mitral valves are most common because they reside in the left side of the heart where pressures and stresses are the greatest. In a valve replacement operation, the damaged leaflets are excised and the annulus sculpted to receive a replacement prosthetic valve.

In many patients who suffer from valve dysfunction, surgical repair (i.e., "valvuloplasty") is a desirable alternative to valve replacement. Remodeling of the valve annulus (i.e., "annuloplasty") is central to many reconstructive valvuloplasty procedures. Remodeling of the valve annulus is typically accomplished by implantation of a prosthetic ring (i.e. "annuloplasty ring") to stabilize the annulus and to correct or prevent valvular insufficiency that may result from a dysfunction of the valve annulus. Annuloplasty rings are typically constructed of a resilient core covered with a fabric sewing ring. Annuloplasty procedures are performed not only to repair damaged or diseased annuli, but also in conjunction with other procedures, such as leaflet repair.

Mitral valve regurgitation is caused by dysfunction of the mitral valve structure, or direct injury to the mitral valve leaflets. A less than perfect understanding of the disease process leading to mitral valve regurgitation complicates selection of the appropriate repair technique. Though implantation of an annuloplasty ring, typically around the posterior aspect of the mitral valve, has proven successful in a number of cases, shaping the surrounding annulus does not always lead to optimum coaptation of the leaflets.

More recently, a technique known as a "bow-tie" repair has been advocated. The bow-tie technique involves suturing the anterior and posterior leaflets together in the middle, causing blood to flow through the two side openings thus formed. This process was originally developed by Dr. Ottavio Alfieri, and involved placing the patient on extracorporeal bypass in order to access and suture the mitral valve leaflets.

A method for performing the bow-tie technique without the need for bypass has been proposed by Dr. Mehmet Oz, of Columbia University. The method and a device for performing the method are disclosed in PCT publication WO 99/00059, dated Jan. 7, 1999. In one embodiment, the device consists of a forceps-like grasper device that can be passed through a sealed aperture in the apex of the left ventricle. The two mitral valve leaflets meet and curve into the left ventricular cavity at their mating edges, and are thus easy to grasp from inside the ventricle. The mating leaflet edges are grasped from the ventricular side and held together, and various devices such as staples are utilized to fasten them together. The teeth of the grasper device are linearly slidable with respect to one another so as to align the mitral valve leaflets prior to fastening. As the procedure is done on a beating heart, and the pressures and motions within the left ventricle are severe, the procedure is thus rendered fairly skill-intensive.

There is presently a need for an improved means for performing the bow-tie technique of mitral valve repair.

SUMMARY OF THE INVENTION

The present invention provides a number of devices and methods for fastening or "approximating" tissue pieces together. The term "tissue pieces" is to be understood to mean discrete pieces that may be straight, curved, tubular, etc., so long as the pieces are initially disconnected. For example, many of the embodiments of the invention disclosed herein are especially useful for joining two leaflets of a heart valve. The coapting edges of the leaflets thus constitute the "tissue pieces." In other contexts, the invention can be used to anastomose two vessels, either end-to-end, in a T-junction, or otherwise. In these cases, the two vessels define the "tissue pieces." One specific application of using the invention to perform an anastomosis is in a coronary artery bypass graft (CABG) procedure. Another example of an application of the present invention is in wound closure, wherein the facing edges of the wound are joined. In sum, the present invention in its broadest sense should not be construed to be limited to any particular tissue pieces, although particular examples may be shown and disclosed.

The present invention includes a number of devices and method for both stabilizing the tissue pieces to be joined, and fastening them together. Some embodiments disclose only the stabilizing function, others only the fastening function, and still other show combination stabilizing and fastening devices. It should be understood that certain of the stabilizing devices can be used with certain of the fastening devices, even though they are not explicitly shown in joint operation. In other words, based on the explanation of the particular device, one of skill in the art should have little trouble combining the features of certain of two such devices. Therefore, it should be understood that many of the stabilizing and fastening devices are interchangeable, and the invention covers all permutations thereof.

Furthermore, many of the fastening devices disclosed herein can be deployed separately from many of the stabilizing devices, and the two can therefore be deployed in parallel. Alternatively, and desirably, however, the fastening and stabilizing functions are performed with one device.

The stabilizing and fastening devices of the present invention can be utilized in either standard open surgical procedures, endoscopic procedures, or percutaneous procedures. In one embodiment the devices can be delivered through an open chest either transapically or transatrially. In another embodiment, the stabilizing and fastening devices can be introduced through an incision performed over the roof of the left atrium. In yet another embodiment the devices can be delivered into the left ventricle through the right chest via a thorascope. The devices can also be delivered percutaneously, via a catheter or catheters, into the patient's arterial system (e.g. through the femoral or brachial arteries). Other objects, features, and advantages of the present invention will become apparent from a consideration of the following detailed description.

BRIEF DESCRIPTION OF THE DRAWINGS

FIG. 1 is a perspective view of an exemplary tissue stabilizer of the present invention that uses a vacuum;

FIG. 1a is an elevational view of a first step in a valve repair procedure using the tissue stabilizer of FIG. 1;

FIG. 1b is an elevational view of a second step in a valve repair procedure using the tissue stabilizer of FIG. 1;

FIG. 2 is a perspective view of a further tissue stabilizer of the present invention that also uses a vacuum;

FIG. 2a is an elevational view of a step in a valve repair procedure using the tissue stabilizer of FIG. 2;

FIG. 4b is an elevational view of a second step in a valve repair procedure using the tissue stabilizer of FIG. 4a;

FIGS. 6a–6c are elevational views of several steps in a valve repair procedure using a tissue stabilizer of the present invention and the suture-based tissue fastener shown in FIG. 5a.

FIG. 7a is a perspective view of an exemplary tissue stabilizing and fastening device of the present invention that uses a vacuum and needles to deliver suture-based fasteners having toggles through the tissue;

FIG. 7b is an elevational view of a step in a valve repair procedure using the tissue stabilizing and fastening device of FIG. 7a;

FIG. 8 is an elevational view of an alternative tissue stabilizing and fastening device similar to that shown in FIG. 7a;

FIG. 9b is a plan view of the distal tip of the device of FIG. 9a;

FIG. 13b is a plan view of the distal tip of the device of FIG. 13a;

FIGS. 16e and 16f are isolated views of suture ties used with the suture-based fastener of FIG. 16a;

FIG. 18b is a detailed perspective view of a second step in a valve repair procedure using the spiral suture-based leaflet fastener of FIG. 18a;

FIG. 18c is an elevational view of a completed valve repair procedure utilizing the spiral suture-based leaflet fastener of FIG. 18a;

FIG. 18d is a detailed view of a pledget anchoring device used with the spiral suture-based leaflet fastener of FIG. 18a;

FIG. 25a is a perspective view of an exemplary tissue staple useful with the methods and devices of the present invention and shown in an open configuration;

FIG. 25b is a perspective view of the tissue staple of FIG. 25a shown in a closed configuration;

FIGS. 26a–26c are elevational views of several steps in a valve repair procedure using an exemplary tissue fastening device of the present invention for delivering the tissue staple of FIG. 25a;

FIG. 27a is a perspective view of a further tissue stabilizing and fastening device of the present invention that uses a vacuum and delivers a staple to fasten tissue pieces;

FIG. 27b is a sectional view of a step in a valve repair procedure using the tissue stabilizing and fastening device of FIG. 27a;

FIG. 27c is a perspective view of a completed valve repair procedure utilizing the tissue stabilizing and fastening device of FIG. 27a;

FIG. 28a is an elevational view of a further tissue fastening device of the present invention for delivering an alternative "toggle-like" tissue clip, the clip shown open;

FIG. 28b is an elevational view of the tissue fastening device of FIG. 28a, the clip shown closed;

FIG. 29a is a detailed perspective view of a first step in a valve repair procedure using the tissue fastening device of FIG. 28a;

FIGS. 29b and 29c are elevational views of two steps in a valve repair procedure using the tissue fastening device of FIG. 28a;

FIG. 30a is a perspective view of an alternative "toggle-like" tissue fastening clip, the clip shown open;

FIG. 30b is a perspective view of the tissue fastening clip of FIG. 30a shown closed;

FIGS. 31a–31d are elevational views of several steps in a valve repair procedure using an exemplary tissue fastening device of the present invention for delivering the tissue fastening clip of FIG. 30a;

FIGS. 32a–32d are elevational views of various tissue fastening clips having barbed ends;

FIGS. 33a and 33b are sectional views of a two steps in a valve repair procedure using an exemplary tissue fastening device of the present invention for delivering a barbed tissue fastening clip of FIG. 32a;

FIG. 33c is an elevational view of a third step in a valve repair procedure using the tissue fastening device of FIG. 33a;

FIG. 35a is a sectional view of a tissue fastening device for delivering the tissue fastener of FIG. 34a;

FIG. 37a is a sectional view of a tissue fastening device for delivering the tissue fastener of FIG. 36a;

FIG. 37b is a sectional view of the tissue fastener of FIG. 36a in a closed position around the tissue being connected;

FIGS. 45a and 45b illustrate perspective views of alternate suture configurations used to practice the invention.

DESCRIPTION OF THE PREFERRED EMBODIMENTS

Exemplary Stabilizing Devices

Figure 3A:
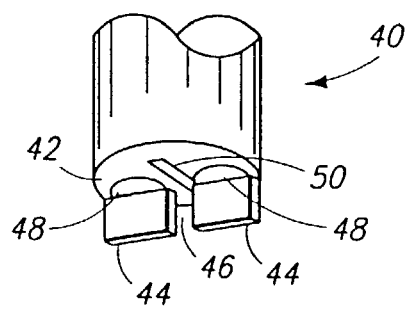
FIGS. 3a–3c are perspective views of several embodiments of vacuum-based tissue stabilizers having tissue separating walls.

FIG. 1 shows a tissue stabilizer 20 of the present invention that uses a vacuum to hold two tissue pieces. In this case, the tissue pieces are heart valve leaflets 22 and a valve repair procedure using the stabilizer 20 is depicted in FIGS. 1a and 1b. The tissue stabilizer 20 comprises a cylindrical probe 24 with at least one internal lumen (not shown) and having a flat distal end 26, a pair of vacuum ports 28 being disposed in the distal end 26. The ports 28 may be in communication with a common vacuum source, may be separately communicable with the source with internal valves (not shown), or may be in communication with different vacuum sources. The size of the ports 28 and magnitude of suction applied may vary depending on the application, but the ports 28 are desirably spaced apart a minimum distance to create two distinct suctions. In this manner, one leaflet or the other may be stabilized with one of the ports 28 without unduly influencing the other. In one example, the ports 28 have a minimum diameter of about ⅛ inch, and are spaced apart with a wall of at least 0.020 inches therebetween.

The probe 24 desirably has a size suitable for minimally invasive surgery. In one embodiment probe 24 is part of a catheter based percutaneous delivery system. In that case probe 24 is a catheter tube having a lumen or lumens connecting vacuum ports 28 to the vacuum source or sources. The catheter would be long enough and have sufficient steerability and maneuverability to reach the heart valve from a peripheral insertion site, such as the femoral or brachial artery. One particular advantage of the present invention is the ability to perform valve repair surgery on a beating heart. The procedure shown in FIGS. 1a and 1b is a mitral valve repair with an approach of the probe 24 from the left atrium 30. The atrium 30 has lower pressures than the ventricle 31, and thus there is less blood leakage and less turbulence imparted to the probe 24. First, the anatomical structures, including the location of the leaflets 22, can be visualized using echo technology, or other means. One leaflet 22 may be stabilized with one of the ports 28, and that leaflet 22 then manipulated toward the other leaflet 22, which is then also stabilized. Again, any of the fasteners disclosed herein may then be used to secure the leaflets 22 together.

FIG. 2 is illustrates another tissue stabilizer 32 similar to that shown in FIG. 1 and that also uses a vacuum. The tissue stabilizer 32 includes a probe body 34 having at least one internal lumen (not shown) and an angled or tapered nose 36 on a distal end. A vacuum port 38 is provided on each face of the tapered nose 36. FIG. 2a shows a valve repair procedure using the tissue stabilizer 32 of FIG. 2, wherein a distal tip 40 of the nose 36 is exposed to the ventricular 31 side of the leaflets 22. Because of this exposure, various leaflet fastening devices can be delivered through the probe 34 to the ventricular side of the leaflets 22, as will be seen below.

Figure 3B:
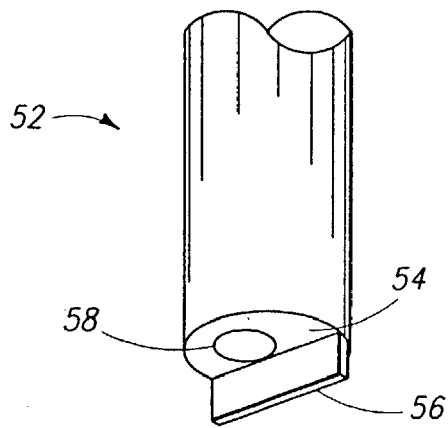
Figure 3C:
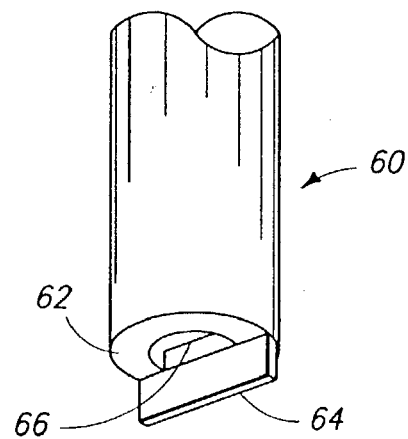

FIGS. 3a–3c show three vacuum-based tissue stabilizers having tissue separating walls. In FIG. 3a, a tissue stabilizer 40 includes a flat distal face 42 having a pair of distally-directed tissue separating walls 44 extending therefrom, and defining a gap 46 therebetween. The stabilizer 40 contains one or more lumens in communication with vacuum ports 48 that open on both sides of the walls 44. There are four such ports 48 shown, one on each side of each wall 44. In addition, a fastener channel 50 opens at the distal face 42 between the walls 44, and facing the gap 46 therebetween. The fastener channel 50 can be used to deliver tissue fasteners, as described below.

In FIG. 3b, a tissue stabilizer 52 includes a flat distal face 54 having a single distally-directed tissue separating wall 56 extending therefrom. The stabilizer 52 contains one or more lumens in communication with circular vacuum ports 58 that open on both sides of the wall 56. There are two such ports 58 shown, one on each side of each wall 56.

In FIG. 3c, a tissue stabilizer 60 includes a flat distal face 62 having a single distally-directed tissue separating wall 64 extending therefrom. The stabilizer 60 contains one or more lumens in communication with semi-circular vacuum ports 66 that open on both sides of the wall 64. There are two such ports 66 shown, one on each side of each wall 64.

Figure 3D:
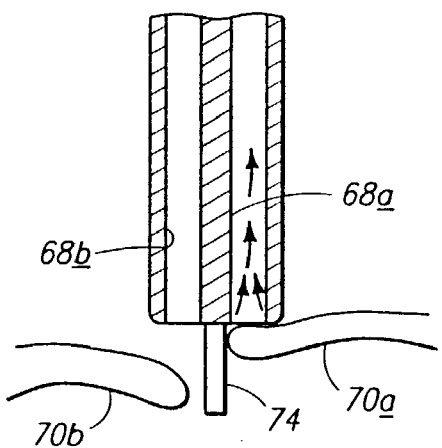
FIGS. 3d and 3e are sectional views of two different vacuum port configurations for the tissue stabilizers shown in FIGS. 3a–3c, the stabilizers shown in operation.
Figure 3E:
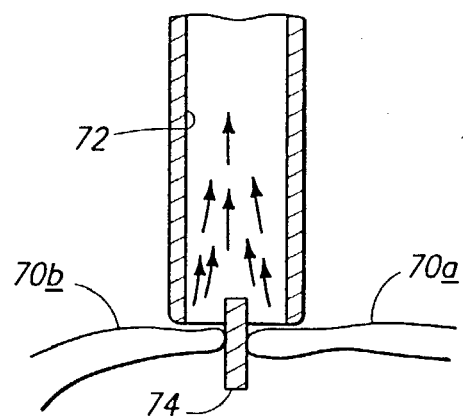

FIGS. 3d and 3e show two different vacuum port configurations for the tissue stabilizers 40, 52, or 60 shown in FIGS. 3a–3c. As mentioned above, the stabilizers 40, 52, or 60 may have one or more lumens in communication with one or more ports. In FIG. 3d, two lumens 68a and 68b provide separate suction control to the associated ports. Thus, one tissue piece 70a is seen stabilized by the right-hand vacuum port, while the left-hand port is not operated. Alternatively, a single lumen 72 in communication with two vacuum ports is seen in FIG. 3e, and both tissue pieces 70a, 70b are stabilized simultaneously. In both these views, the tissue separating wall 74 is shown between the tissue pieces to be joined. Fastening devices can thus be delivered via the wall 74, or through a gap formed for that purpose, such as the gap 46 and fastener channel 50 seen in FIG. 3a.

Figure 4A:
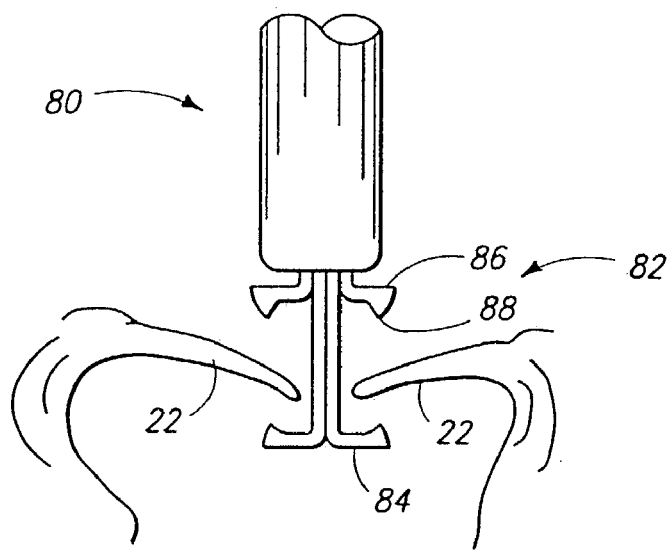
FIG. 4a is an elevational view of a first step in a valve repair procedure using a mechanical tissue stabilizer with linearly displaceable tissue clamps.
Figure 4C:
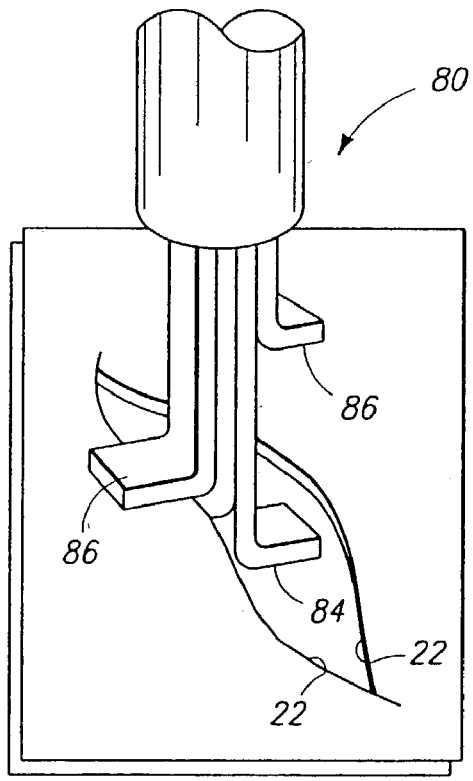
FIG. 4c is a detailed perspective view of a clamp of the tissue stabilizer of FIG. 4a extended to grasp a valve leaflet from both sides.
Figure 4B:
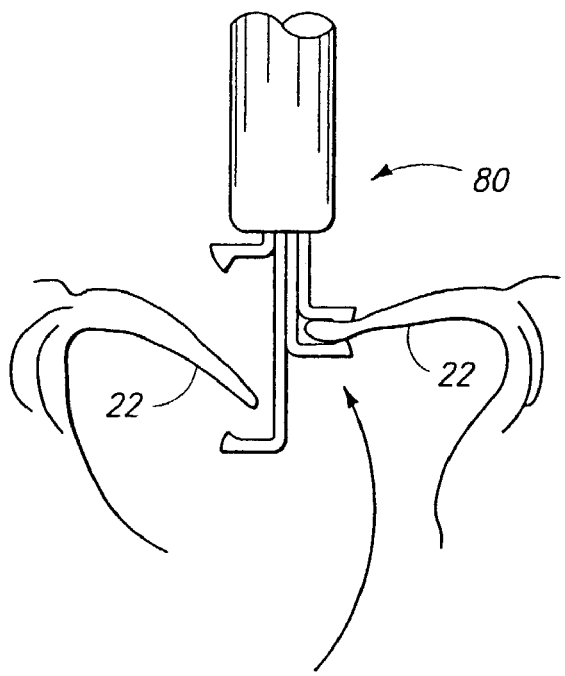

FIGS. 4a–4c show a mechanical tissue stabilizer 80 with a four-part, linearly displaceable tissue clamp 82. On each side, a lower clamp 84 is separated from an upper clamp 86 and inserted between two tissue pieces (in this case valve leaflets 22). As the lower and upper clamps 84, 86 are brought together, as seen in FIG. 4b, they physically clamp and stabilize the leaflet 22. Small teeth 88 on the clamps 84, 86 may be provided for traction. The clamps 84 and 86 on each side are individually actuated to enable grasping of one leaflet 22 at a time.

Exemplary Suture-Based Tissue Fasteners

Figures 5A, 5B:
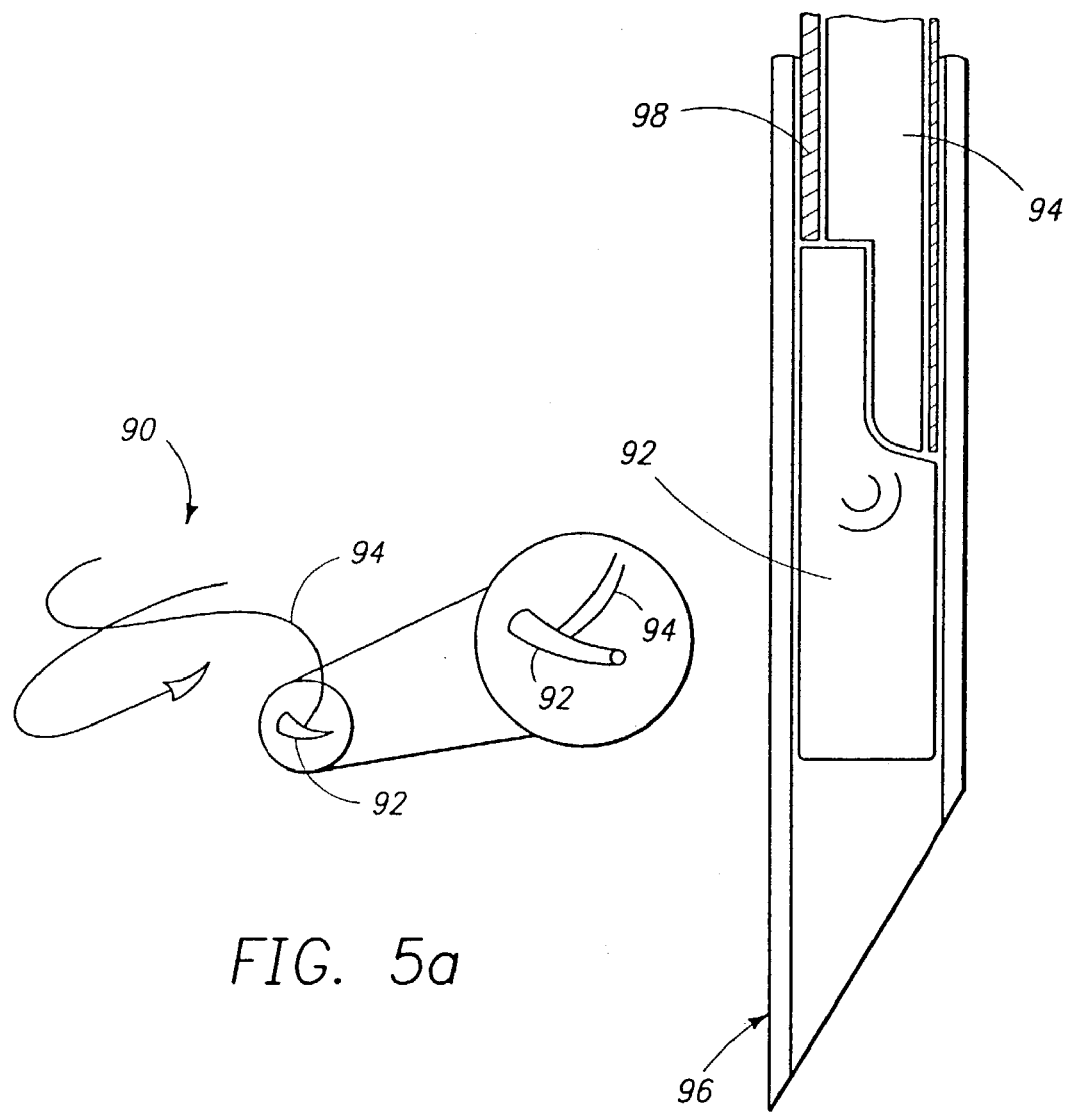
FIG. 5a is a perspective view of a suture-based tissue fastener of the present invention having toggles.
FIG. 5b is a sectional view of the suture-based tissue fastener of FIG. 5a loaded into a delivery needle.

FIG. 5a illustrates a suture-based tissue fastener 90 of the present invention including toggles 92 secured to the end of suture threads 94. FIG. 5b is a sectional view through a needle 96 used to deliver the tissue fastener 90. Specifically, the toggle 92 and suture thread 94 is seen loaded into the lumen of the needle 96, and a pusher 98 is provided to urge the tissue fastener 90 from the distal end thereof.

Figure 6A:
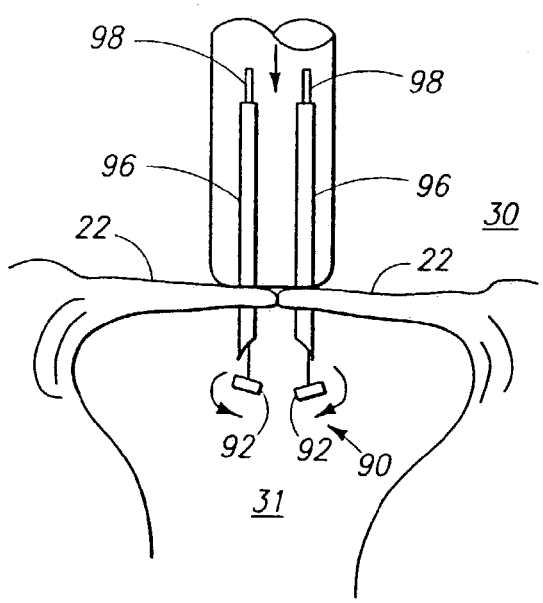
Figure 6B:
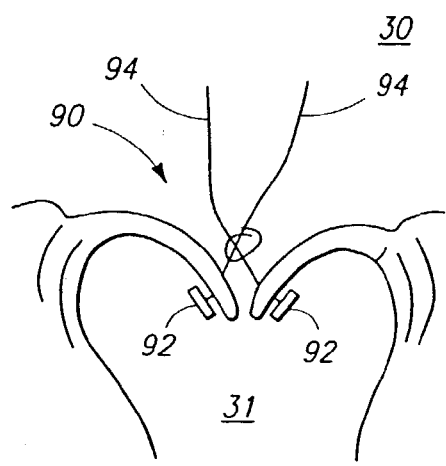
Figure 6C:
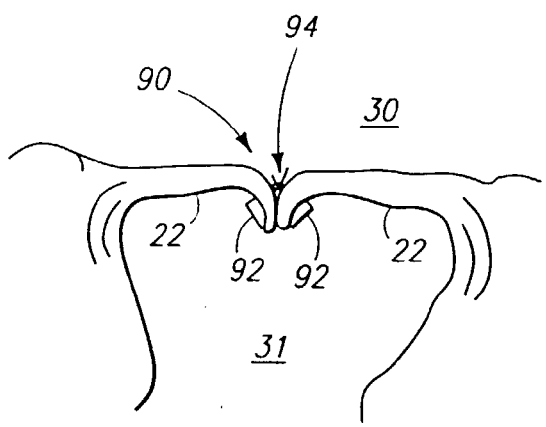

FIGS. 6a–6c depict several steps in a valve repair procedure using the tissue fasteners 90 shown in FIG. 5a. A probe, such as the probe 20 seen in FIG. 1 having vacuum ports for tissue stabilization, provides lumens for two of the needles 96 of FIG. 5b. The lumens with the vacuum parts 96 may receive the needles 96 or additional lumens may be provided. The sharp ends of the needles 96 pierce the leaflets, and the pushers 98 are displaced (separately or in conjunction) to deploy the tissue fasteners 90. After the needles 96 are retracted, the toggles 92 anchor the tissue fasteners 90 on the ventricular 31 side of the leaflets 22. The suture threads 94 are then tied off on the atrial 30 side to secure the leaflets 22 together, as seen in FIG. 6c.

FIG. 7a is a perspective view of an exemplary tissue stabilizing and fastening device 100 that uses the principles of vacuum stabilization and a suture-based toggle fastener, as seen in FIGS. 5a and 5b. The device 100 includes a probe 102 defining several lumens (not shown) therein that open on a distal face. Two lumens 104 open at a proximal end and receive two of the needles 96 for delivering the fasteners. Two other lumens communicate through two side arms 106 with sources of vacuum. FIG. 7b shows the device 100 in use in a valve repair procedure, with the two needles 96 having pierced the leaflets 22 and delivered the fasteners 90. The leaflets 22 are held to the probe 102 using the vacuum ports.

FIG. 8 illustrates an alternative tissue stabilizing and fastening device 108 similar to the device 100 of FIG. 7a, but having a pointed nose with two concave faces 110 in which the vacuum ports are located. The device 108 functions as described above, with a fastener deliver needle shown in phantom having pierced the left leaflet 22.

Figure 9A:
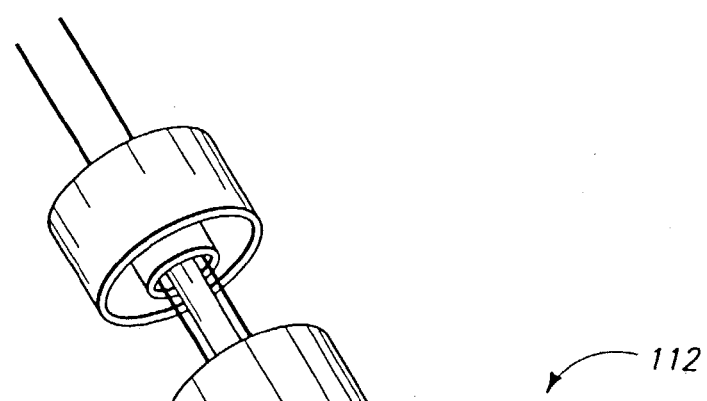
FIG. 9a is a perspective view of a further tissue stabilizing and fastening device of the present invention that uses a vacuum and needles to deliver suture-based fasteners having toggles through the tissue.
Figure 9B:
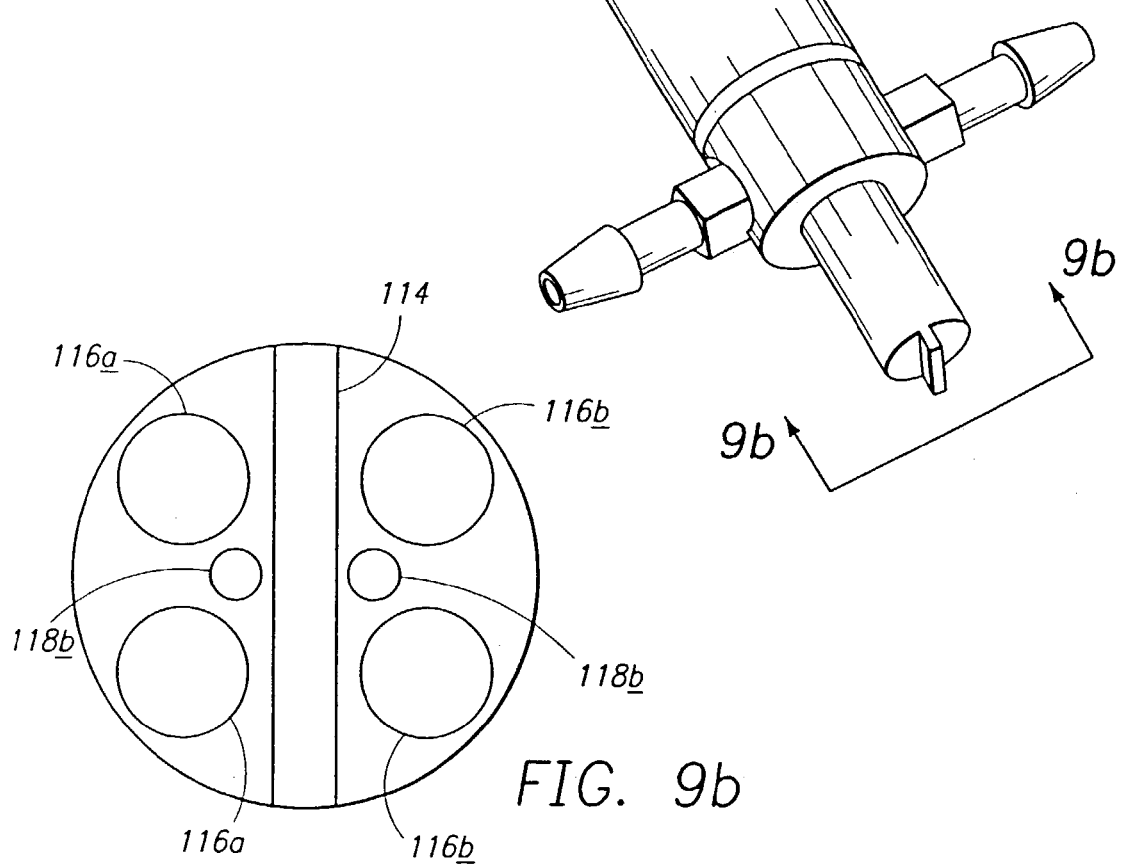

FIGS. 9a and 9b show a still further tissue stabilizing and fastening device 112 that uses a vacuum and needles to deliver suture-based fasteners having toggles through the tissue. The device 112 is quite similar in function to the device 102 of FIG. 7a, but has a modified distal end, as best seen in the plan view of FIG. 9b. Specifically, a central tissue separating wall 114 is provided with a pair of vacuum ports 116a on one side, and another pair 116b on the other. Again, the port 116 may be separately or commonly supplied with vacuum. Fastener delivery lumens 118a and 118b are located on each side of the wall. The aforementioned needles 96 or other such device may be delivered through the lumens 118 to pierce and fasten the tissue pieces.

Figure 10A:
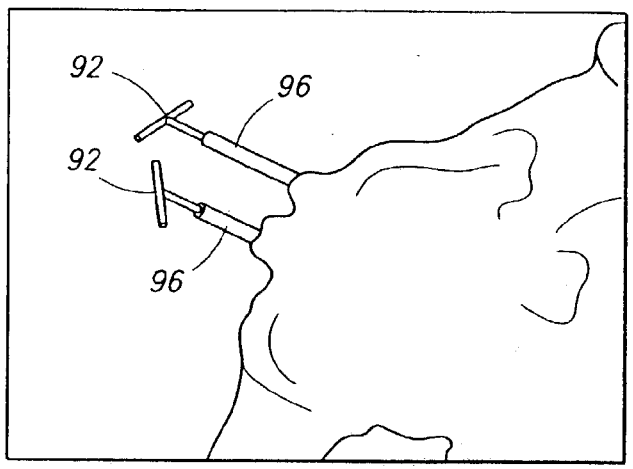
FIGS. 10a–10c are several photographs of tissue being connected with suture-based fasteners having toggles.
Figure 10B:
Figure 10C:
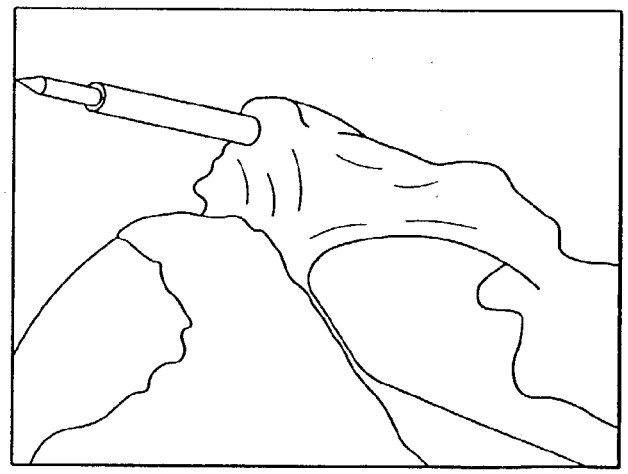

FIGS. 10a–10c are several photographs of tissue being connected with suture-based fasteners having toggles. FIG. 10a illustrates the toggle 92 being deployed. FIG. 10b illustrates the needles 96 being retracted, and FIG. 10c illustrates the sutures 94 being tied.

Figure 11A:
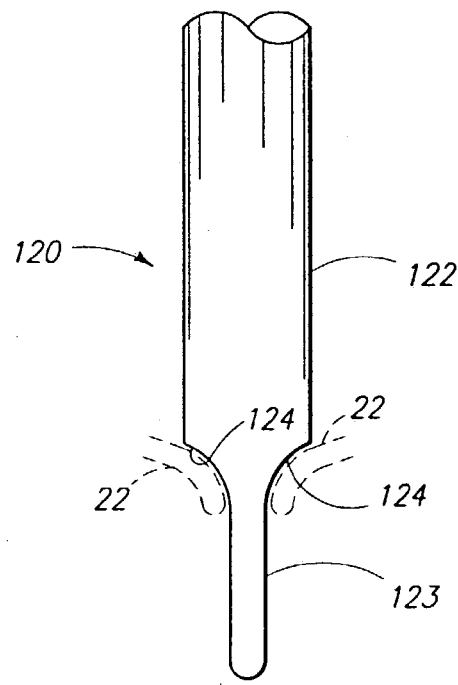
FIGS. 11a–11c are elevational views of a tissue stabilizing and fastening device of the present invention having members deployable on a blind side of the tissue being connected.
Figure 11B:
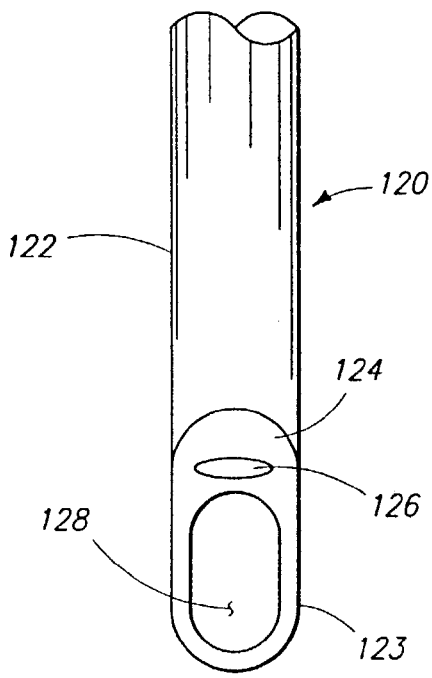
Figure 11C:
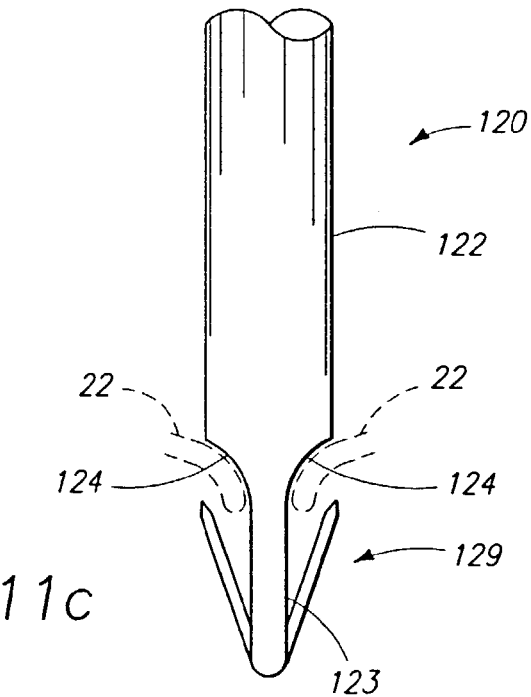

FIGS. 11a–11c show a tissue stabilizing and/or fastening device 120 having members deployable on a blind side of the tissue being connected. In this context, "blind side" means the side of the tissue pieces opposite the side to which the device has direct access. The deployable members may be clamps to stabilize the tissue pieces, or fastening devices that contact the tissue pieces on the blind side.

The device 120 includes a probe 122 with lumens, and a distal tip 123 that is narrower than the probe 122 and defines concave transition faces 124. A vacuum port 126 may be provided in each transition face 124 for tissue stabilization, or a clamping mechanism may be stowed in a space 128 in the distal tip 123. FIG. 11c shows the clamp 129 (or fastener) in a deployed state.

Figure 12A:
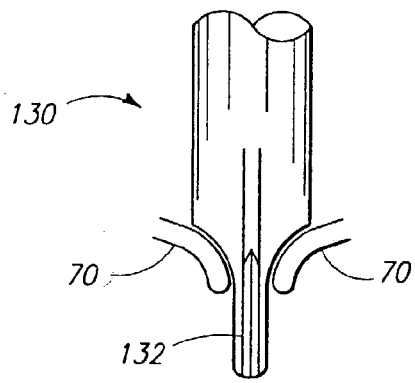
FIGS. 12a–12e are elevational views of a tissue stabilizing and fastening device of the present invention having needles deployable on a blind side of the tissue being connected and a suture-based fastener.
Figure 12B:
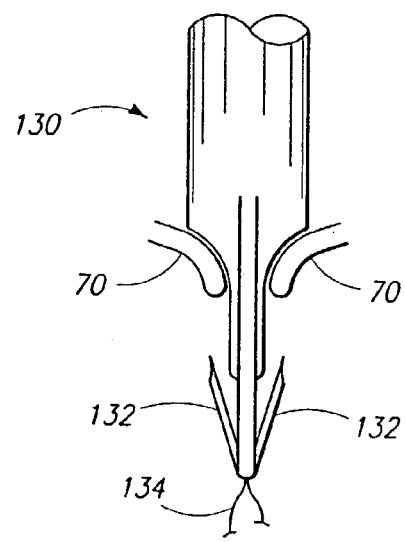
Figure 12C:
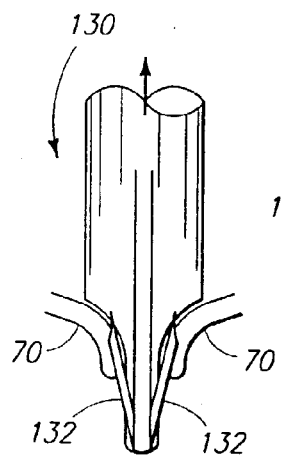
Figure 12D:
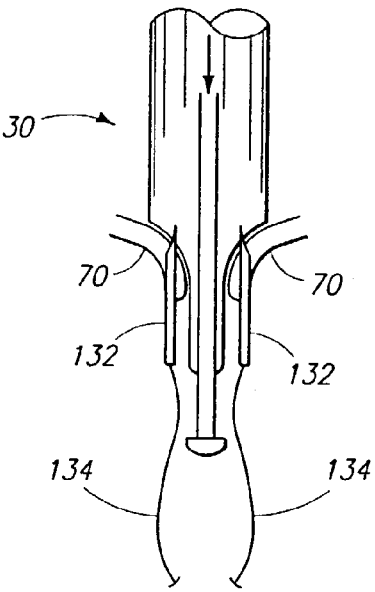
Figure 12E:
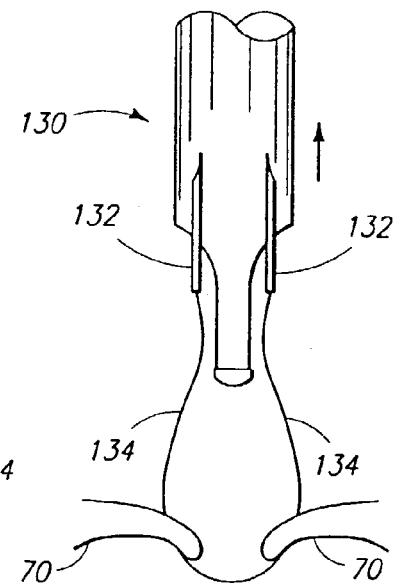

FIGS. 12a–12e illustrate a tissue stabilizing and fastening device 130 having needles 132 deployable on a blind side of the tissue being connected. The device 130 may be configured like the device 120 of FIG. 11a, with the space 128 receiving needles 132. A common suture thread 134 connects the needles 132 and is used to secure the tissue pieces 70 together. Thus, as seen in the sequence of FIGS. 12a–12e, the needles 132 are first advanced to the blind side of the tissue pieces 70 and deployed outboard of the distal tip. The entire device 130 is retracted, as in FIG. 12c, to cause the needles 132 to pierce the tissue pieces 70. The two needles 132 are then disengaged from the device 130, and each other, as in FIG. 12d, and the entire device 130 once again retracted to pull the needles 132 out from the pieces 70, leaving the connected suture joining the two pieces 70 (FIG. 12e). The suture 132 can then be tied off, or otherwise secured on the upper side of the tissue pieces 70.

Figure 13A:
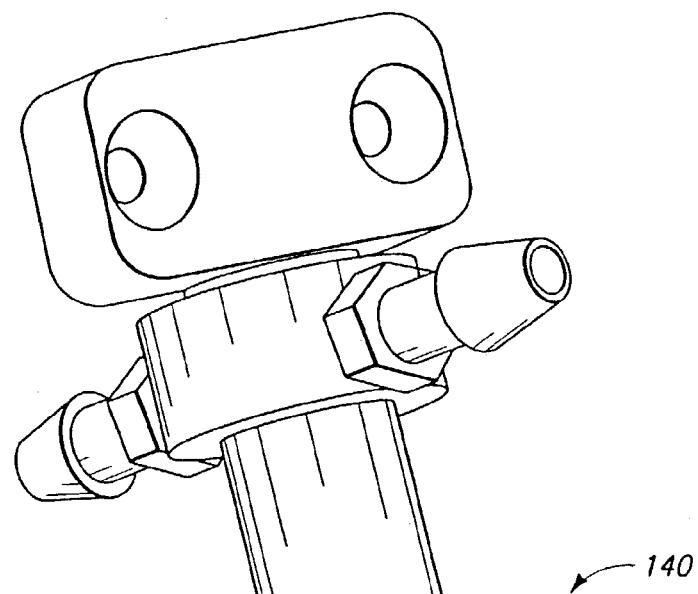
FIG. 13a is a perspective view of a further tissue stabilizing and fastening device of the present invention that uses a vacuum and deployable needles to deliver suture-based fasteners through the tissue.
Figure 13B:
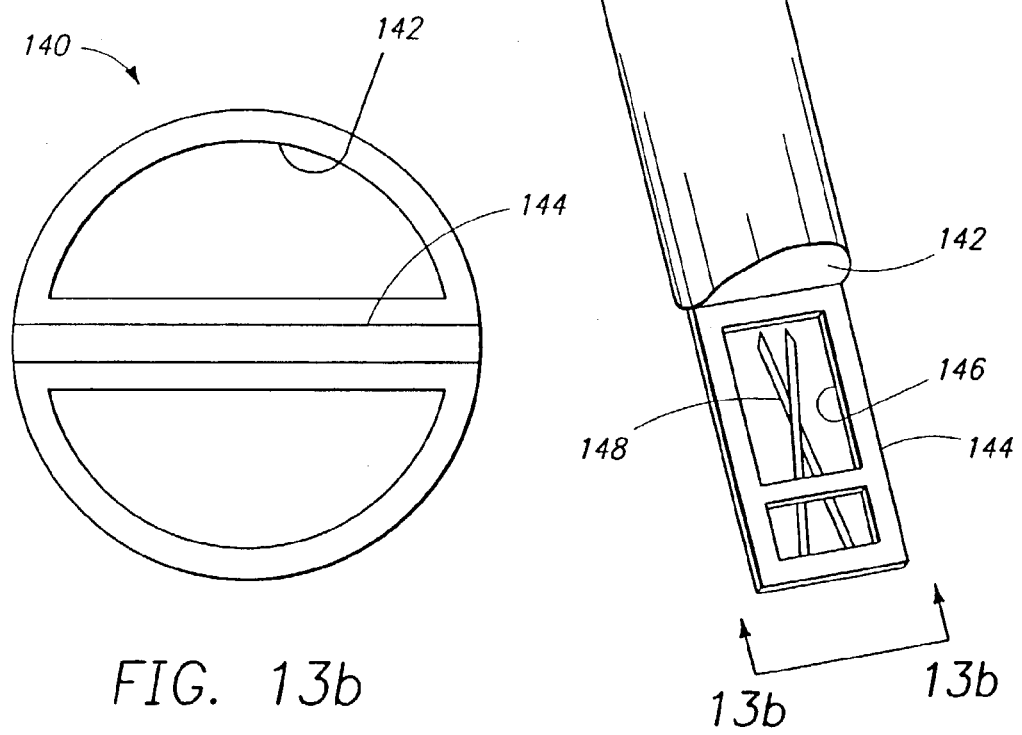

FIG. 13a is a more detailed view of a tissue stabilizing and fastening device 140 similar to that shown in FIGS. 12a–12e. The device 140 features two semi-circular vacuum ports 142 that stabilize the tissue pieces being joined. The distal tip includes a centered and distally-directed frame 144 defining a space 146 therein. The needles 148 are connected to the frame 144 and reside within the space 146. Although not shown, a deployment mechanism is also provided that causes the needles to pivot outward about their distal ends, and also disengages the needles 148 from the frame 144.

Figures 14A, 14B:
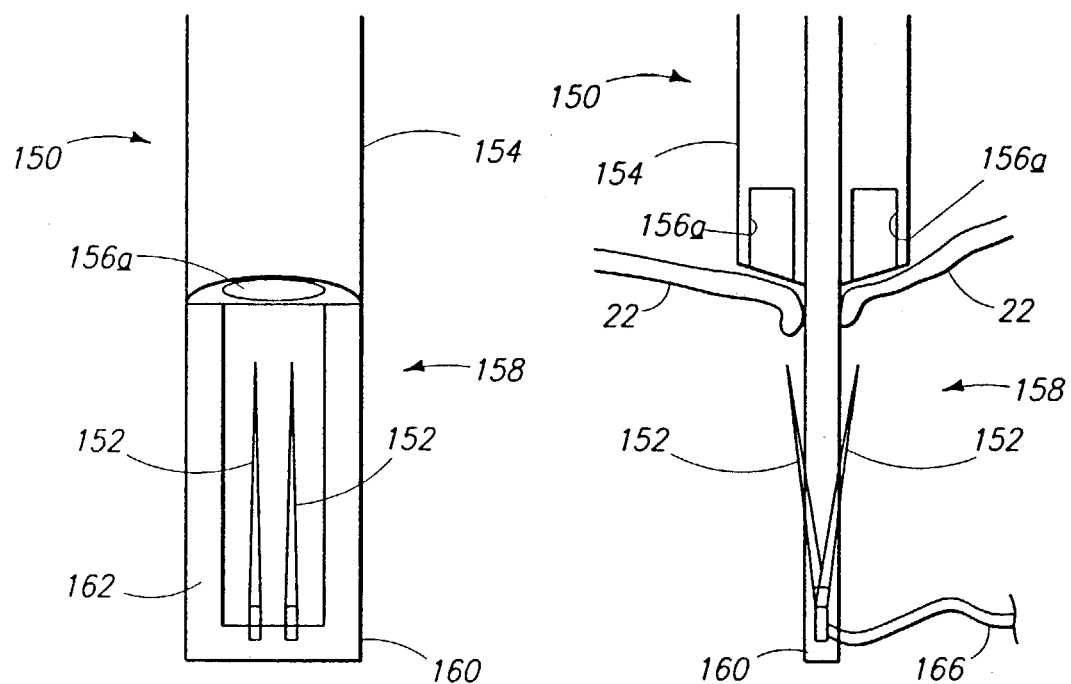
FIGS. 14a–14b are elevational view of a still further tissue stabilizing and fastening device of the present invention that uses vacuum and deployable needles to deliver suture-based fasteners through the tissue.

FIGS. 14a–14b illustrate a tissue stabilizing and fastening device 150 having needles 152 deployable on a blind side of the tissue being connected. The device 150 includes a probe 154 having two vacuum ports 156a, 156b for stabilizing the tissue pieces 70 being joined. A distal tip includes an extension member 158 having a centered and distally-directed frame 160 defining a space 162 therein. The extension member 158 may be configured relatively narrow in one direction such that it can enter the ventricle 31 between the leaflets 22 with minimum risk to the chordae (not shown). The frame 160 may be extended and retracted within the probe 154. The needles 152 are connected to the frame 160 and reside within the space 162. A deployment mechanism (not shown) is provided that causes the needles 152 to pivot outward about their distal end, and also disengages the needles 152 from the frame 160. A common suture thread 166, which is stored within the probe 154, connects the needles 152 and is used to secure the tissue pieces 70 together. In the embodiment shown in FIG. 14, the device 150 includes two needles 152 and a single suture 166. Other embodiments may include four needles with separate sutures. Additional needles may be provided if needed.

Figure 15A:
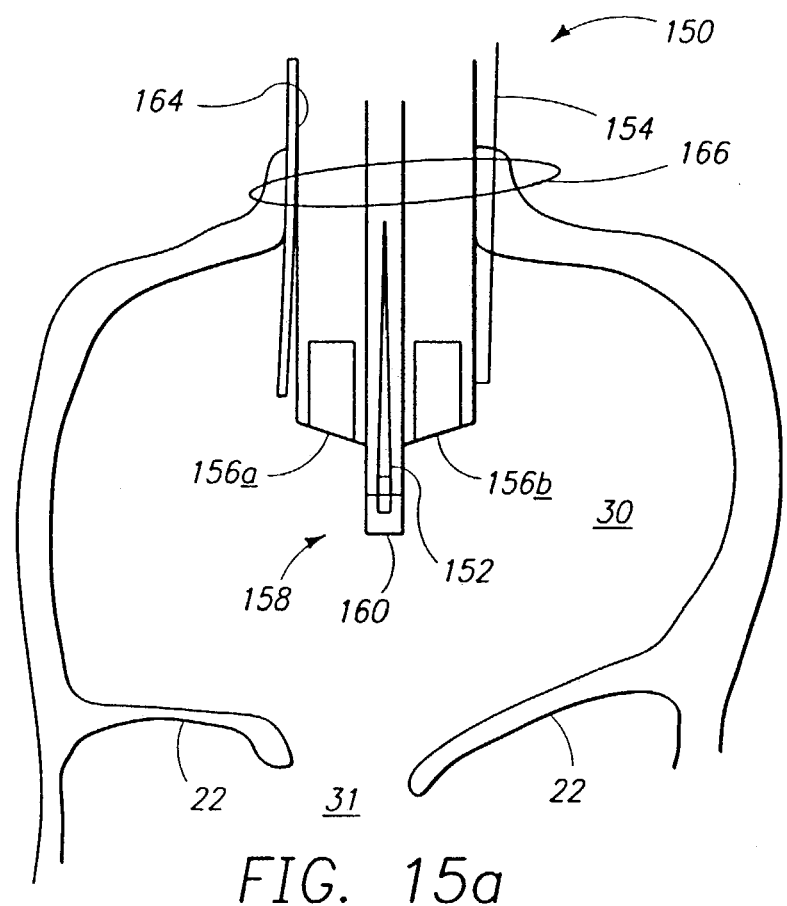
FIGS. 15a–15h are elevational and plan views of several steps in a valve repair procedure using the tissue stabilizing and fastening device of FIG. 14.
Figure 15B:
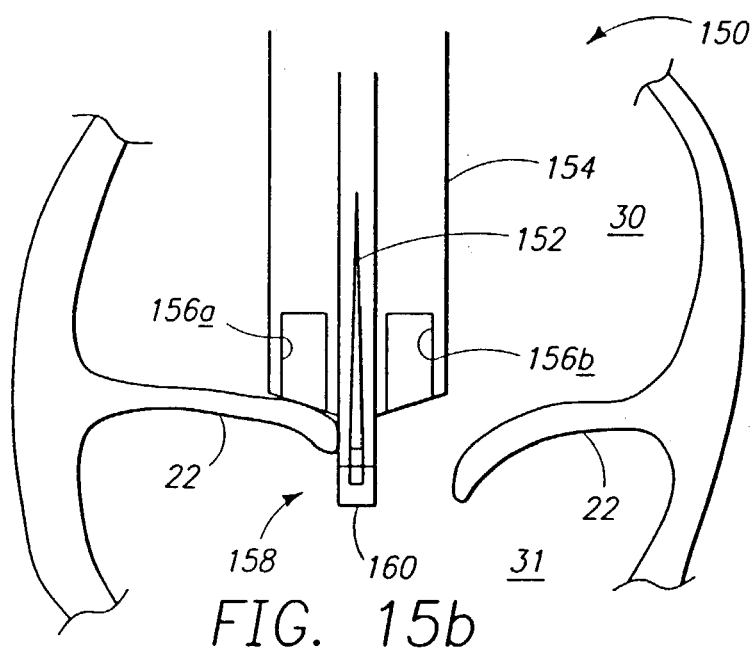
Figure 15C:
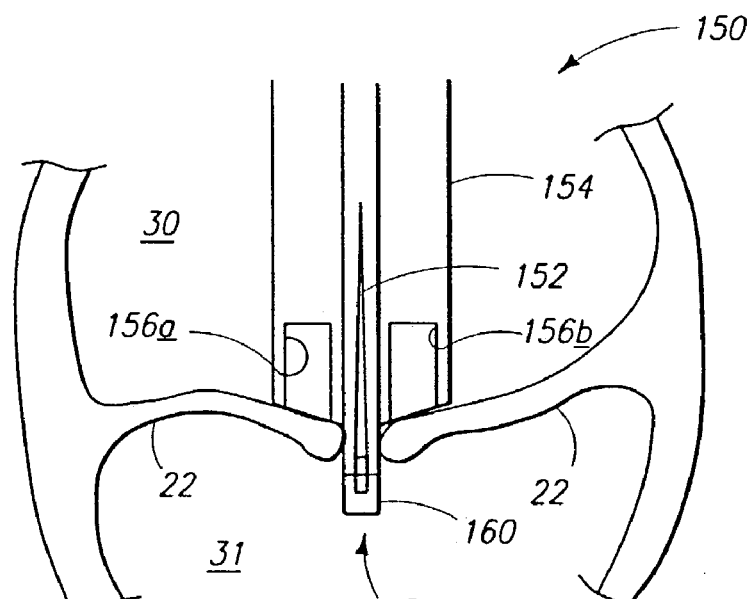
Figure 15D:
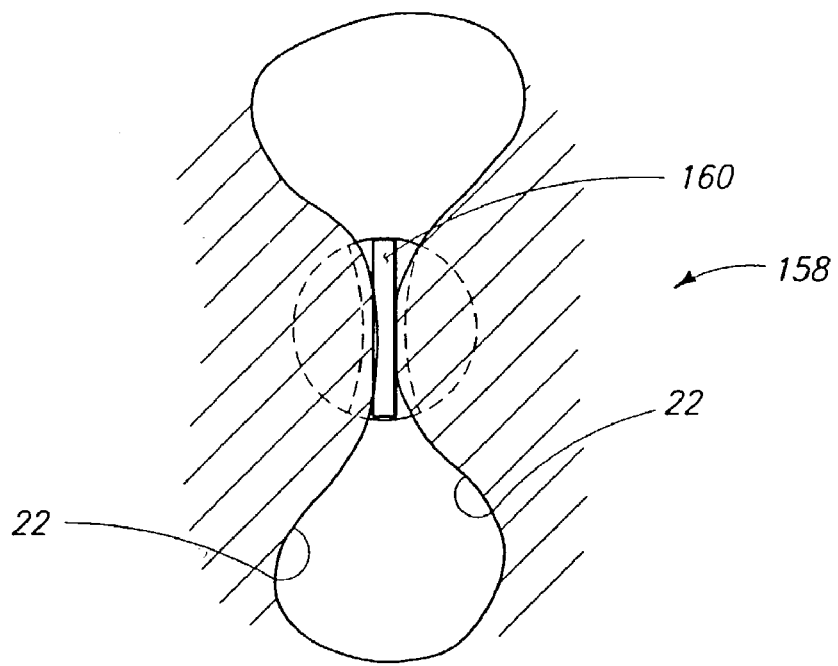
Figure 15E:
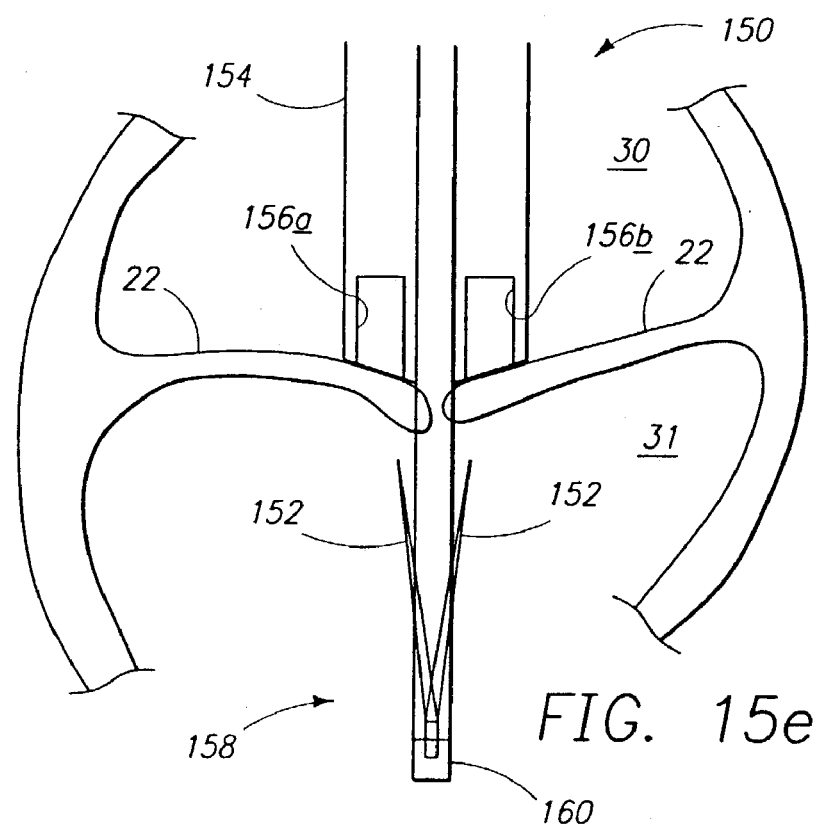
Figure 15F:
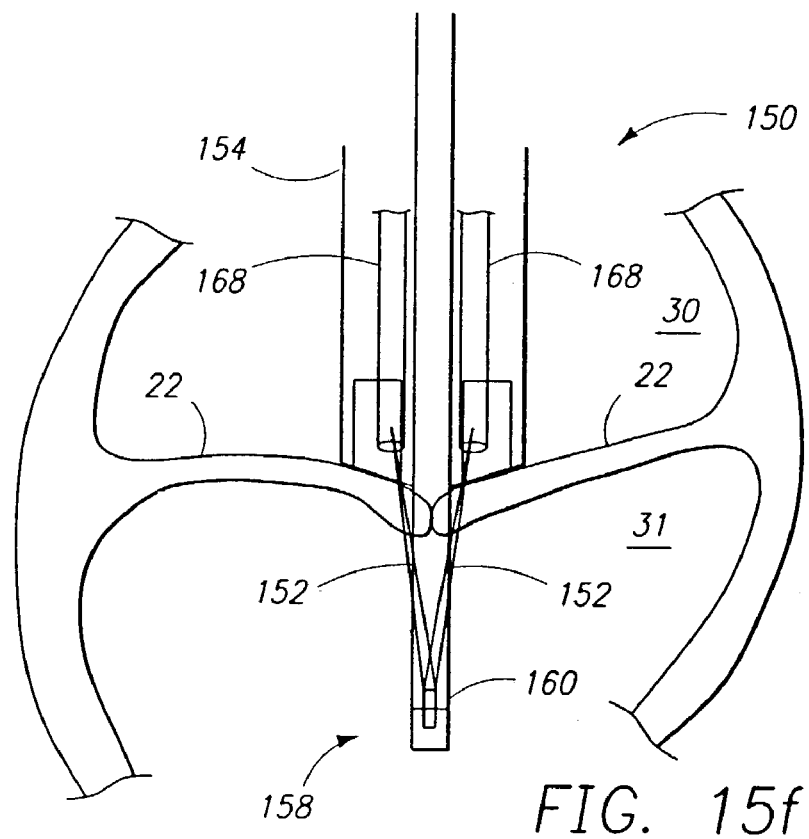
Figure 15G:
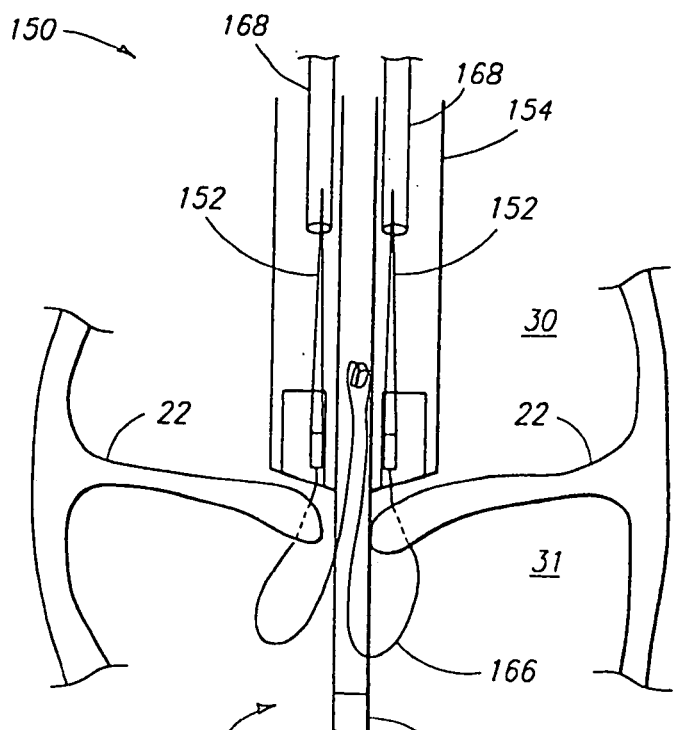
Figure 15H:
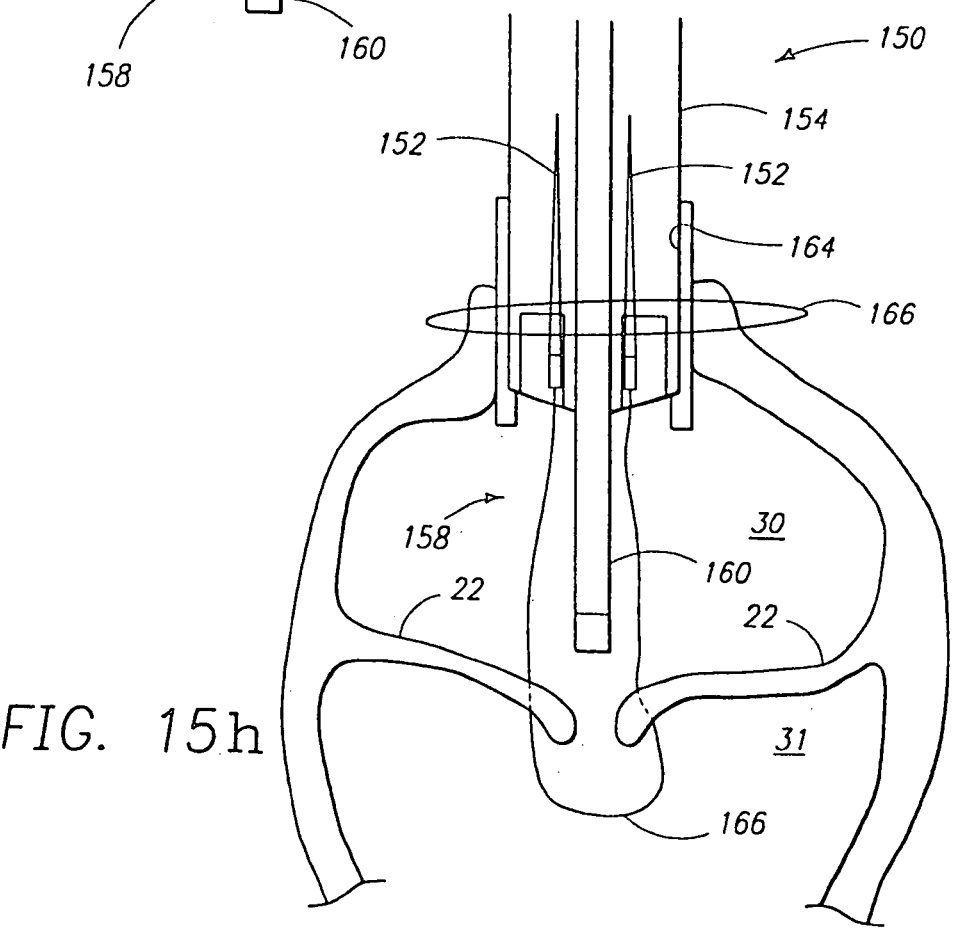

FIGS. 15a–15h illustrate several steps in a tissue joining procedure using the tissue stabilizing and fastening device 150. Referring to FIG. 15a, the probe 154 is passed through the atrium 30 via an access cannula or catheter 164. During this stage, the frame 160 is in its retracted position. The probe 154 is secured to the atrium 30 with a purse string 166 or any other manner known to one skilled in the art. FIGS. 15b–15d illustrate stabilization of the leaflets 22 being joined. Suction is provided to the first vacuum port 156a, and the probe 154 is manipulated to capture the first leaflet 22. With the first leaflet 22 captured, suction is provided to the second vacuum port 156b, and the second leaflet 22 is captured. Referring to FIG. 15e, the frame 160 is advanced into the ventrical 31 by extending the frame 160, and the needles 152 pivot outward about their distal end. The frame 160 is returned to its retracted position, and the needles 152 pierce the leaflets 22 and are directed into needle receivers 168, as shown in FIG. 15f. As shown in FIG. 15g, suction to the vacuum ports 156a, 156b is terminated, and the leaflets 22 are released. The needle receivers 168 pull the needles 152 through the leaflets 22, and the suture 166 "pays-out" behind the needles 152. The suture 166 trails out as the probe 154, with the needles 152 stored within the probe 154, is withdrawn from the access cannula or catheter 144 (see FIG. 15g). The two needles 152 are then disengaged from the probe 154, and the suture 166 can then be tied off, or otherwise secured on the upper side of the leaflets 22.

Figure 16A:
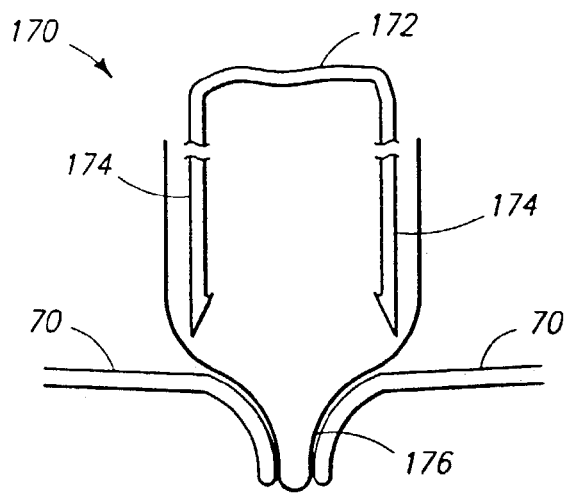
FIGS. 16a–16c are sectional views of several steps in a tissue joining procedure using an exemplary tissue stabilizing and fastening device having needles for delivering a suture-based fastener.
Figure 16B:
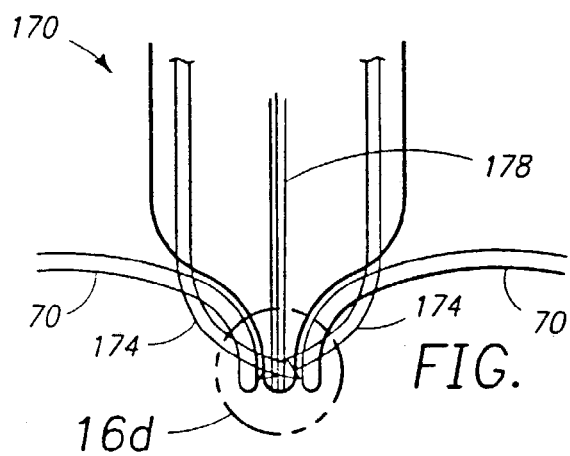
Figure 16C:
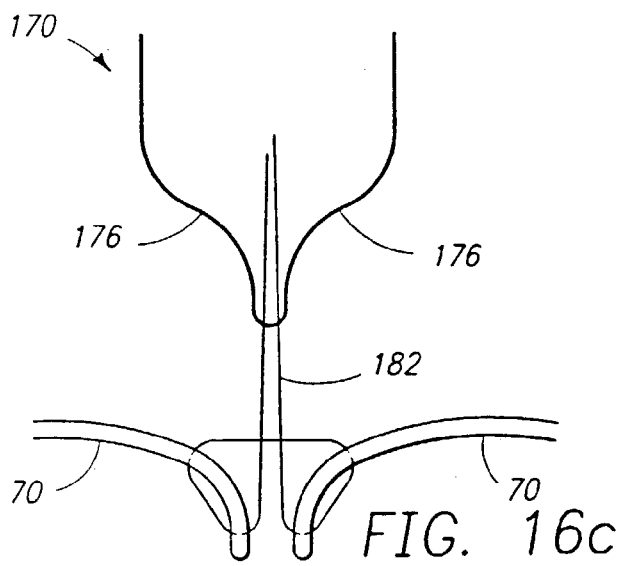

FIGS. 16a–16c are sectional views of several steps in a tissue joining procedure using a tissue stabilizing device 170 having a fastening device 172 with two needles 174 for delivering a suture-based fastener. The stabilizing device 170 includes a distal tip with oppositely-facing concave surfaces 176 for contacting and stabilizing the tissue pieces 70 (with, e.g., vacuum ports). Although not shown, the fastening device 172 is stowed in a channel within the stabilizing device 170 and may be linearly deployed through apertures formed in the concave surfaces 176.

Figure 16D:
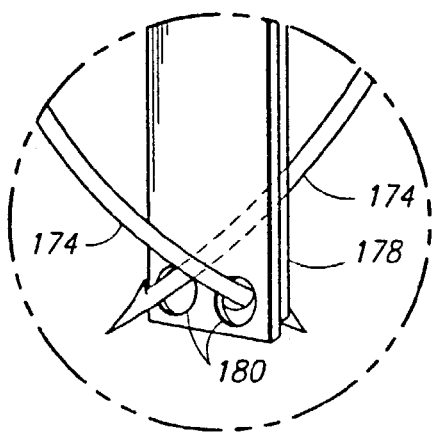
FIG. 16d is a detailed perspective view of a portion of the device seen in FIG. 16b.
Figure 16E:
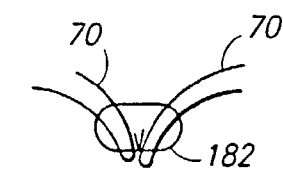
Figure 16F:
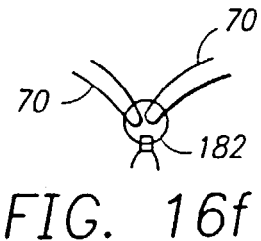

The device 170 further includes a sliding plate 178 with two throughholes 180 in the distal end, as seen in FIG. 16d. The fastening device 172 has a spring bias that causes the needles 174 to curve inward when permitted. Therefore, as seen in FIG. 16b, the fastening device 172 has been freed from the channels past the concave surfaces 176 and the needles 174 have curved inward to be received in the plate holes throughholes 180. The needles 174 first pass twice through each respective tissue piece 70. The plate 178 is then retracted upward into the device 1170, thus pulling the needles 174 through the tissue pieces 70. The fastening device 172 is desirably made of a highly pliable material, such as a superelastic like Nitinol, so that it can be pulled through sharp angles. Suture threads 182 are connected to each needle 174 and are also pulled through the tissue pieces 70. FIG. 16c shows the result, with the suture thread 182 passed through both tissue pieces 70. FIGS. 16e and 16f illustrate two suture ties to complete the procedure.

Figure 17A:
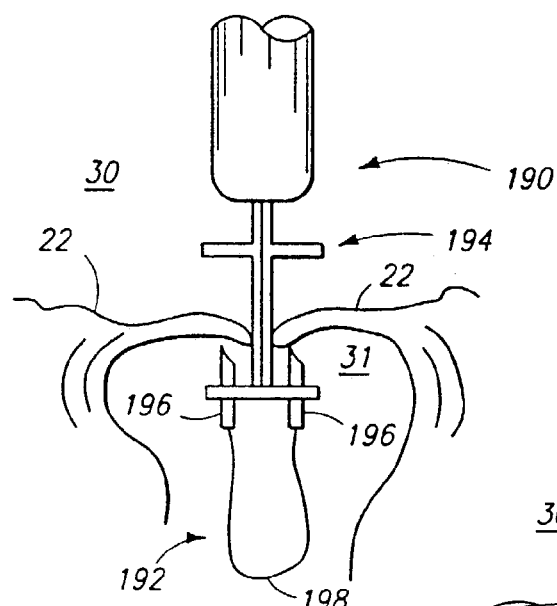
FIGS. 17a–17c are elevational views of several steps in a valve repair procedure using an exemplary tissue stabilizing and fastening device for delivering a suture-based axial needle fastener.
Figure 17B:
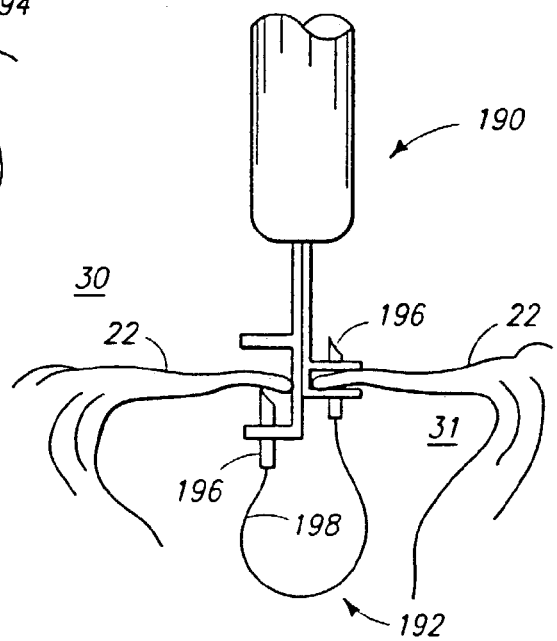
Figure 17C:
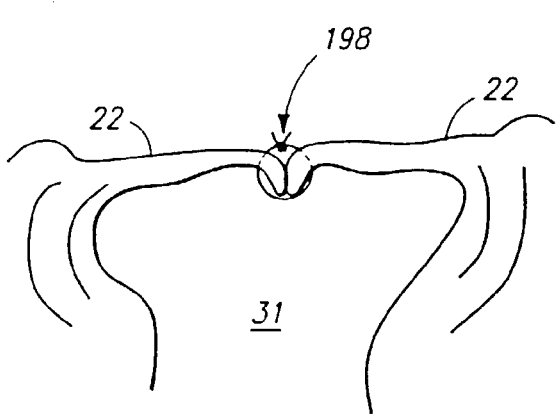

FIGS. 17a–17c illustrate several steps in a valve repair procedure using a tissue stabilizing and fastening device 190 for delivering a suture-based axial needle fastener 192. The device 190 includes a clamping mechanism 194, much like the clamping device 82 seen in FIGS. 4a–4c. The two sides are independently controllable, so as to grasp and pierce one leaflet 22 and then the other. The fastener 192 includes a pair of needles 196 initially mounted in the lower portion of the clamping mechanism 194 and facing upward. The two needles 196 are connected with a suture thread 198. When the clamping mechanism 194 actuates, the needles 198 pierce the respective leaflet 22. The upper portion of each side then pulls the needle 196 completely through the leaflet 22, and the lower portion is retracted from the blind side of the leaflets 22. The resulting suture loop is tied off, as seen in FIG. 17c.

Figure 18A:
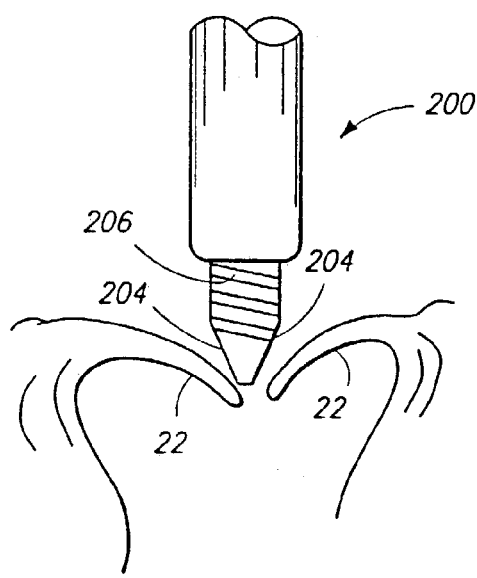
FIG. 18a is an elevational view of a first step in a valve repair procedure using an exemplary tissue fastening device of the present invention for delivering a spiral suture-based leaflet fastener.
Figure 18B:
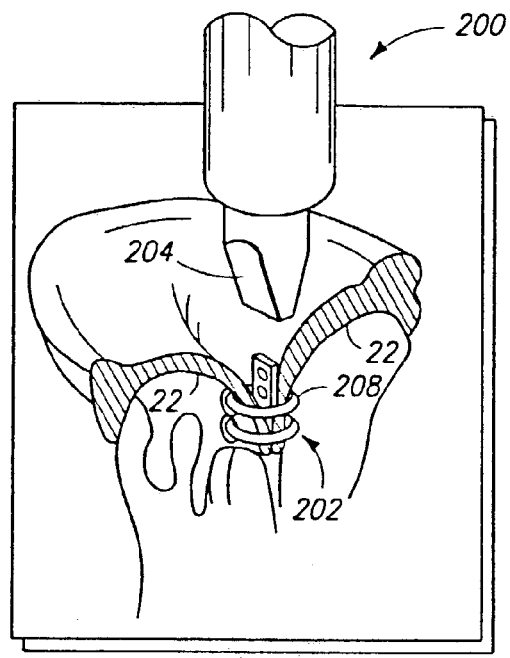
Figure 18C:
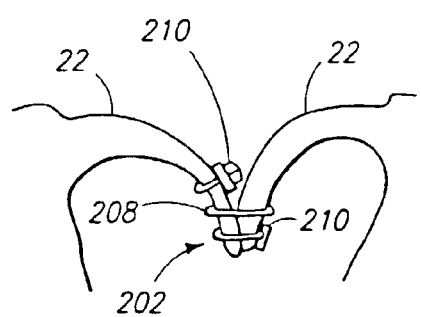
Figure 18D:
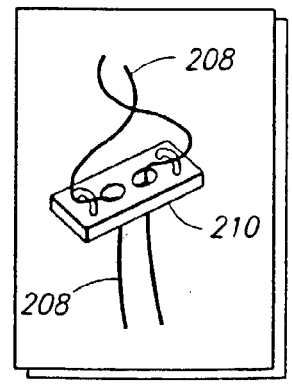
Figure 19A:
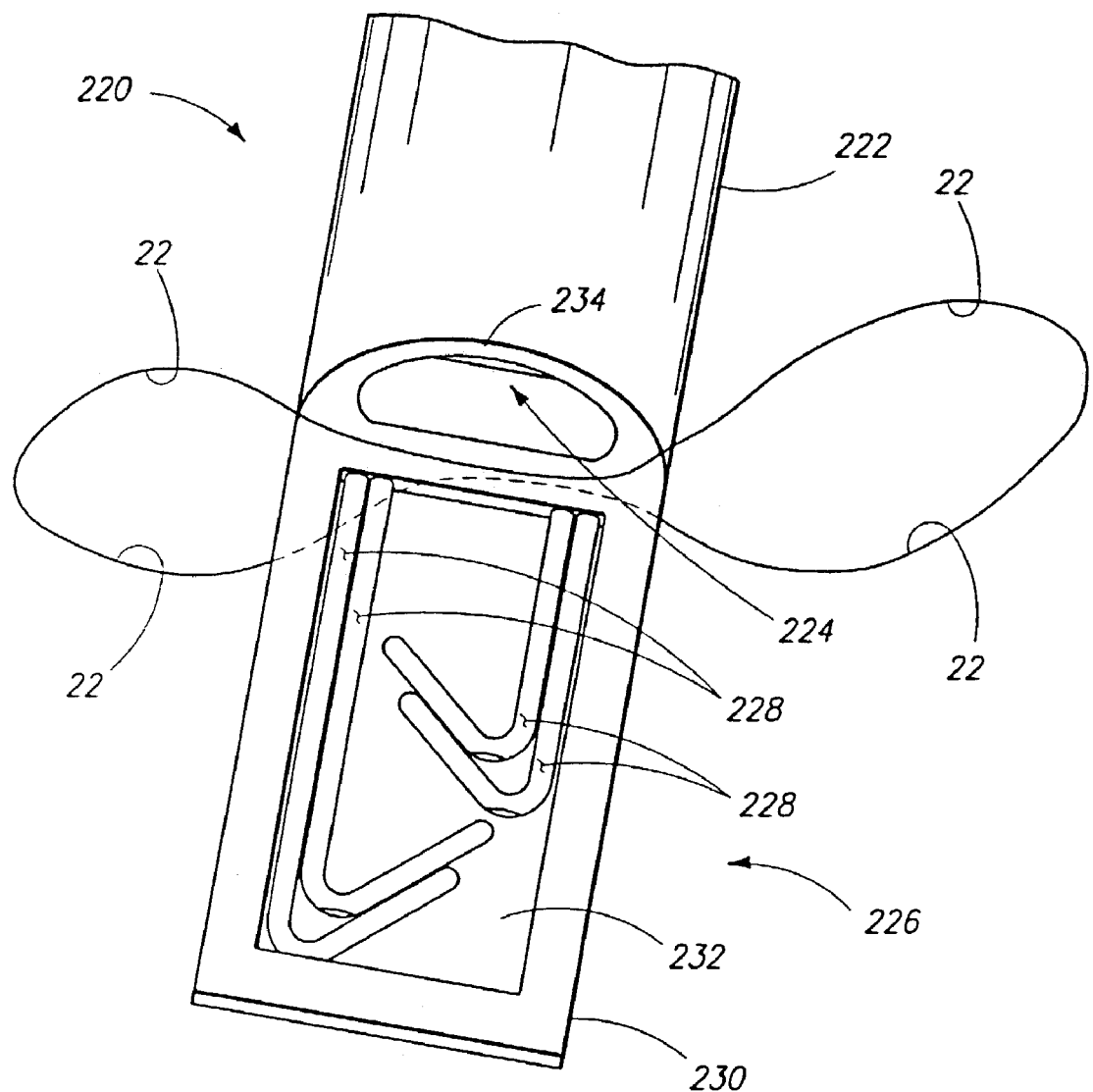
FIGS. 19a–19d are elevational views of several steps in a valve repair procedure using an exemplary tissue stabilizing and fastening device of the present invention having vacuum stabilization and mechanical clamping.
Figure 19B:
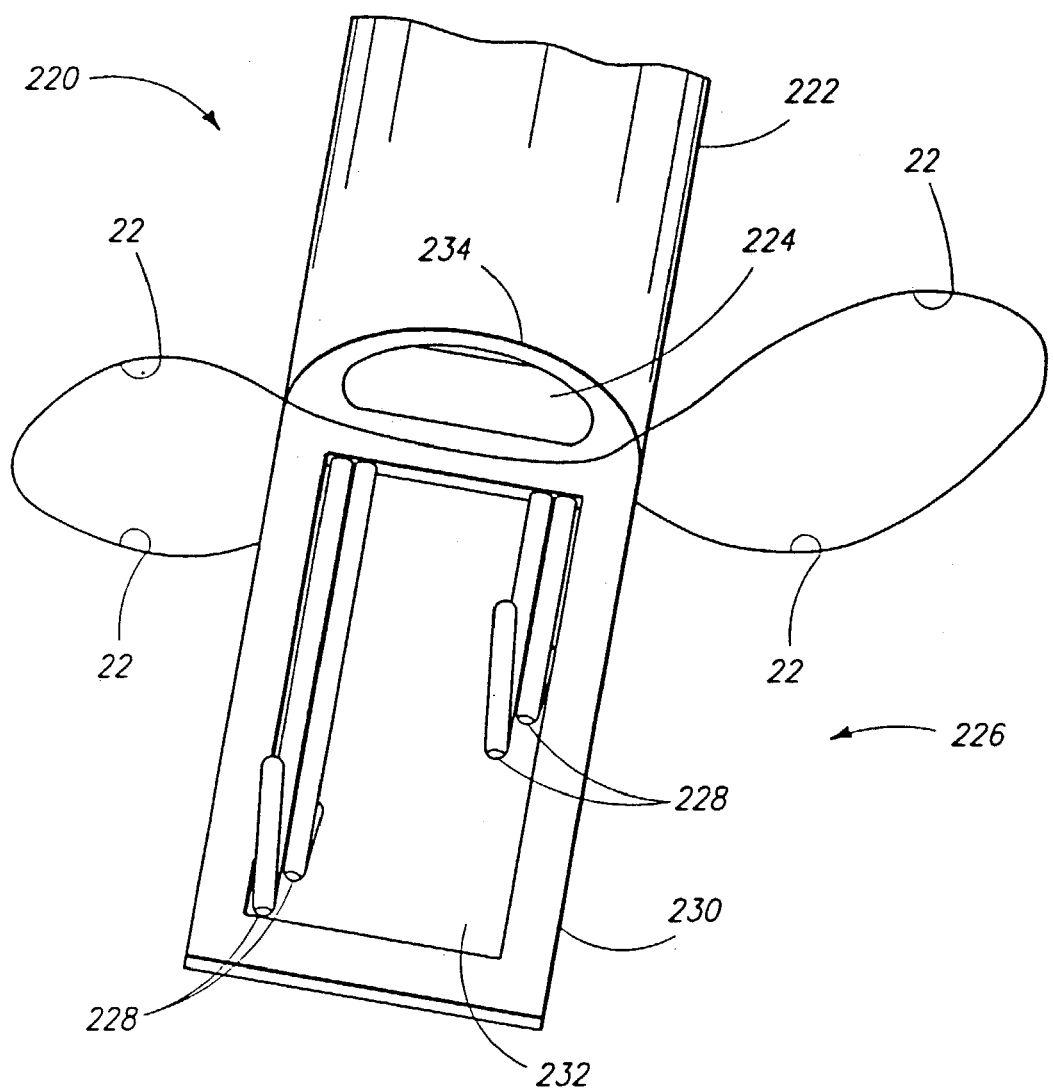
Figure 19C:
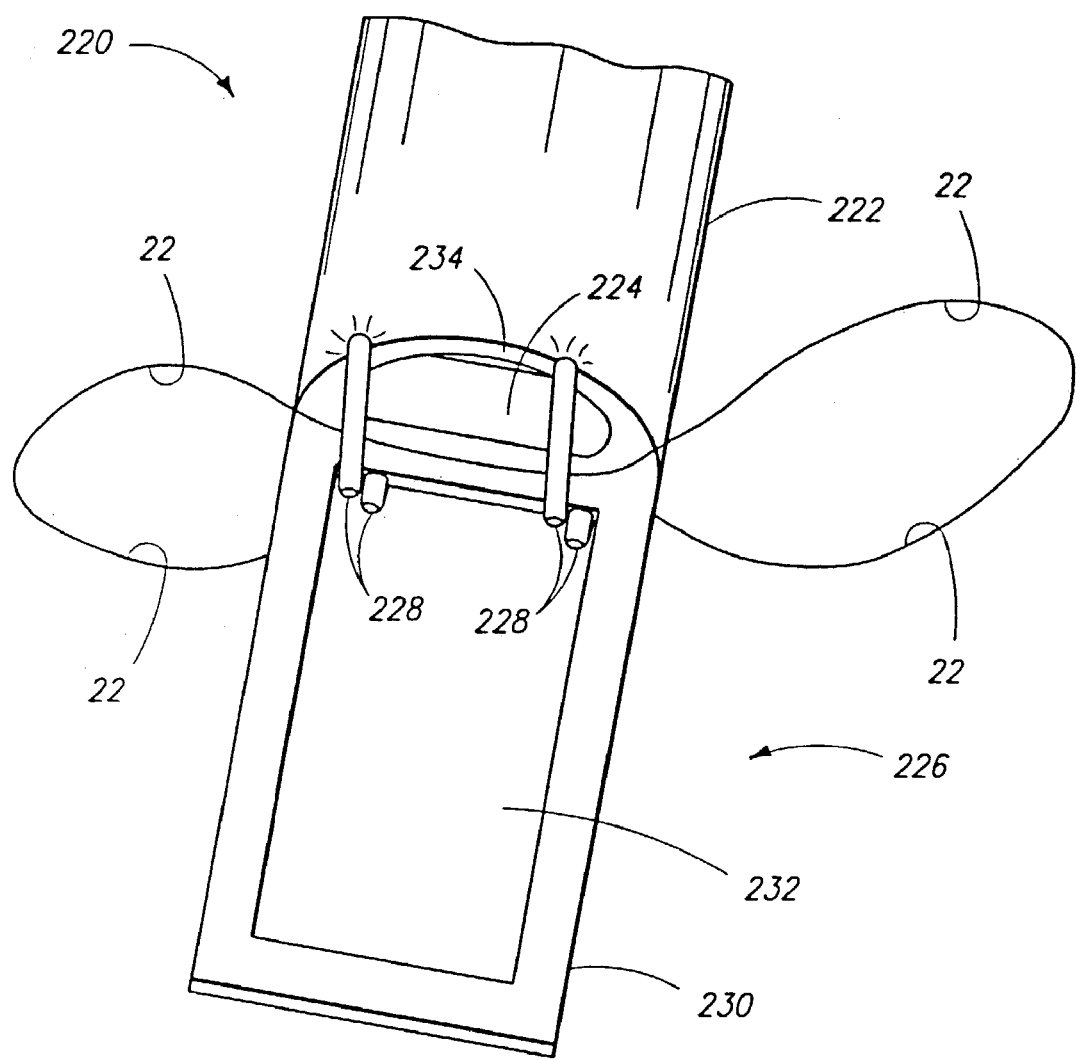
Figure 19D:
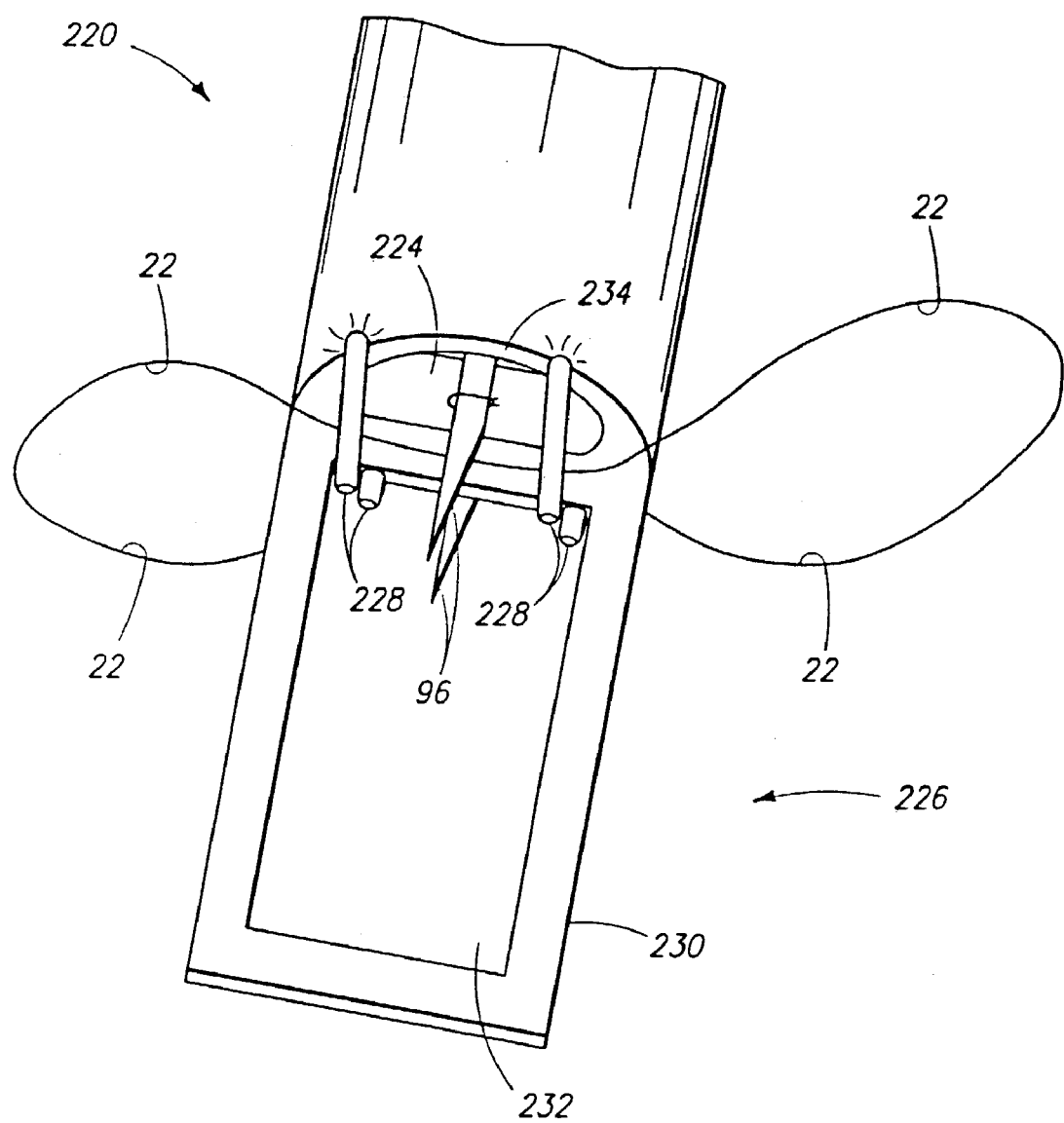

FIGS. 18a–18d illustrate a valve repair procedure using a tissue fastening device 200 and a spiral suture-based leaflet fastener 202. The leaflets 22 are stabilized, using one of the means disclosed herein (such as suction from two angled faces 204), and the fastener 202 is deployed. The fastener 202 comprises a helical needle 206, a trailing suture thread 208, and a pair of pledget anchoring devices 210. FIG. 18d is a detailed view of the pledget 210 used with the spiral suture-based leaflet fastener 202.

FIGS. 19a–19d illustrate a tissue stabilizing and fastening device 220 that uses the principles of vacuum stabilization/mechanical clamping and a suture-based toggle fastener. The device 220 includes a probe 222 having two vacuum ports for initial tissue stabilization. In addition to the vacuum ports 224, the device 220 includes a mechanical tissue stabilizer 226 with a four-part, rotatable and linearly extendable capture hooks 228. The distal tip includes a centered and distally-directed frame 230 defining a space 232 therein. The capture hooks 228 are folded flat within the space 232 and are rotatably and slidingly coupled to the probe 222 so that the capture hooks 228 may be rotated about 90 degrees and retracted to a capture position, wherein the leaflets 22 are "pinched" between distal ends of the capture hooks 228 and shoulders 234 of the probe 222. The two vacuum ports 224 also provide lumens for two of the needles 96 of FIG. 5b. The sharp ends of the needles 96 pierce the leaflets 22, and the pushers 98 are displaced (separately or in conjunction) to deploy the tissue fastener 90. After the needles 96 are retracted, the toggles 92 anchor the tissue fasteners 90 on the ventricular 31 side of the leaflets. The suture threads 94 are then tied off on the atrial 30 side to secure the leaflets 22 together, as seen in FIG. 6c.

FIGS. 19a–19d illustrate several steps in a valve repair procedure using the tissue stabilizing and fastening device 220. The stabilizing and/or fastening elements of the device 220 is formed relatively narrow in one dimension to enable it to be slipped between the two leaflets 22, wherein the capture hooks 228 are stored in a folded and extended position. The two leaflets 22 are initially stabilized by the vacuum ports 224. To further stabilize the leaflets 22, the capture hooks 228 are rotated 90 degrees and retracted, wherein the leaflets 22 are physically clamped against the shoulders 234 of the probe 222 and the distal ends of the capture hooks 228. It is noted that both vacuum stabilization and mechanical clamping do not have to be implemented to stabilize the leaflets 22. In certain applications, implementing only one of the mechanisms may be desireable. With the leaflets 22 properly stabilized, the needles 96 are driven forward to pierce the leaflets 22. The capture hooks 228 reduce the likelihood of losing grasp of the leaflets 22 during the piercing process. As shown in FIG. 5b, the pushers 98 are displaced (separately or in conjunction) to deploy the tissue fastener 90. After the needles 96 are retracted, the toggles 92 anchor the tissue fasteners 90 on the ventricular 31 side of the leaflets 22. The suture threads 94 are then tied off on the atrial 30 side to secure the leaflets 22 together, as shown in FIG. 6c.

Exemplary Mechanical Stabilizers and Fasteners

Figure 20:
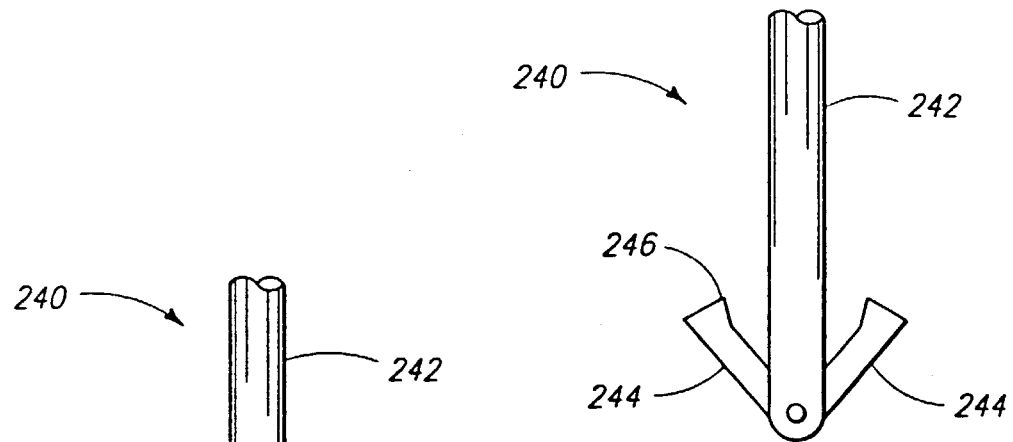
FIG. 20 is an elevational view of a mechanical tissue stabilizer with pivoting tissue clamps.
Figure 21A:
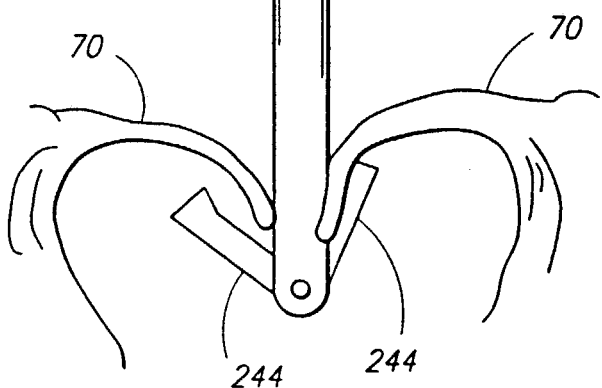
FIGS. 21a and 21b are elevational views of two steps in a valve repair procedure using the mechanical tissue stabilizer of FIG. 21.
Figure 21B:
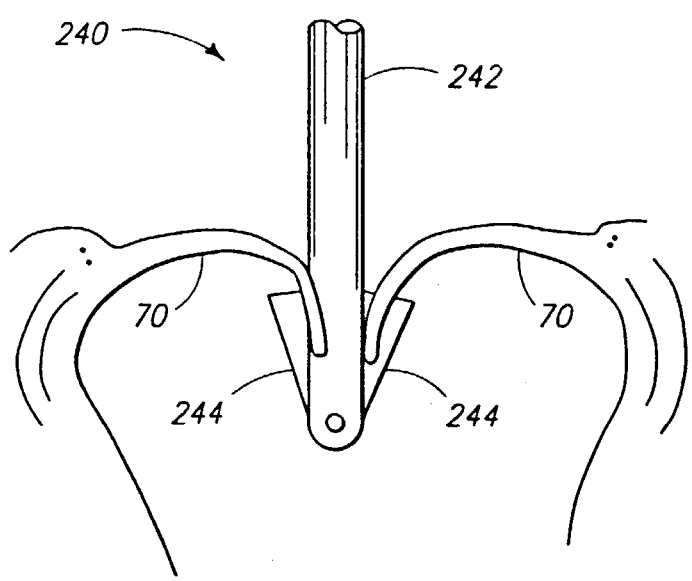

FIG. 20 shows a mechanical tissue stabilizer 240 that can be used to grasp tissue pieces 70 to be joined. The stabilizer 240 includes a probe 242 having a pair of pivoting arms 244 on a distal end. The arms 244 each have teeth 246 for added purchase on the tissue. FIGS. 21a and 21b illustrate a valve repair procedure initiated in accordance with the present invention using the tissue stabilizer 240.

Figure 22A:
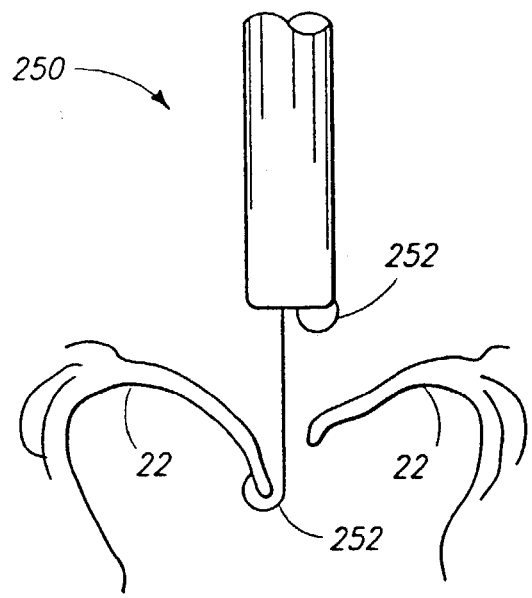
FIGS. 22a and 22b are elevational views of two steps in a valve repair procedure using a mechanical tissue stabilizer of the present invention having preformed hooks.
Figure 22B:
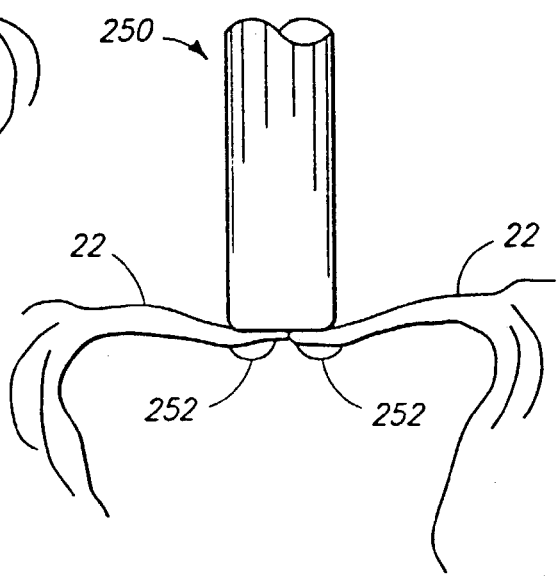

FIGS. 22a and 22b illustrate steps in a valve repair procedure using a mechanical tissue stabilizer 250 having preformed hooks 252. The hooks 252 are curled into approximately a three-quarter circle and deployed on the blind side of the leaflets 22 to grasp and stabilize them. The linear displacement of each hook 252 is separately controllable.

Figure 23A:
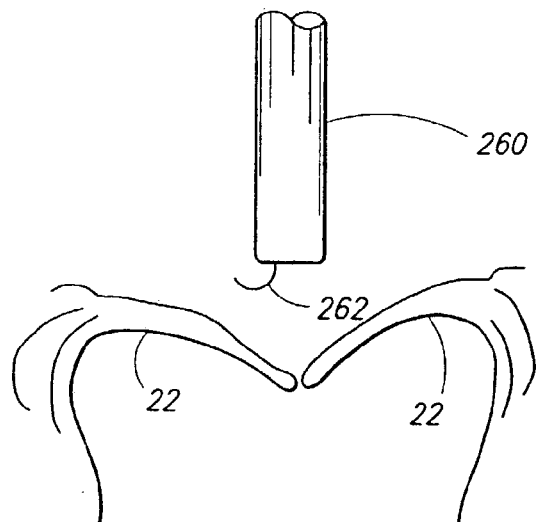
FIGS. 23a and 23b are elevational views of two steps in a valve repair procedure using a mechanical tissue stabilizer of the present invention having spring-biased hooks.
Figure 23B:
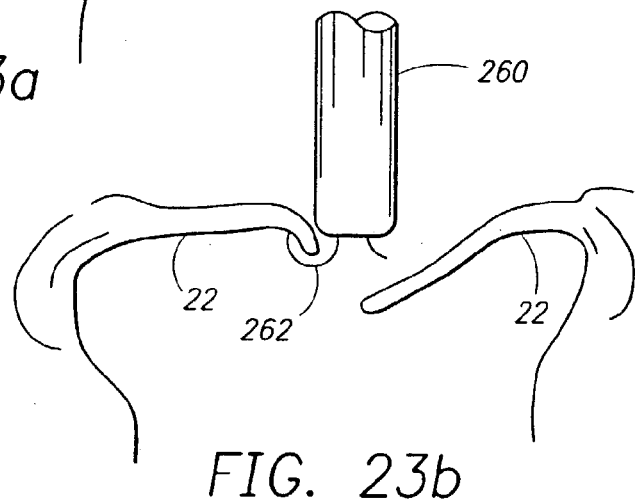
Figure 23C:
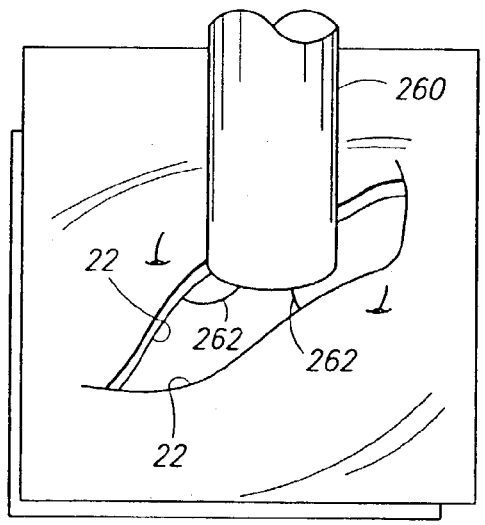
FIG. 23c is a detailed perspective view of two hooks of the tissue stabilizer of FIG. 23a extended to grasp the valve leaflets from the side opposite the tissue stabilizer.

FIGS. 23a–23c illustrate steps in a valve repair procedure using a mechanical tissue stabilizer 260 having spring-biased hooks 262. The hooks 262 curl into approximately a three-quarter circle when deployed, and are advanced on the blind side of the leaflets 22 to grasp and stabilize them. Again, the linear displacement of each hook 252 is separately controllable.

Figure 22C:
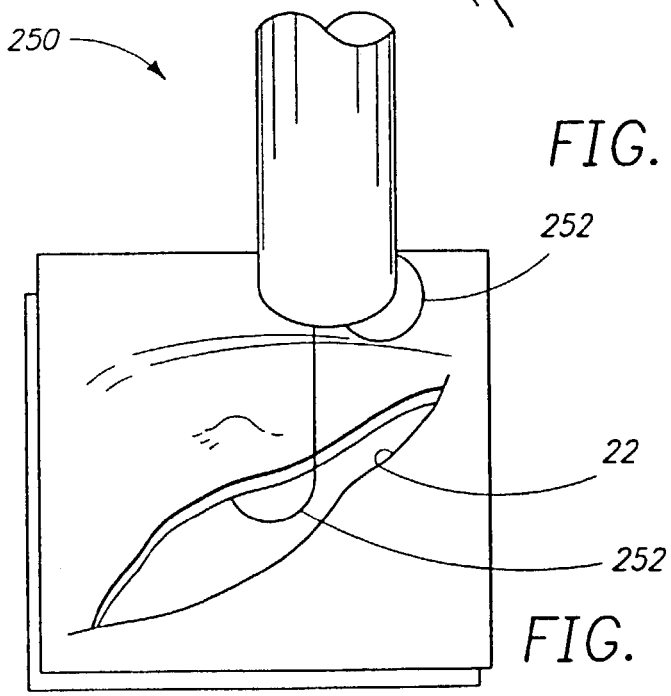
FIG. 22c is a detailed perspective view of a hook of the tissue stabilizer of FIG. 22a extended to grasp a valve leaflet from the side opposite the tissue stabilizer.
Figure 24A:
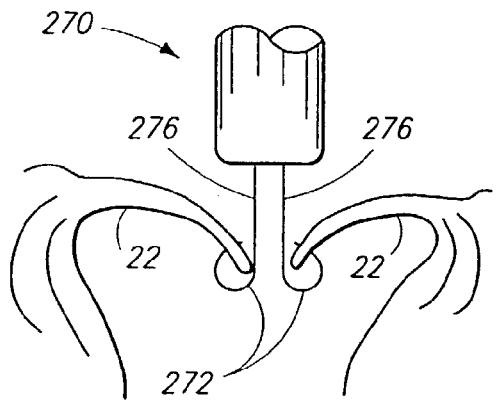
FIGS. 24a–24d are elevational views of several steps in a valve repair procedure using a mechanical tissue stabilizer of the present invention to deliver a non-suture-based fastener.
Figure 24D:
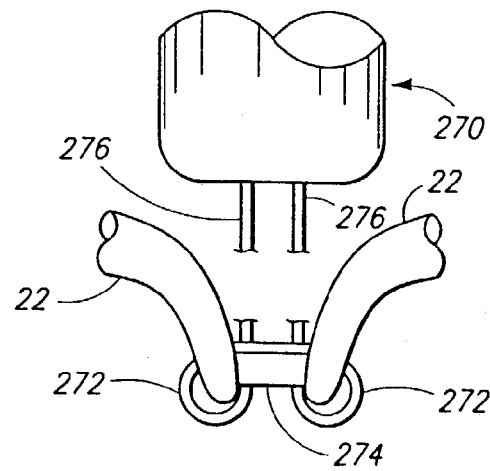
Figure 24B:
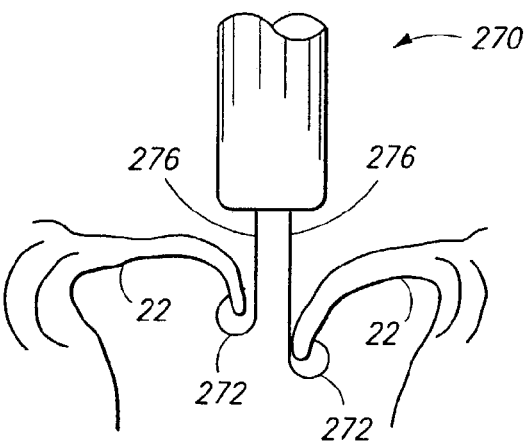
Figure 24C:
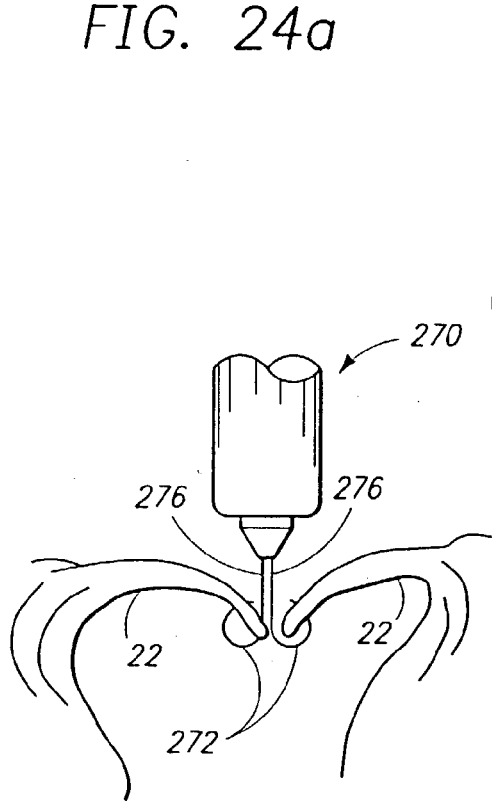

FIGS. 24a–24d illustrate a valve repair procedure using a mechanical tissue stabilizer 270 similar to both the stabilizers shown in FIGS. 22 and 23. After hooks 272 have stabilized the leaflets 22, a retainer 274 is slid down link rods 276 of each hook 272 (FIG. 24c). FIG. 24d shows the retainer 274 having reached the curvature of the hooks 272, at which point the link rods 276 are severed using conventional means. For example, the link rods 276 may be made of a polymer material, and a cutter deployed adjacent the device 270 to sever them. Again, the link rods 276 are separately displaceable as seen in FIG. 24b.

Exemplary Staple and Clip-Type Fasteners

FIG. 25a shows an exemplary tissue staple 280 for joining two tissue pieces in an open configuration. The staple 280 includes a bridge portion 282 and four gripping arms 244, two on each side. The gripping arms 284 are initially curled in a semi-circle upward from the plane of the bridge portion 282 and terminate in sharp points approximately in the plane of the bridge portion 282. FIG. 25b shows the staple 280 when closed, with the gripping arms 284 curled underneath the plane of the bridge portion 282 toward each other.

FIGS. 26a–26c illustrate several steps in a valve repair procedure using an exemplary tissue fastening device 290 for delivering the tissue staple 280. The device 290 includes a probe 292 with an internal lumen 294 within which a pusher 296 is slidable. A stop member 298 is also provided underneath the bridge portion 282 of the staple 280 to prevent displacement of the bridge portion 282 toward the leaflets 22. After stabilizing the leaflets 22, the pusher 296 displaces downward which causes the staple 280 to undergo a plastic deformation from the configuration of FIG. 25a to that of FIG. 25b. The sharp points of the gripping arms 284 pass through the leaflets 22 and anchor the staple 280 therein. Finally, the stop member 298 is disengaged from under the bridge portion 282, and the device 290 is retracted.

Figures 27A, 27B, 27C:
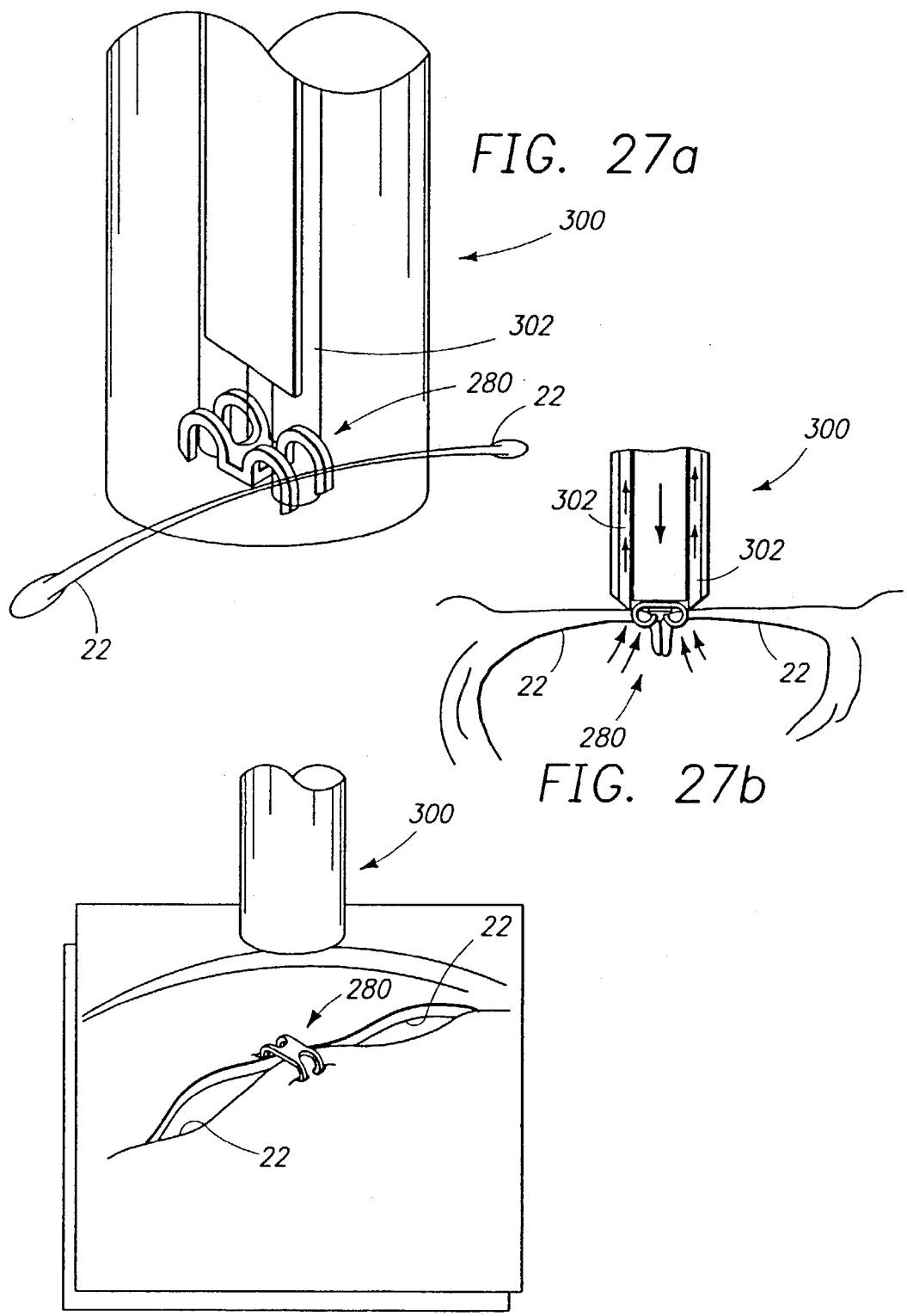
Figure 34A:
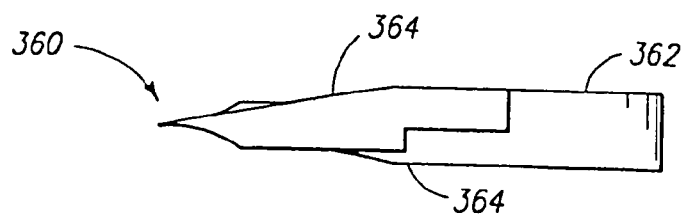
FIGS. 34a–34f are elevational and perspective views of a tissue fastener of the present invention having spring-loaded jaws.
Figure 34B:
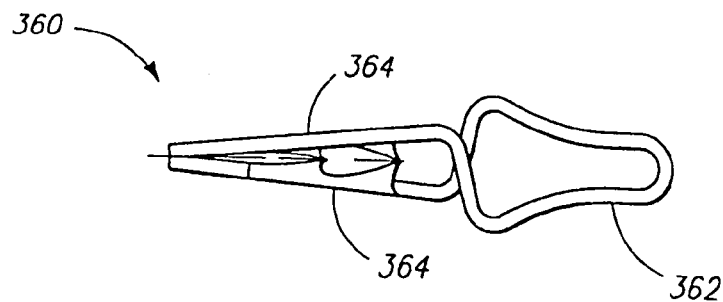
Figure 34C:
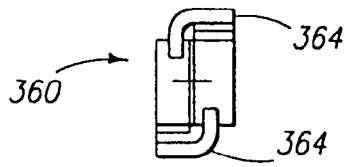
Figure 34D:
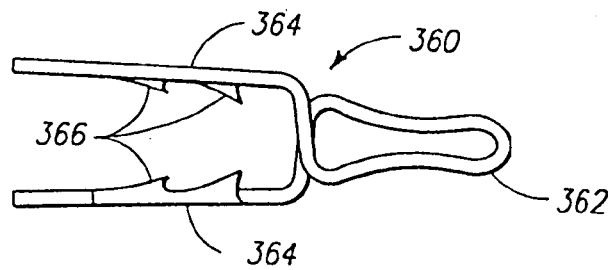
Figure 34E:
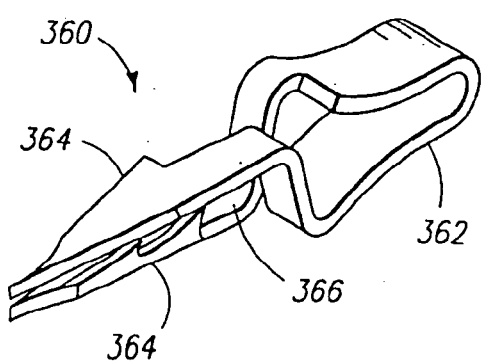
Figure 34F:
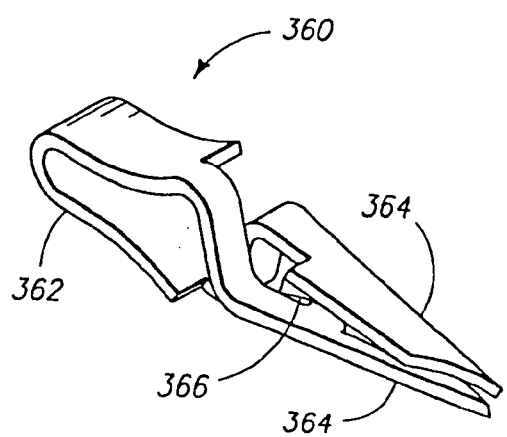

FIG. 27a illustrate the use of a tissue stabilizing and fastening device 300 for deploying the staple 280 of FIG. 25. The device 300 is quite similar to the device 290 of FIG. 26, with an exemplary stabilizing means shown in the form of vacuum chamber(s) 302 on each side of the staple deployment mechanism.

FIGS. 28a and 28b illustrate a further tissue fastening device 310 of the present invention for delivering an alternative "toggle-like" tissue clip 312. In FIG. 28a the clip 312 is shown open, while in FIG. 28b the clip 312 is shown closed. The clip 312 is plastically deformed from open to close using a clamping mechanism 314 that flattens a ring-shaped head portion 316 of the clip 312. Two pincher arms 318 thus pivot toward each other and grasp and hold tissue therebetween.

FIGS. 29a–29c depict steps in a valve repair procedure using the tissue fastening device 310 of FIG. 28. One method for inserting the device 310, as well as many other devices of the present invention, between the two leaflets 22 is detailed in FIG. 29a. Specifically, the stabilizing and/or fastening elements of the devices of the present invention can be formed relatively narrow in one dimension to enable them to be slipped between two tissue pieces so that the pieces can then be fastened together from the blind side. Thus, for example, the tissue fastening device 310 is seen in FIG. 29a rotated to orient the narrow dimension in line with the gap between the leaflets 22.

FIGS. 30a–30b and 31a–31d illustrate an alternative tissue fastening device 320 for delivering another "toggle-like" tissue fastening clip 322. In contrast to the clip 312 of FIG. 28, the clip 322 pierces the tissue pieces 70 from the front side, and is then deformed to clamp the tissue pieces 70 together.

FIGS. 32a–32d illustrate various embodiments of barbed clips 330, 332, 334, 336 used to fasten tissue pieces together using the principles of the present invention. The barbed clips include a bridge portion 338, 340, 342, 344 and terminate in sharp points.

FIGS. 33a–33c illustrate several steps in a valve repair procedure using an exemplary barbed clip deployment device 350 for delivering the barbed clip 330. The device 350 includes a probe 352 with an internal lumen 354 within which an internal driver 356 is slidable. A stop member 358 is provided at the distal end of the probe 352 to spread the two barbs away from each other as it is pushed forward. The tips of the barbed clip 330 are displaced towards the leaflets 22 by downwardly sliding the driver 356. After the clip 330 pierces the leaflets 22 from the front side, the clip 330 is disengaged from the device 350 as shown in FIG. 33c. When the clip 330 is disengaged from the device 350, it returns to its retracted position and compresses the leaflets 22 together. Again, any of the stabilizers of the present invention can be used in conjunction with the deployment device 350.

Figure 35A:
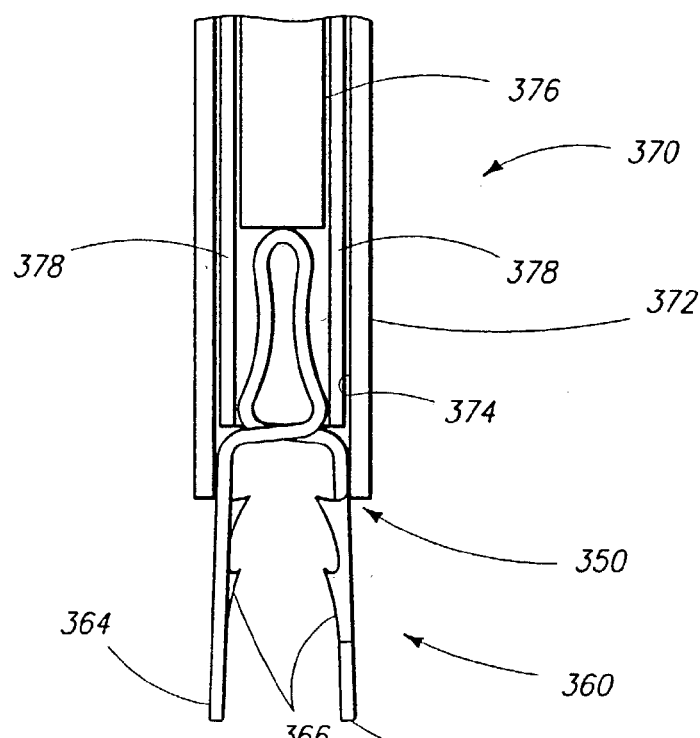
Figure 35B:
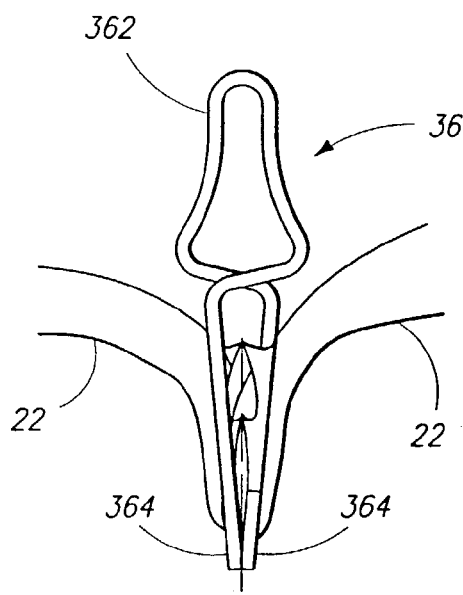
FIGS. 35b and 35c are sectional views of the tissue fastener of FIG. 34a in both closed and open positions around the tissue being connected.
Figure 35C:
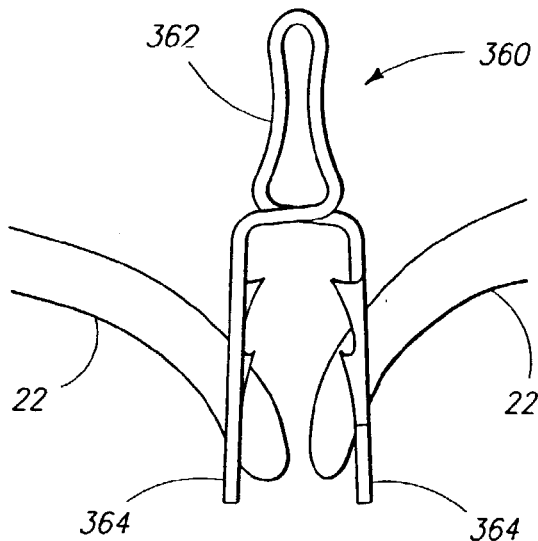

FIGS. 34a–34f illustrate a spring-loaded clip 360 used to fasten tissue pieces 70 together. The clip 360 comprises a spring portion 362 and two arms 364, and the arms 364 include a plurality of barbs 366. The distal ends of the arms 364 are tapered to enable the clip 350 to pierce the leaflets 22, and the arms 364 are configured to overlap each other after closure (see FIG. 34c). FIGS. 35a–35c illustrate a valve repair procedure using a clip deployment device 370 for delivering the spring-loaded clip 360. The device 370 includes a probe 372 with an internal lumen 374, and a pusher 376 is slidably coupled to the internal lumen 374. A sleeve 378 is disposed between the pusher 376 and the internal wall of the lumen 374. The spring portion 362 of the clip 360 is housed within the sleeve 378 in its open position, wherein the spring portion 362 is compressed by the sleeve 378. As seen in the sequence of FIGS. 35a–35c, downward movement of the pusher 376 causes the clip 360 to move downward and pierce the leaflets 22 from the front side. The clip 360 is pushed downward at a velocity adequate to insure penetration without dislodging the leaflets 22 from the vacuum source. As the clip 360 is disengaged from the device 370, the clip 360 automatically springs to its closed position and compresses the leaflets together.

Figure 36A:
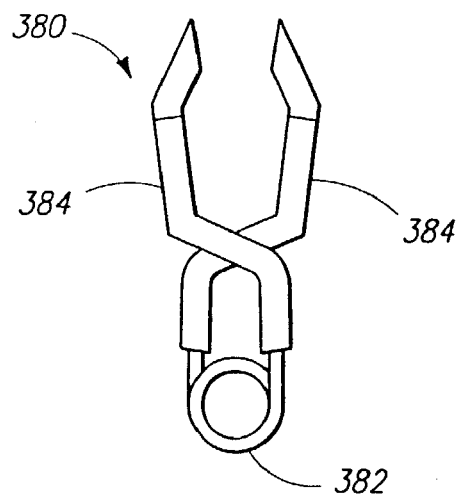
FIGS. 36a–36c are elevational views of a further tissue fastener of the present invention having spring-loaded jaws.
Figure 36B:
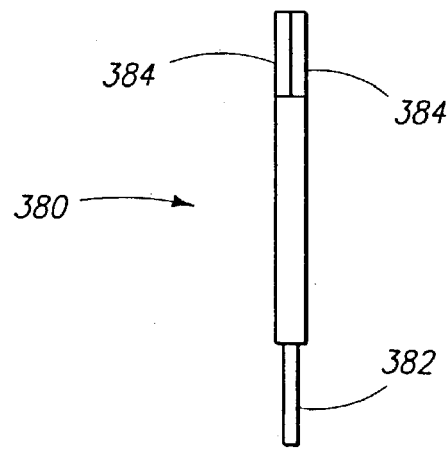
Figure 36C:
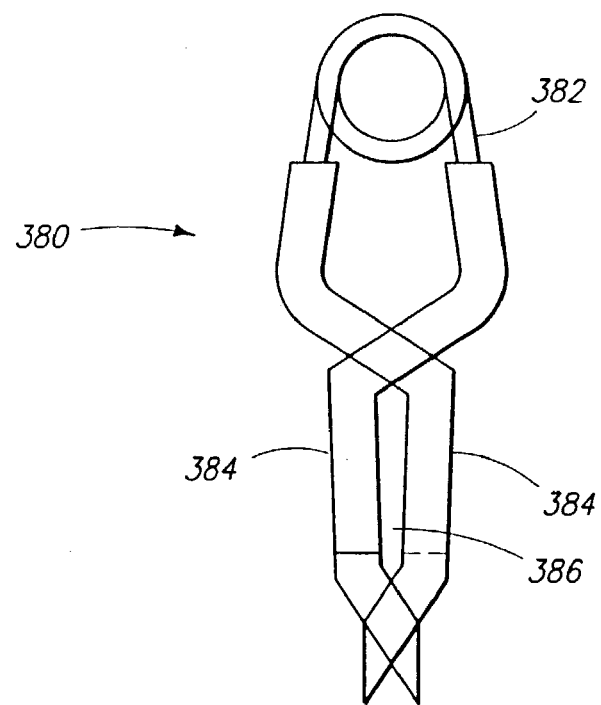

FIGS. 36a–36c illustrate another embodiment of a spring-loaded clip 380 used to fasten tissue pieces together. The clip 380 comprises a spring portion 382 and two arms 384 having distal ends which are tapered and extend inwardly to pierce and lockingly secure the leaflets 22. A gap 386 exits between midportions of the arms 384 when the clip 380 is in its closed position.

Figures 37A, 37B:
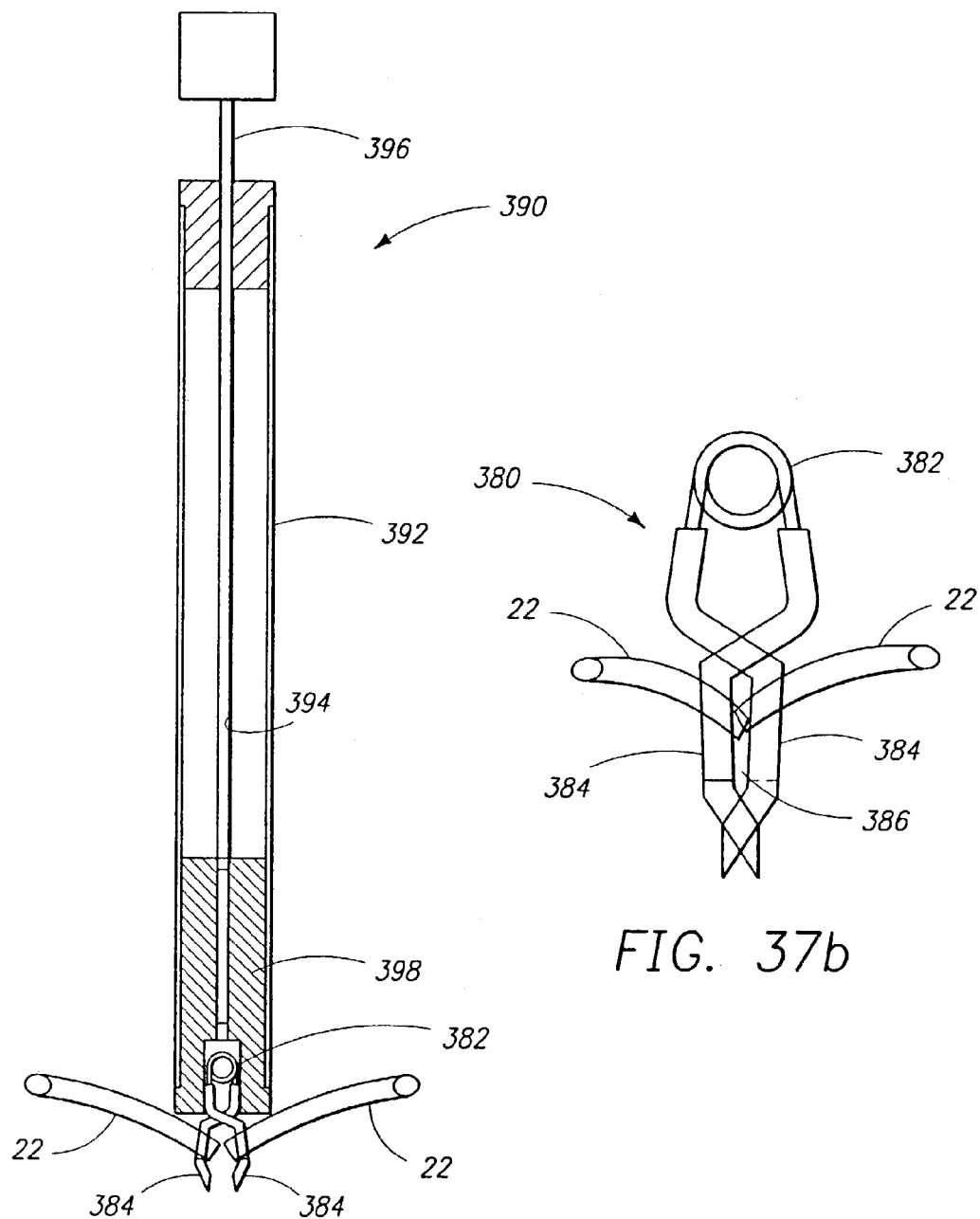

FIGS. 37a and 37b illustrate a clip deployment device 390 having a probe 392 with an internal lumen 394 and a pusher 396 slidably coupled to the internal lumen 394. The spring portion 382 is retained in a compressed state within a housing member 398 such that the clip 380 is held in an open position. Downward movement of the pusher 396 causes the clip 380 to move downward and pierce the leaflets 22 from the front side. As the spring portion 384 exits the housing member 398, the clip 380 automatically springs into its closed position and lockingly secures and compresses the leaflets 22.

Exemplary Integrated Stabilizing and Fastening Device

Figure 44:
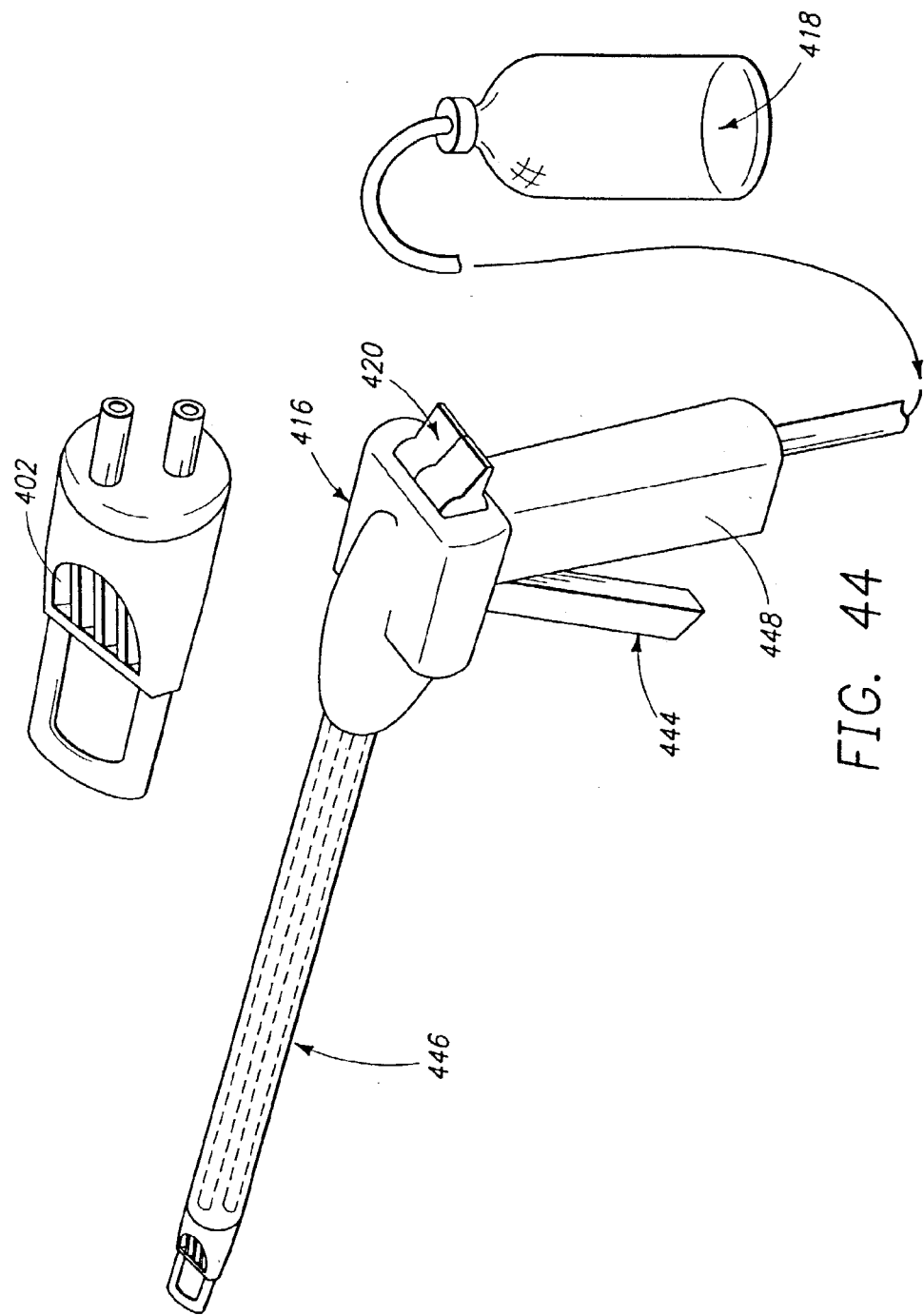
FIG. 44 is a perspective view of an exemplary embodiment of a handpiece that is utilized with the device of FIG. 38.

FIGS. 38–46 illustrate another exemplary embodiment of an integrated tissue stabilizing and fastening device 400 which captures tissue pieces, such as valve leaflets, with vacuum and fastens the tissue pieces with sutures. The device 400 is similar to the devices illustrated in FIGS. 11–15 in that it comprises a slender distal portion which accesses the heart valve trans-atrially. The device 400 is placed through a specialized cannula and it has a proximal handpiece portion which provides user controls. In an exemplary embodiment the distal portion is approximately 10 mm in diameter and it terminates in vacuum ports and a needle array as depicted in FIGS. 38 through 41. The handpiece portion contains individual vacuum port controls and needle deployment controls as generally depicted in FIG. 44. The device 400 is connected to a vacuum source via a flexible hose. The illustrated device 400 is utilized to grasp the tissue pieces and place the sutures correctly. Remote tying and cutting of the sutures can be accomplished with a separate device. The following description of the use of the device 400 will be made with respect to the stabilizing and fastening of the leaflets of a mitral valve. However, those of skill in the art will appreciate that the device can also be used to stabilize and fasten other physiological tissues. A more detailed description of the device 400 follows.

FIGS. 38–41 illustrate device 400 in various modes of operation. Device 400 comprises vacuum ports 402 and 404 at the distal tip of device 400 which are connected to the vacuum source 418 (shown in FIG. 44). Needle carrier 406 is centrally disposed at the distal end of device 400 and is configured to be extended from and retracted back into device 400. Needles 408 are mounted on mounting blocks 410 within carrier 406 and mounting blocks 410 are pivotably attached to carrier 406 via pivot pin 412. Needle catchers 414 are retained in ports 402 and 404 to grip and retain needles 408 when needle carrier is retraced back into device 400 upon completion of the procedure.

FIG. 44 illustrates an exemplary handpiece 416 which connects vacuum source 418 to device 400 and delivers vacuum to vacuum ports 402, 404 at the distal tip of the device. Pinch valves 420 mounted on the handpiece 416 of the device normally constrict the vacuum lines. By individually manipulating each valve, the operator can differentially control access to the vacuum source. By partially deflecting one valve, the operator permits momentary access by one of the vacuum ports to the vacuum source. By fully deflecting one of the valves, the operator permits continuous access to the vacuum source. The provision of separate, individually controlled valves permits the delivery of differential vacuum to one or the other of ports 402 and 404. This may be very helpful in certain cases of valve prolapse where it is necessary to capture one leaflet and move it laterally with respect to the second leaflet to facilitate final capture.

The vacuum system has, of necessity, two different operating modes. Initially, it is necessary to capture the leaflets. This requires relatively high flow rates to attract a leaflet to a vacuum port. In an exemplary embodiment the flow rate is approximately 10 cc per second. Since this flow rate is capable of exsanguinating and destabilizing the beating heart, the invention provides for quick and efficient leaflet capture. Efficient capture requires that the vacuum port be close to the leaflet when the vacuum is turned on. Proper placement of device 400 with respect to the leaflets is facilitated by placement of echogenic members at or near vacuum ports 402 and 404 to enhance visualization by echo.

Echogenicity is enhanced by the proper choice of materials. The device, being entirely of plastic except for small metal parts in the immediate vicinity of the ports, takes advantage of the relatively high visibility of metal while avoiding the shadowing properties of large masses of metal. The metal parts in question are needle catchers 414, needles 408 and pivot pin 412. Since these parts are located near the vacuum ports 402 and 404 in the long axis of the device, they serve to locate ports 402 and 404 axially relative to the valve leaflets prior to vacuum application. Since they are discontinuous and symmetrical about ports 402 and 404 in the short axes, they facilitate the correct radial orientation of the ports relative to the valve leaflets. Echogenicity is further enhanced by a polymer coating which can be wholly or selectively applied to the ports 402 and 404. This coating creates a microscopic boundary layer which effectively separates the ports from the blood under echo visualization.

In an exemplary embodiment, the vacuum surfaces of the ports 402 and 404 are angled between zero and ninety degrees relative to a plane normal to the long axis of the device. This is intended to conform somewhat to the shape of the valve leaflets. In another exemplary embodiment the ports are angled between 15 to 40 degrees relative to a plane normal to the long axis of the device. In yet another embodiment the ports are angled at about 25 degrees relative to that plane.

Once the leaflets have been captured, the second operating mode of the vacuum system is to hold the leaflets in position for suture application without additional exsanguination. This implies high holding force and no flow. These properties are primarily a function of pressure differential, port area and port shape. In one embodiment, adequate holding force is obtained at a maximum differential pressure with port areas in the approximate range of 0.03–0.04 square inch per port. In the embodiment illustrated in FIG. 43, a geometrically optimized cylindrical device is shown having two separate "D" shaped ports 404 and 404. The illustrated device 400 has about 10 mm in diameter. Since a vacuum port with the highest ratio of area to perimeter (i.e., a circle) will have the highest average peel away strength, some modification of the "D" shaped port is useful for functional optimization. This is accomplished in the device by filling in the corners of the "D" where the arc meets the straight portion at acute angles. This can be seen clearly on port 402 in FIG. 38. The corners which have been eliminated represent the part of the "D" shape least resistant to peel away of the leaflet which is being held by vacuum.

Vacuum ports 402 and 404 further have barriers 422 which serve two distinct purposes. Barriers 422 support the valve leaflet to prevent it from being sucked deep into the ports 402 and 404, thereby minimizing tissue trauma. This has the further useful effect of controlling the position of the leaflet relative to the suture needles so that the latter penetrate the leaflet in a predictable way, placing sutures the correct distance from the edge of the leaflet for reliable repair. In the illustrated embodiment of FIG. 43, the barriers are recessed below the perimeter of the "D" slot. In an exemplary embodiment the barriers are recessed about 0.02 inches. This slightly distorts the valve tissue and creates resistance to displacement of tissue as it is moved laterally by the device to approximate the leaflets. If the barriers were not recessed, the only resistance to lateral drag would be the coefficient of friction between the port surface and the leaflet which is likely to be low in the bloody environment.

A pre-evacuated sterile bottle 418 serves as a passive vacuum source for capturing and holding the leaflets. In an exemplary embodiment, the system is designed to minimize total exsanguination to about 200 cc per procedure. A standard 2 liter bottle can provide that amount of flow with negligible increase in absolute pressure. This offers a significant advantage over utility vacuum sources in hospital operating rooms and dedicated active pumps. Utility sources are not well controlled and active pumps present cost, convenience and sterility issues.

Once captured, leaflets will be fastened by remotely applied sutures. The mechanism by which this is accomplished is shown in FIGS. 39 through 42 as will be discussed below. FIGS. 45a and 45b illustrates two exemplary suture configurations which the system can provide, depending on the way in which the sutures and needles are loaded into the device.

In one embodiment, two lengths of suture (not shown) are used with a straight needle 408 attached to each suture end. Sutures are inserted into a coaxial hole in the end of the needle opposite the point and the body of the needle is crimped to retain the suture using conventional suture technology. A groove near the tip of the needle provides a means for grasping and pulling the needle through after it has pierced the valve leaflet. Sutures can be monofilament or braided or other types suitable for cardiovascular use. In an exemplary embodiment, a size 4-0 monofilament suture capable of gamma sterilization (e.g. Novafil) is used since the internal configuration of the device favors radiation sterilization and it is desirable to be able to sterilize the entire system at one time. The needles will receive a lubricious coating (e.g. silicone) to reduce penetration force and fraction.

In one embodiment, the needles and sutures are an integral part of a single use completely disposable device. In a second embodiment, the needles, sutures and associated hardware may be packaged as a cartridge which plugs into a reusable device. This device can be limited to multiple use in a single procedure, or reusable for multiple procedures.

Figure 38:
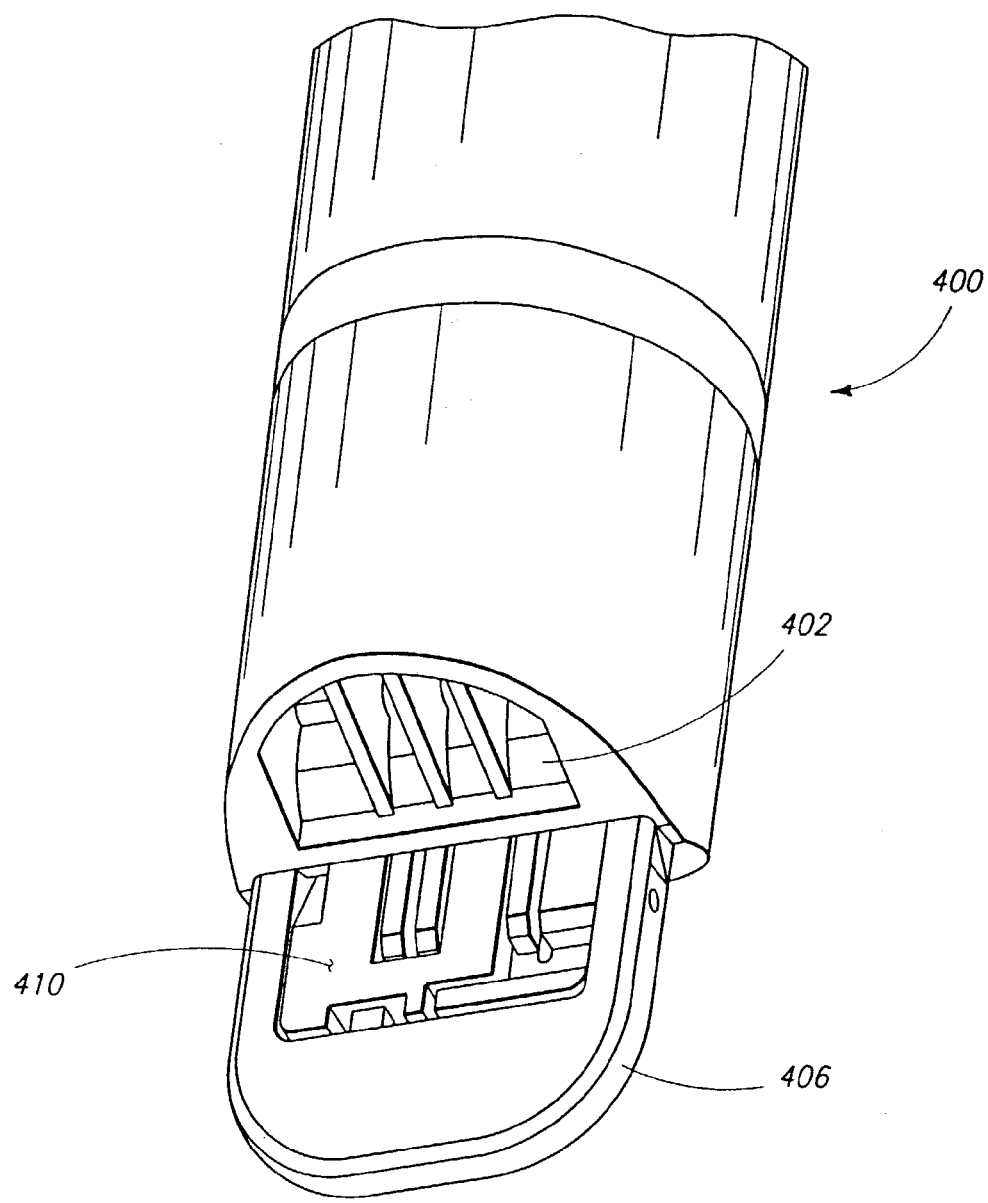
FIG. 38 is a perspective view of an exemplary integrated tissue stabilizer and fastening device of the present invention.
Figure 39:
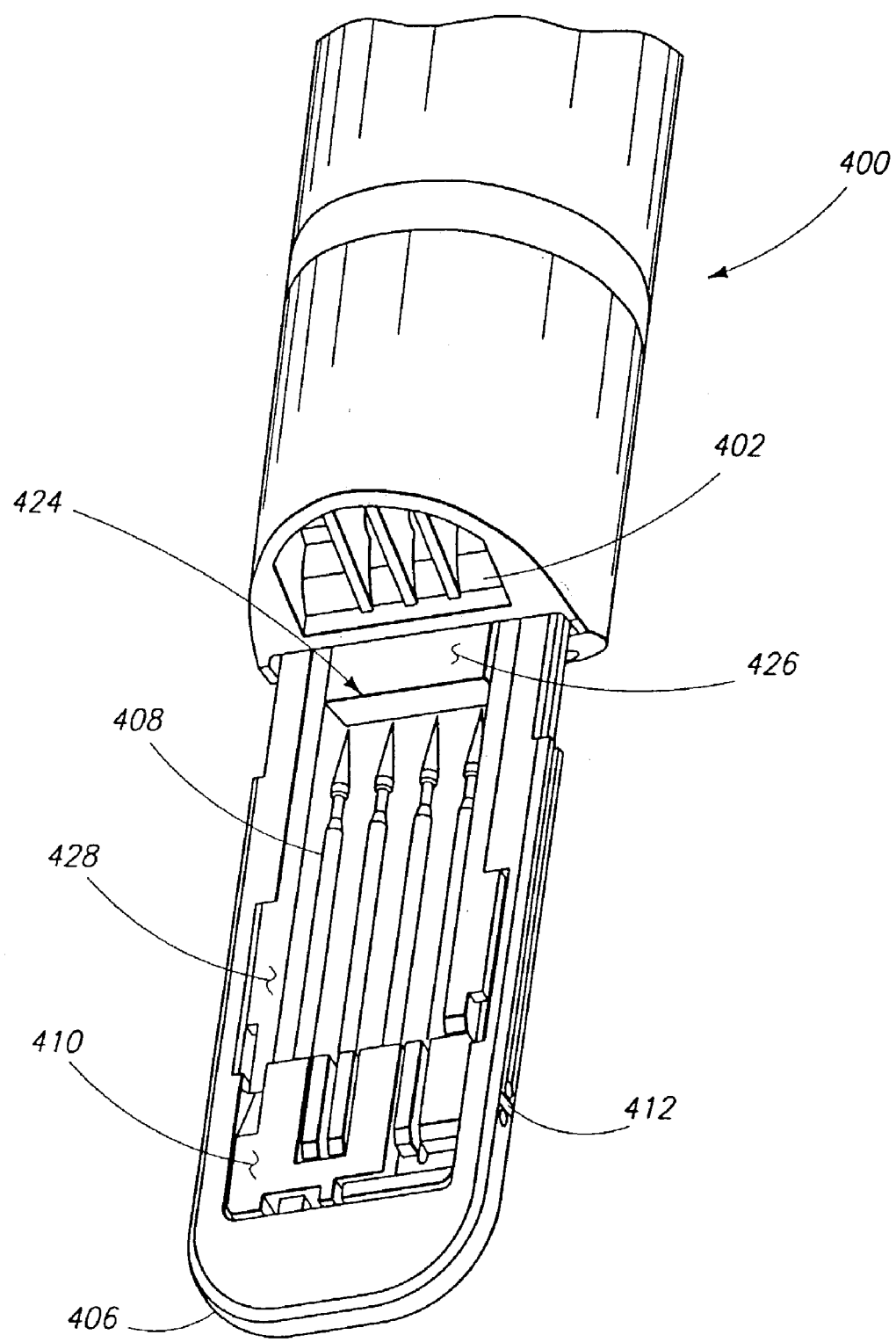
FIG. 39 is a perspective view of the device of FIG. 38 wherein the needle carrier is extended.

Needle carrier 406 further comprises needle driver assembly 424. Driver assembly 424 includes blocks 410, axle 412, needle driver 426, and cams 428. Needles 408 are slidably mounted in blocks 410 which pivot about axle 412. Blocks 410 may be slotted in the area of the hole which receives the needle so that the needles can be held in place by controlled friction. Sutures (not shown) protruding from the ends of the needles can be routed along the sides of the needle carrier 406 in grooves provided for that purpose. The needles are initially recessed into the body of the device 400 by virtue of the recessed position of carrier 406, as shown in FIG. 38. The position of the needles in this state is shown in FIG. 39. The needle mounting blocks 410 are pivoted so that needles 408 lie in a single row within the confines of the needle carrier 406. One end of driver element 426 which drives the needle carrier 406 in and out of the distal device tip is positioned just above the needle points so that the needles 408 are retained in their holders 410 against any drag which might tend to dislodge them. The other end of the driver element 426 is connected to a control at the proximal end of the device by which the operator manipulates the needles 408.

Figure 40:
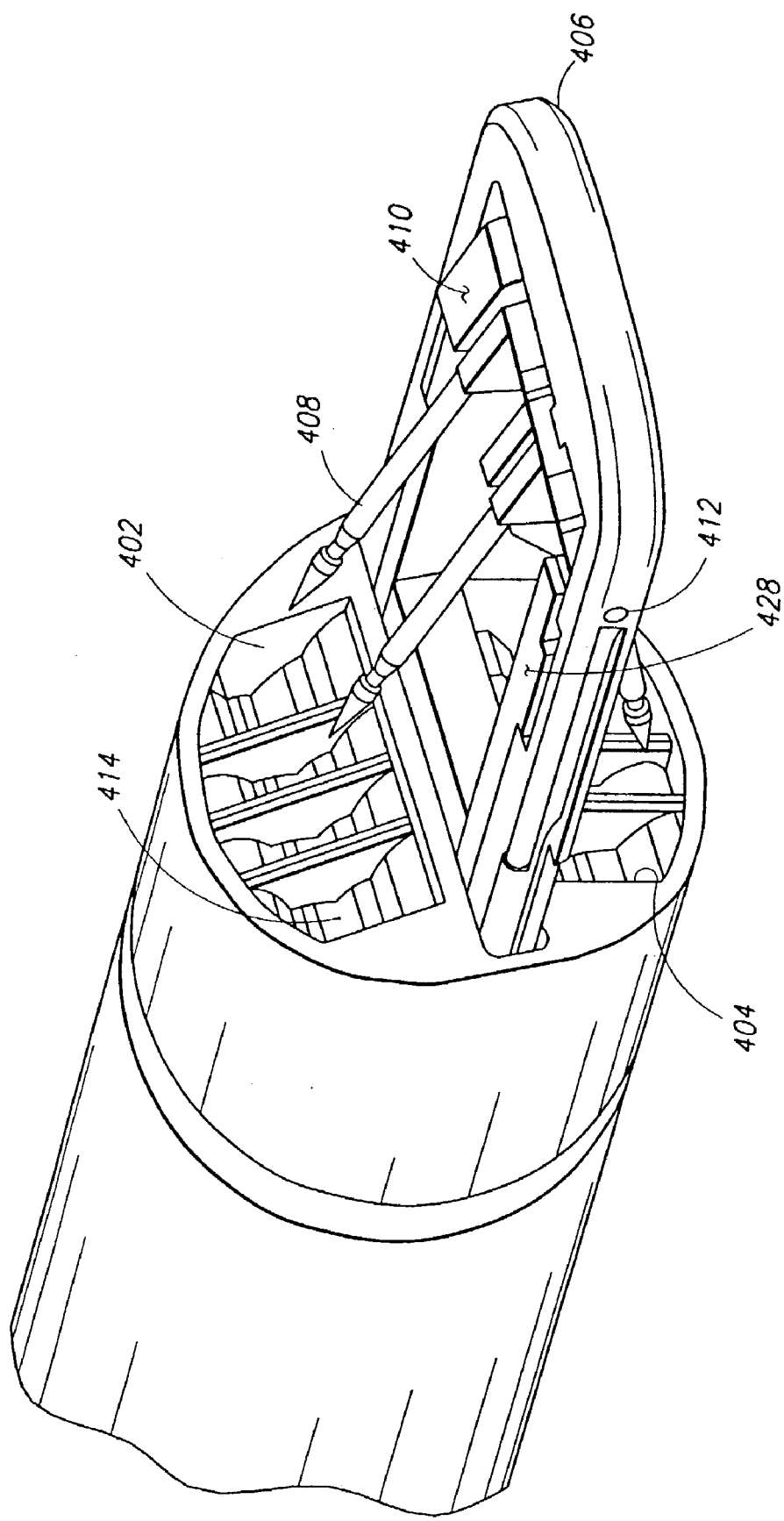
FIG. 40 is a perspective view of the device of FIG. 38 showing the initial release of the needles.
Figure 41:
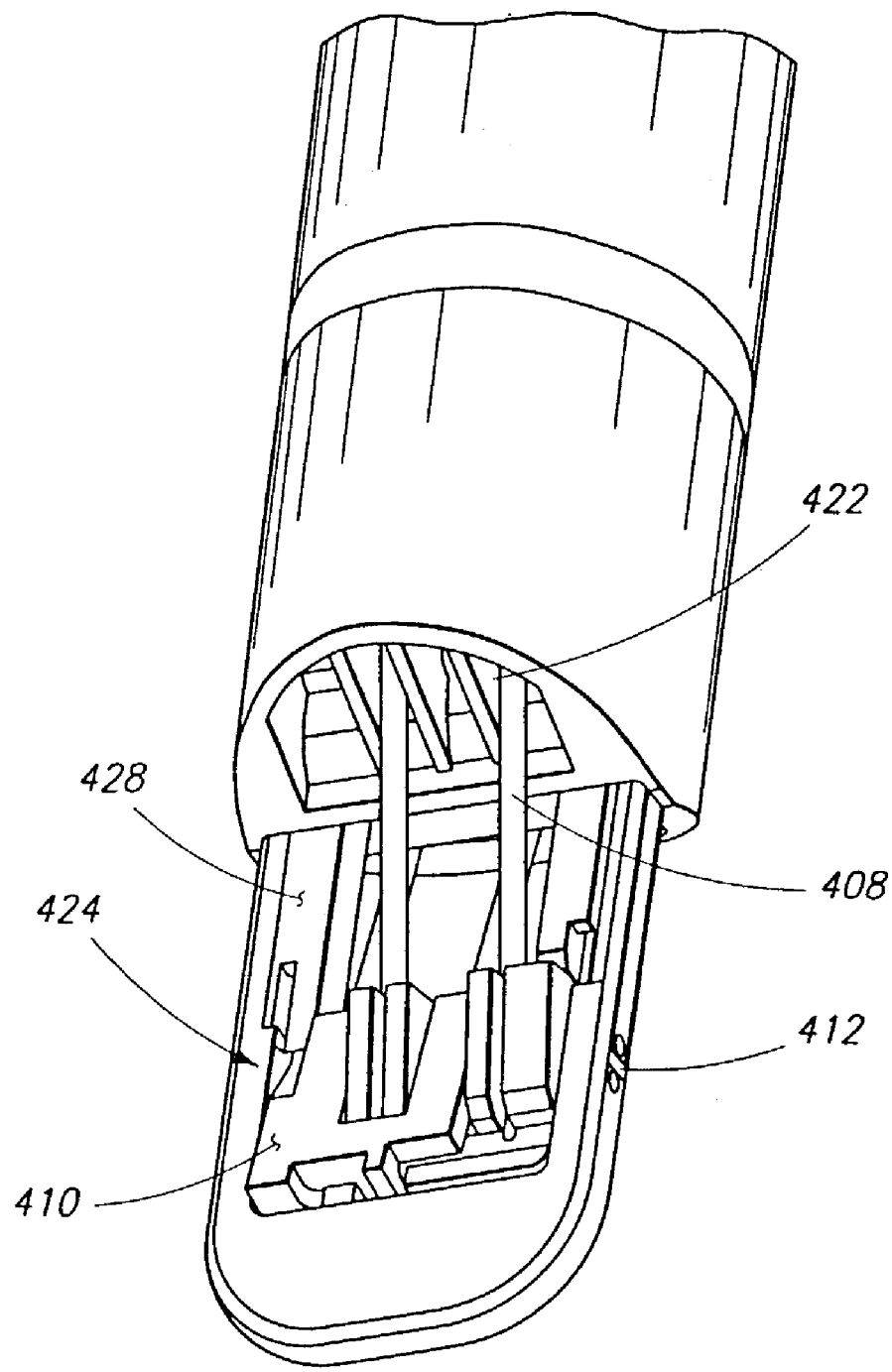
FIG. 41 is a perspective view of the device of FIG. 38 showing the needles captured within the vacuum ports.
Figure 42:
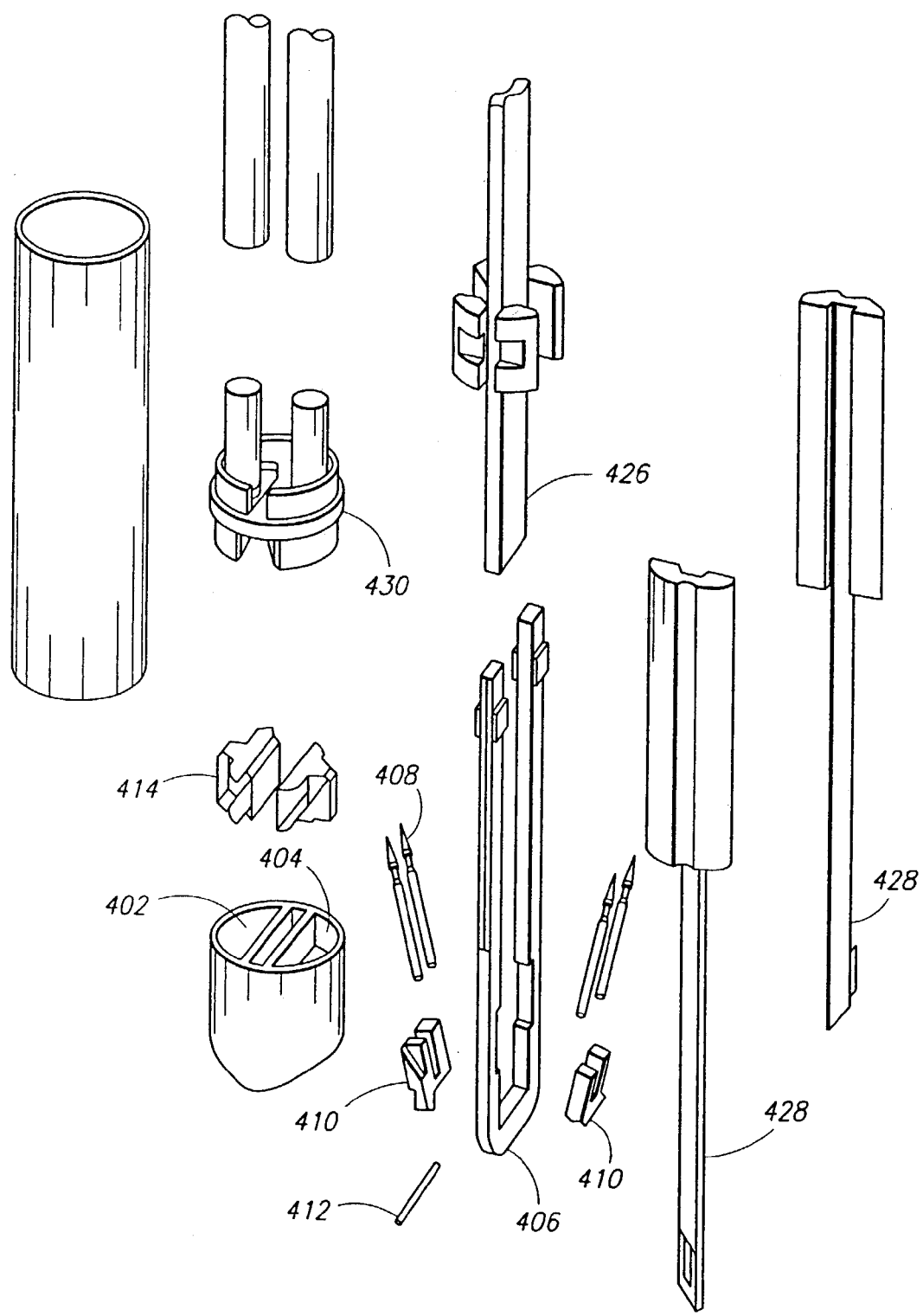
FIG. 42 is an exploded view of various components of the device of FIG. 38.
Figure 43:
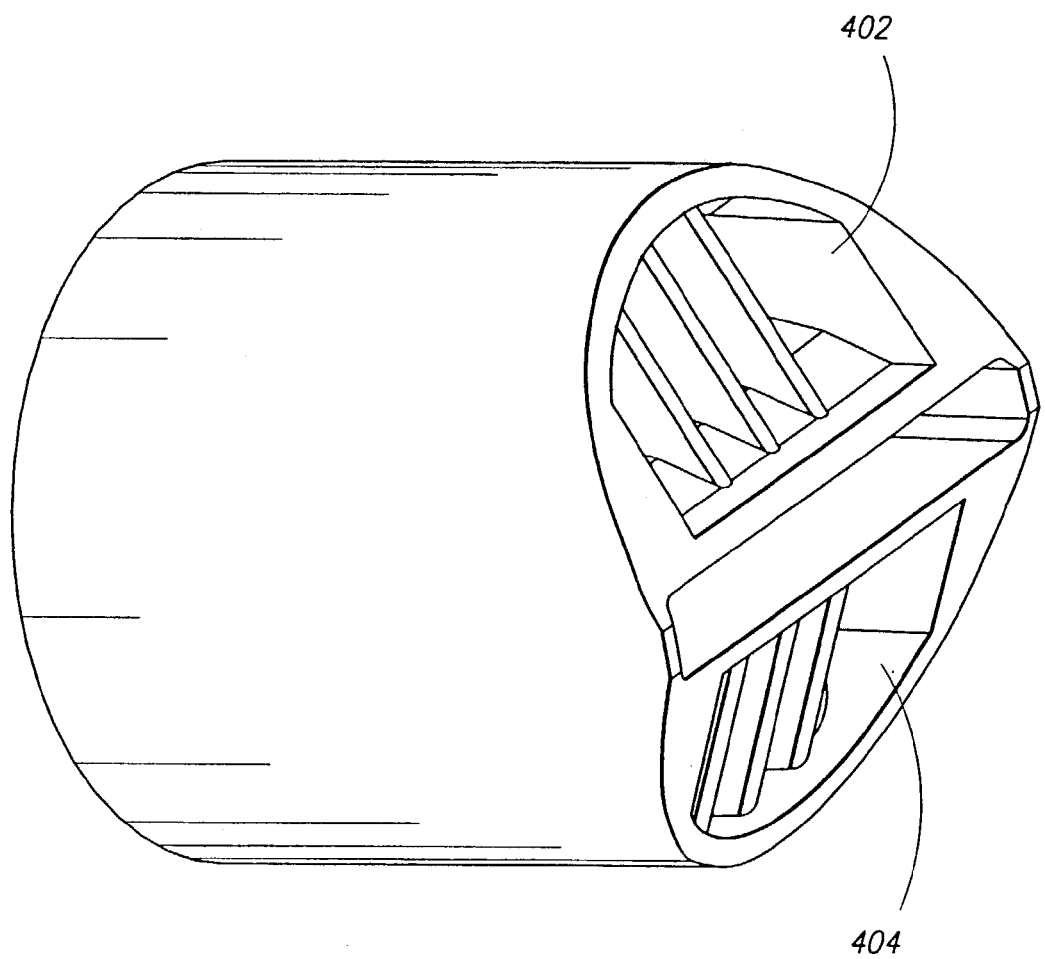
FIG. 43 is a perspective view of the device of FIG. 38 wherein the needle carrier has been removed to clearly show the vacuum ports.

After the valve leaflets are captured as described above, needle carrier 406 is advanced from the position shown in FIG. 38 to that of FIG. 39. The needle mechanism at this stage is compactly configured to avoid entangling chordae tendineae or papillary muscles during capture of the leaflets and initial needle deployment. Cams 428 are then advanced, pivoting the needle mounting blocks 410 and causing the needles 408 to deploy as shown in FIG. 40. Protruding stops on blocks 410 limit the angular deployment of the needles to the proper position for penetrating the valve leaflets. These stops come to rest against the needle carrier 406. The individual parts can be seen clearly in FIG. 42.

With the needles deployed, the needle carrier 406 is retracted proximally, causing the needle points to penetrate valve leaflets (not shown) and enter the vacuum ports 402 and 404. As the needles continue to move proximally, the points enter the needle catchers 414 which are essentially one way gripping devices. The needles advance until their grooves engage the jaws of the needle catchers 414. Needle catchers 414 are retained in the ports 402 and 404 by a vacuum adapter 430, shown in FIG. 42.

The needle carrier 406 advances distally pulling the needle mounting blocks 410 away from the needles which are retained by the needle catchers 414. The vacuum is disconnected and the device is withdrawn from the heart along with the needles 408 which are firmly held by the catchers 414. As the needles move outward, the sutures, which are loosely deployed in the body of the device 400, are pulled through the leaflets 432 and 434 to one of the positions shown in FIGS. 45*a* and 45*b*. Once the device is free of the access cannula, sutures 436 and 438, or 440 and 442, are cut from the needles and tied remotely using a knot rundown tool with an integral cutter to remove excess suture material.

Figure 46:
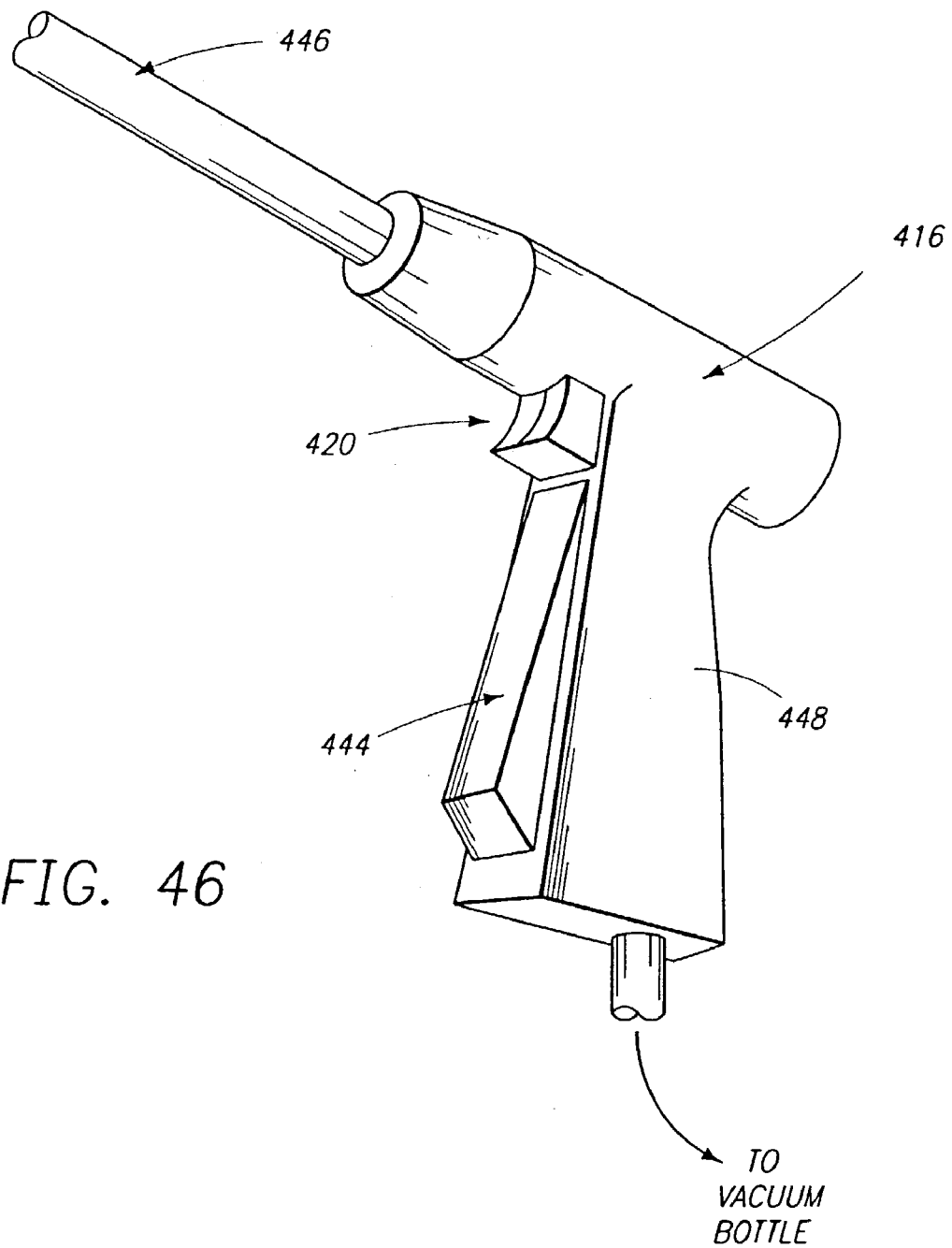
FIG. 46 is a perspective view of another exemplary embodiment of a handpiece that is utilized with the device of FIG. 38.

The proximal control handpieces 416 shown in FIGS. 44 and 46 are illustrative of alternate approaches to controlling the system. One objective is to permit single handed control of the vacuum ports and suture needles without destabilizing the device. It is useful to locate and hold the device precisely in relation to the beating heart in order to accomplish the surgical procedure with minimal blood loss. In operation, the surgeon will use one hand to stabilize the distal end of the device via the cannula where it enters the atrium and the other hand to operate the vacuum and suturing controls. Control functions are described below.

In the device shown in FIG. 44, handpiece 416 has a pistol-like configuration which includes a shaft portion 446 and a handle portion 448. A pair of vacuum controls 420 are positioned akin to pistol hammers at the back of shaft portion 446 and at the top of handle portion 448. In this embodiment vacuum controls 420 are thumb operated. Vacuum controls 420 are separately capable of being partially activated or fully activated by a toggle mechanism (not shown). When partially activated, the associated vacuum line is momentarily opened, allowing blood to flow into the vacuum source 418. If one of the controls 420 is released it will return to its normally closed position and flow to the associated line will stop immediately. Once a leaflet has been captured the control 420 can be moved to its extreme position where it will remain due to an internal toggle action. In this case vacuum is applied to retain the leaflet which, in turn, blocks the port, preventing blood flow.

In another embodiment shown in FIG. 46, the pair of vacuum controls 420 are located in the body 416 below the shaft portion 446 and in front of the handle portion 448. In this embodiment the vacuum controls 420 function like a pistol trigger, just above the needle control trigger 444, so that they can be operated individually by the index finger. In the arrangement shown, it will be necessary to actuate the control nearest the index finger first. The first action momentarily opens the vacuum line as described above. When the leaflet is captured the control is depressed further, causing it to latch into place by an internal toggle action. The second control 420 is now accessible to the index finger for capture of the second leaflet in similar manner.

In the embodiments shown in FIGS. 44 and 46 the trigger 444 is pivotably mounted in body 416 to control needle deployment after the leaflets are captured. The trigger is connected to needle driver 426 by a linkage internal to the body 416 which establishes the correct direction and stroke. The device is supplied with the trigger fully depressed to hold the needle array in the position shown in FIG. 38 relative to the vacuum ports 402 and 404. An internal latch in 416 retains the trigger. Once the leaflets have been captured the trigger is released, allowing the needles to advance to the position shown in FIG. 39. Near the end of the trigger stroke, needle driver 426 bears on cams 428 which, in turn, bear on blocks 410 causing the needles to deploy outward as in FIG. 40.

Squeezing the trigger 444 moves the needles proximally through the valve leaflets and into the vacuum ports 402 and 404 where they will be trapped as previously described. The trigger stroke will be internally limited so that it will not achieve the latched condition in which the cycle began. Releasing the trigger moves the needle carrier 406 forward, separating the needles from blocks 410. The entire device can now be removed, drawing sutures through the leaflets as previously described. The distal tip of the device 400 is rotatable relative to the body 416 for precise angular positioning of the ports 402 while maintaining a comfortable handle position for the user.

The present invention may be embodied in other specific forms without departing from its spirit, and the described embodiments are to be considered in all respects only as illustrative and not restrictive. The scope of the invention is, therefore, indicated by the claims and their equivalents rather than by the foregoing description.

What is claimed is:

1. A method of treating a heart valve, comprising:
providing a catheter having a distal portion with a first side and a second side;
advancing the catheter distal portion to a location adjacent a heart valve; and
grasping a first heart valve leaflet by applying a first vacuum only along the first side of the catheter distal portion;
wherein a second heart valve leaflet remains substantially unrestrained while grasping the first heart valve leaflet.

2. The method of claim 1, further comprising:
grasping the second heart valve leaflet by applying a second vacuum along the second side of the catheter distal portion.

3. The method of claim 2, wherein the second vacuum is applied to the second side of the catheter distal portion while maintaining application of the first vacuum to the first side of the catheter distal portion, wherein the first valve leaflet is held via the first vacuum to the catheter distal end portion while the second heart valve leaflet is grasped.

4. The method of claim 1, further comprising:
moving the first heart valve leaflet toward the second heart valve leaflet by manipulating the catheter distal portion toward the second valve leaflet.

5. The method of claim 4, further comprising:
applying a second vacuum along the second side of the catheter distal portion for grasping the second heart valve leaflet.

6. The method of claim 5, wherein the first and second vacuums are provided to the catheter from a common exterior vacuum source.

7. The method of claim 1, further comprising:
passing a first suture portion through the first heart valve leaflet.

8. The method of claim 7, further comprising:
grasping a second heart valve leaflet; and
passing a second suture portion through the second heart valve leaflet.

9. The method of claim 8, wherein the first suture portion and the second suture portion are each a portion of a common suture thread.

10. The method of claim 9, further comprising:
releasing the first and second heart valve leaflets from the catheter distal portion;
withdrawing the catheter distal portion from the treatment site, wherein withdrawing the catheter distal portion occurs prior to tightening of the common suture thread; and
tightening the common suture thread to secure the first heart valve leaflet to the second heart valve leaflet, wherein tightening the common suture thread occurs after releasing the first and second heart valve leaflets from the catheter distal portion.

11. The method of claim 10, wherein tightening the common suture thread occurs after withdrawal of the catheter distal portion from the location adjacent the heart valve.

12. A method of treating a heart valve, comprising:
advancing a catheter distal portion to a desired treatment site adjacent the heart valve;
grasping a first heart valve leaflet by applying suction to the catheter distal portion;
driving a first needle secured to a common suture thread into the first heart valve leaflet;
passing the first needle through the first heart valve leaflet to draw the common suture thread therethrough;
grasping a second heart valve leaflet by applying suction to the catheter distal portion;
driving a second needle secured to the common suture thread into the second heart valve leaflet;
passing the second needle through the second heart valve leaflet to draw the common suture thread therethrough;
releasing the first and second heart valve leaflets from the catheter distal portion; and
tightening the common suture thread to secure the first heart valve leaflet to the second heart valve leaflet, wherein tightening the common suture thread occurs after releasing the first and second heart valve leaflets from the catheter distal portion.

13. The method of claim 12, further comprising:
withdrawing the catheter distal portion from the treatment site, wherein withdrawing the catheter distal portion occurs prior to tightening of the common suture thread.

14. The method of claim 13, wherein at least a portion of the common suture is stored within the catheter distal portion, and withdrawing the catheter distal portion comprises trailing the suture out of the catheter distal portion.

15. The method of claim 12, further comprising:
tying a knot in the common suture thread.

16. The method of claim 12, wherein releasing the first and second heart valve leaflets comprises terminating the application of suction.

17. A method of treating a heart valve, comprising:
advancing a catheter distal portion to a desired location adjacent the heart valve;
stabilizing a first heart valve leaflet by releasably grasping a portion of the first heart valve leaflet with the catheter distal portion;
driving a first needle secured to a common suture thread into the first heart valve leaflet;
passing the first needle through the first heart valve leaflet to draw the common suture thread therethrough;
stabilizing a second heart valve leaflet by releasably grasping a portion of the second heart valve leaflet with the catheter distal portion;
driving a second needle secured to the common suture thread into the second heart valve leaflet;
passing the second needle through the second heart valve leaflet to draw the common suture thread therethrough;
releasing the first and second heart valve leaflets from the catheter distal portion; and
tightening the common suture thread to secure the first heart valve leaflet to the second heart valve leaflet, wherein tightening the common suture thread occurs after releasing the first and second heart valve leaflets from the catheter distal portion.

18. The method of claim 17, wherein the catheter distal portion comprises at least one vacuum port on a side of the catheter distal portion, and releasably grasping the portion of the first heart valve leaflet comprises applying vacuum to the vacuum port.

19. The method of claim 17, further comprising:
securing opposing ends of the common suture line together.

20. The method of claim 19, wherein securing opposing ends of the common suture line together comprises tying a knot in the common suture line.

* * * * *